US012698261B2

(12) United States Patent
Gray et al.

(10) Patent No.: US 12,698,261 B2
(45) Date of Patent: Aug. 4, 2026

(54) CYANO-PYRIMIDINE INHIBITORS OF EGFR/HER2

(71) Applicant: Dana-Farber Cancer Institute, Inc., Boston, MA (US)

(72) Inventors: Nathanael S. Gray, Boston, MA (US); John M. Hatcher, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 634 days.

(21) Appl. No.: 17/758,437

(22) PCT Filed: Jan. 6, 2021

(86) PCT No.: PCT/US2021/012270
§ 371 (c)(1),
(2) Date: Jul. 6, 2022

(87) PCT Pub. No.: WO2021/141960
PCT Pub. Date: Jul. 15, 2021

(65) Prior Publication Data
US 2023/0137932 A1 May 4, 2023

Related U.S. Application Data

(60) Provisional application No. 63/089,694, filed on Oct. 9, 2020, provisional application No. 62/957,993, filed on Jan. 7, 2020.

(51) Int. Cl.

| | |
|---|---|
| ***C07D 239/22*** | (2006.01) |
| ***A61K 45/06*** | (2006.01) |
| ***C07D 239/48*** | (2006.01) |
| ***C07D 251/10*** | (2006.01) |
| ***C07D 471/04*** | (2006.01) |
| ***C07D 487/04*** | (2006.01) |

(52) U.S. Cl.
CPC ............ *C07D 239/22* (2013.01); *A61K 45/06* (2013.01); *C07D 239/48* (2013.01); *C07D 251/10* (2013.01); *C07D 471/04* (2013.01); *C07D 487/04* (2013.01)

(58) Field of Classification Search
CPC .. A61K 2300/00; A61K 31/44; A61K 31/444; A61K 31/505; A61K 31/506; A61K 31/519; A61K 31/52; A61K 31/53; A61K 31/5377; A61K 45/06; A61P 35/00; C07D 213/85; C07D 239/22; C07D 239/48; C07D 251/10; C07D 251/48; C07D 403/04; C07D 403/12; C07D 471/04; C07D 473/16; C07D 487/04; C07D 495/04
See application file for complete search history.

(56) References Cited

U.S. PATENT DOCUMENTS

2019/0015413 A1* 1/2019 Si ......................... C07D 401/14

FOREIGN PATENT DOCUMENTS

| | | | | |
|---|---|---|---|---|
| EP | 3144292 A1 | 3/2017 | | |
| EP | 3173412 A1 | 5/2017 | | |
| EP | 3392245 A1 | 10/2018 | | |
| WO | WO 2013/169401 A1 | 11/2013 | | |
| WO | WO-2016054987 A1 * | 4/2016 | .............. | A61P 35/02 |
| WO | WO-2016082713 A1 * | 6/2016 | ......... | A61K 31/4523 |
| WO | WO-2017114500 A1 * | 7/2017 | ........... | C07D 403/04 |
| WO | WO-2017219500 A1 * | 12/2017 | ........... | C07D 239/48 |
| WO | WO-2019149164 A1 * | 8/2019 | ........... | A61K 31/505 |

OTHER PUBLICATIONS

Machine Translation of WO2016082713 (Year: 2016).*
Machine Translation of WO2017219500 (Year: 2017).*
Bioisostere Wikipedia, https://en.wikipedia.org/wiki/Bioisostere, Obtained from the internet Feb. 13, 2025; Internet Archive Wayback Machine Date Jan. 6, 2017 (Year: 2017).*
CAS Registry File 2226388-64-1; entered into STN Jun. 5, 2018; obtained from the internet Sep. 10, 2025 (Year: 2018).*
Machine Translation of WO2016054987 (Year: 2016).*
Machine Translation of WO2017114500 (Year: 2017).*
Cecil Textbook of Medicine, 20th Ed., vol. 1 (Year: 1997).*
Koga et al., "Utility of the Ba/F3 cell system for exploring on-target mechanisms of resistance to targeted therapies for lung cancer", Cancer Science (Year: 2022).*
Wu et al., Small-molecule inhibitors, immune checkpoint inhibitors, and more: FDA-approved novel therapeutic drugs for solid tumors from 1991 to 2021; Journal of Hematology & Oncology, 15, 143 (Year: 2022).*
Hu et al., "Discovery of selective EGFR modulator to inhibit L858R/T790M double mutants bearing a N-9-Diphenyl-9H-purin-2-amine scaffold", Bioorganic & Medicinal Chemistry 26:1810-1822 (2018).

(Continued)

*Primary Examiner* — Jeffrey H Murray
*Assistant Examiner* — Daniel John Burkett
(74) *Attorney, Agent, or Firm* — Nielsen IP Law LLC

(57) ABSTRACT

This disclosure provides compounds of Formula (I):

(I)

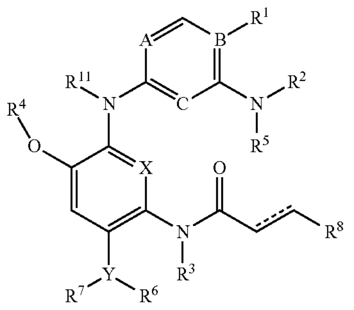

or a pharmaceutically acceptable salt thereof and pharmaceutical compositions comprising compounds of Formula (I) or a pharmaceutically acceptable salt thereof which are inhibitors of EGFR and HER2 useful for the treatment of EGFR/HER2 susceptible disorders such as cancer, including cancer of the lung, colon, breast, and thyroid.

19 Claims, No Drawings

(56) References Cited

OTHER PUBLICATIONS

Chen et al., "Discovery of N-(5-((5-chloro-4-((2-(isopropysulfony)phenyl)amino)pyrimidin-2-yl)amino)-4-mthoxy-2-(4-methyl-1,4-diazepan-1-yl)phenyl)acrylamide (CHMFL-ALK-EGFR-050) as a potent ALK-EGFR dual kinase inhibitor capable of overcoming a variety of ALK-EGFR associated drug resistant mutants in NSCLC", *European Journal of Medicinal Chemistry* 139:674-697 (2017).

International Preliminary Report on Patentability and Written Opinion for International Application No. PCT/US2021/012270, mailed May 6, 2021, 7 pages.

International Search Report for International Application No. PCT/US2021/012270, mailed May 6, 2021, 4 pages.

Schiff et al., "Characterization of the kinetics of the passive and active transport mechanisms for bile acid absorption in the small intestine and solon of the rat", *The Journal of Clinical Investigation* 51(6): 1351-1362 (1972).

Yan et al., "Discovery of novel 2,4-diarylaminopyrimidine derivatives as potent and selective epidermal growth factor receptor (EGFR) inhibitors against L858R/T790M resistance mutation", *European Journal of Medicinal Chemistry* 152:298-306 (2018).

* cited by examiner

CYANO-PYRIMIDINE INHIBITORS OF EGFR/HER2

RELATED APPLICATIONS

This application is a 35 U.S.C. § 371 filing of International Patent Application No. PCT/US2021/012270, filed Jan. 6, 2021, which claims priority to U.S. provisional application No. 62/957,993 filed Jan. 7, 2020 and U.S. provisional application No. 63/089,694 filed Oct. 9, 2020, the contents of which are hereby incorporated in their entireties.

BACKGROUND

Epidermal growth factor receptor (EGFR) and human epidermal growth factor receptor 2 (HER2) mutations are major causes of non-small cell lung cancer (NSCLC). EGFR mutations are frequently observed in NSCLC, and occasionally in other cancer types including colon cancer, breast cancer, endometrial cancer, and thyroid cancer. Somatic activating mutations in the kinase domain of EGFR occur in roughly 15% of NSCLC cases. A number of mutations that lead to structurally diverse mutant proteins have been identified, but the most common include small deletions in exon 19 (~45%), the L858R point mutation (~45%), and in-frame insertions in exon 20 (~5%) (Shigematsu, H. et al. *J Natl Cancer Inst,* 2005, 97, 339-346; Kosaka, T. et al. *Cancer Res.* 2004, 64, 8919-8923). Mutations in HER2, an ERBB receptor tyrosine kinase family member, occur in 2-6% cases of NSCLC with the predominant mutations being exon 20 insertions (Shigematsu, H. et al. *Cancer Res.* 2005, 65, 1642-1646). Owing to their status as key drivers of NSCLC, targeted disruption of mutant EGFR and HER2 leads to a strong clinical response. Patients carrying either the L858R mutation or exon 19 alterations typically respond well to the EGFR TKIs gefitinib and erlotinib (Yu, H. A. & Pao, W. *Nat Rev Clin Oncol,* 2013, 10, 551-552). Third generation inhibitors, including osimertinib and rociletinib, target the EGFR T790M "gatekeeper" mutant, a mutation responsible for approximately 50% of the acquired resistance to 1st and 2nd generation EGFR TKIs. Despite these promising clinical results, several de novo and acquired EGFR and HER2 mutations remain impervious to current therapies.

Therefore, there remains a need for preparing structurally diverse EGFR and HER2 inhibitors, particularly ones that are potent and/or selective inhibitors that can withstand EGFR and HER2 mutations.

SUMMARY

Provided herein are compounds and methods of using these compounds to treat disorders related to EGFR and HER2 function, including cancer.

In an aspect, provided herein are compounds of Formula I:

(I)

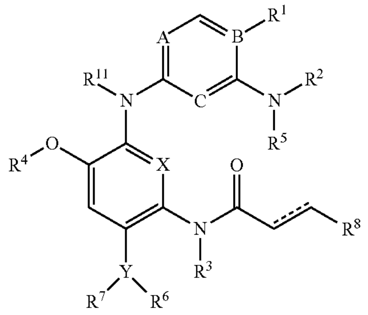

or a pharmaceutically acceptable salt thereof, wherein the variables are defined herein.

In an embodiment, the compound of Formula I is a compound of Formula II:

(II)

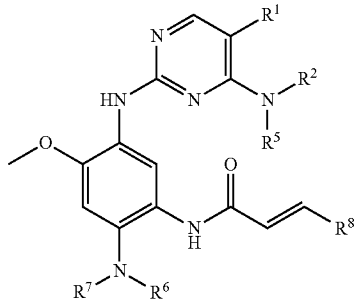

or a pharmaceutically acceptable salt thereof.

In another embodiment, the compound of Formula I is a compound of Formula III:

(III)

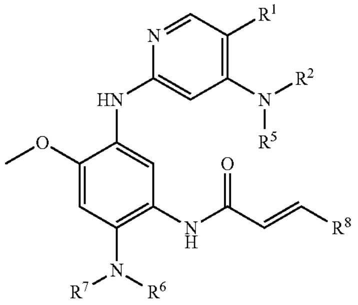

or a pharmaceutically acceptable salt thereof.

In yet another embodiment, the compound of Formula I is a compound of Formula IV:

(IV)

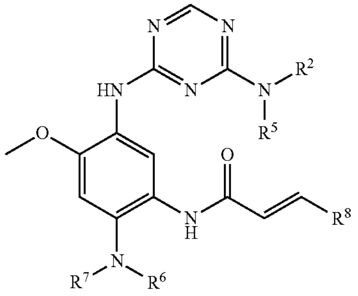

or a pharmaceutically acceptable salt thereof.

In still another embodiment, the compound of Formula I is a compound of Formula V:

(V)

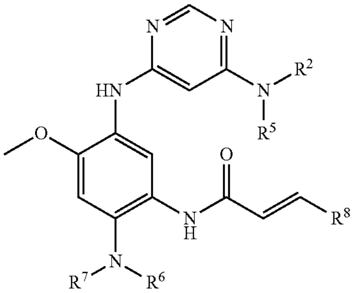

or a pharmaceutically acceptable salt thereof.

In another aspect, provided herein is a compound of Formula VI:

(VI)

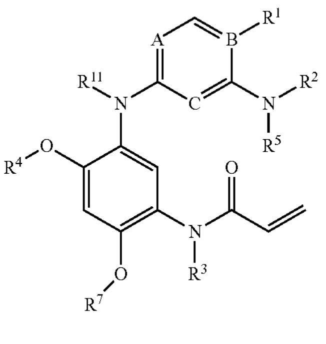

or a pharmaceutically acceptable salt thereof.

In another aspect, provided herein are pharmaceutical compositions comprising any of the compounds described herein, or a pharmaceutically acceptable salt thereof, together with a pharmaceutically acceptable carrier.

In an embodiment, the compound of Formula I is selected from the group consisting of a compound in Table 1.

TABLE 1

| Compound No. | Structure |
|---|---|
| 001 | 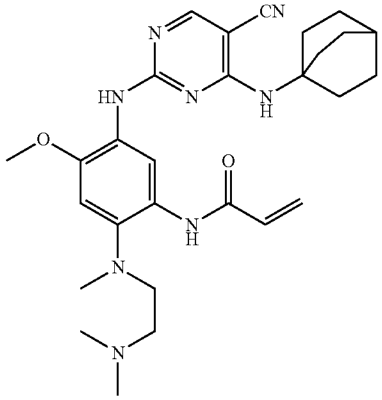 [SMILES: C=CC(=O)Nc1cc(Nc2ncc(C#N)c(NC34CCC(CC3)CC4)n2)c(OC)cc1N(C)CCN(C)C] |
| 002 | 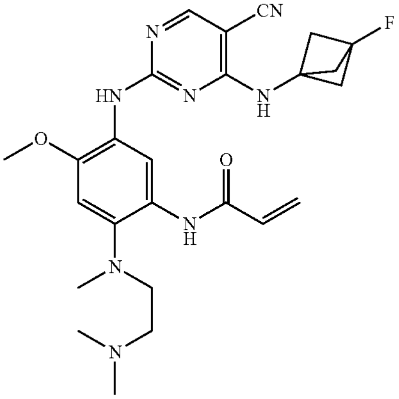 [SMILES: C=CC(=O)Nc1cc(Nc2ncc(C#N)c(NC34CC(F)(C3)C4)n2)c(OC)cc1N(C)CCN(C)C] |
| 003 | 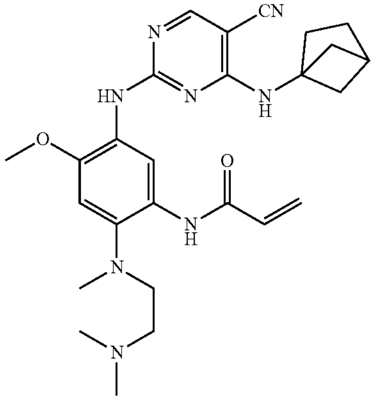 [SMILES: C=CC(=O)Nc1cc(Nc2ncc(C#N)c(NC34CCC(C3)C4)n2)c(OC)cc1N(C)CCN(C)C] |

TABLE 1-continued
| Compound No. | Structure |
|---|---|
| 004 | 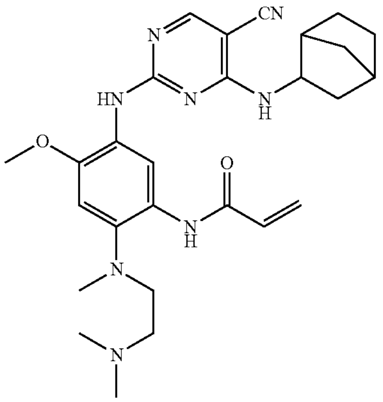 [SMILES: C=CC(=O)Nc1cc(Nc2ncc(C#N)c(NC3CC4CCC3C4)n2)c(OC)cc1N(C)CCN(C)C] |
| 005 | 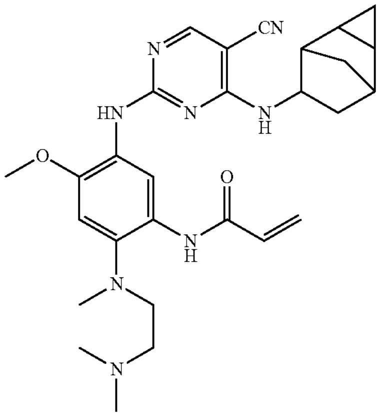 [SMILES: C=CC(=O)Nc1cc(Nc2ncc(C#N)c(NC3CC4CC3C3CC43)n2)c(OC)cc1N(C)CCN(C)C] |
| 006 | 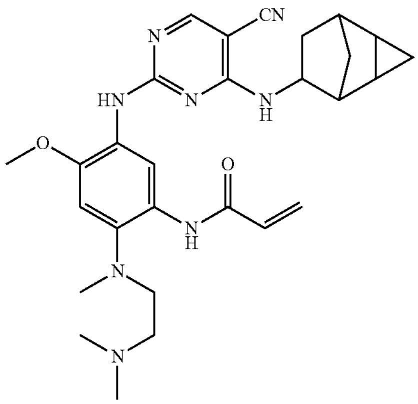 [SMILES: C=CC(=O)Nc1cc(Nc2ncc(C#N)c(NC3CC4CC3C3CC43)n2)c(OC)cc1N(C)CCN(C)C] |
TABLE 1-continued
| Compound No. | Structure |
|---|---|
| 007 | 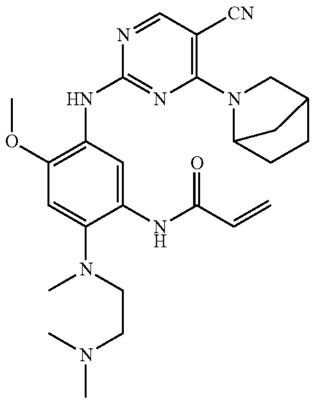 [SMILES: C=CC(=O)Nc1cc(Nc2ncc(C#N)c(N3CC4CCC3C4)n2)c(OC)cc1N(C)CCN(C)C] |
| 008 | 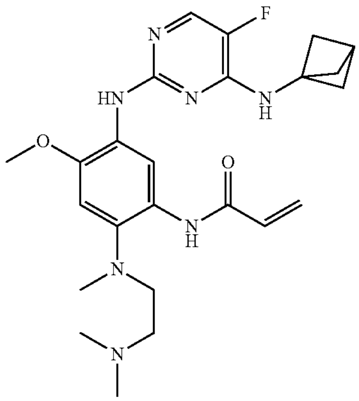 [SMILES: C=CC(=O)Nc1cc(Nc2ncc(F)c(NC34CC(C3)C4)n2)c(OC)cc1N(C)CCN(C)C] |
| 009 | 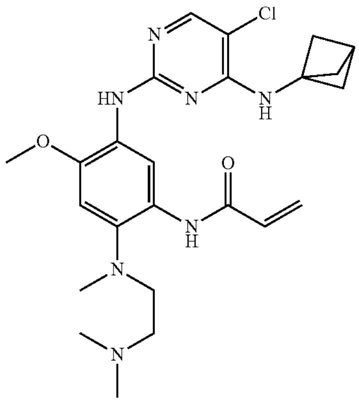 |

TABLE 1-continued
| Compound No. | Structure |
| --- | --- |
| 010 | 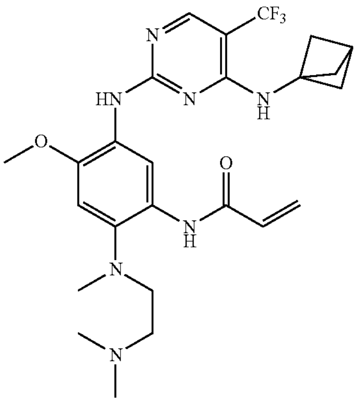 [SMILES: C=CC(=O)Nc1cc(Nc2ncc(Cl)c(NC34CC(C3)C4)n2)c(OC)cc1N(C)CCN(C)C] |
| 011 | 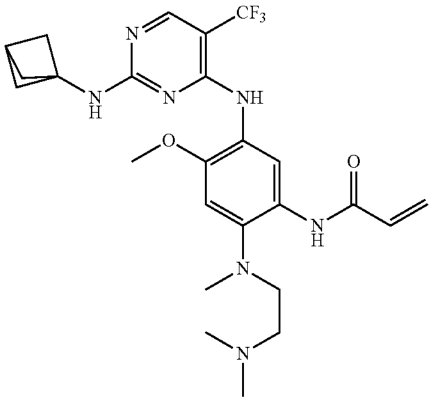 [SMILES: C=CC(=O)Nc1cc(Nc2nc(NC34CC(C3)C4)ncc2C(F)(F)F)c(OC)cc1N(C)CCN(C)C] |
| 012 | 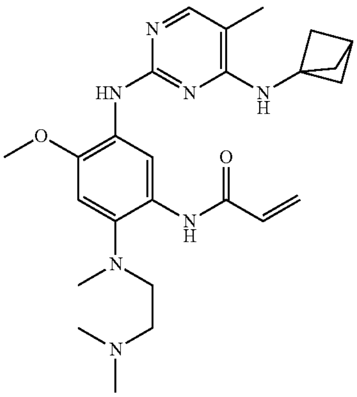 [SMILES: C=CC(=O)Nc1cc(Nc2ncc(C)c(NC34CC(C3)C4)n2)c(OC)cc1N(C)CCN(C)C] |
TABLE 1-continued
| Compound No. | Structure |
| --- | --- |
| 013 | 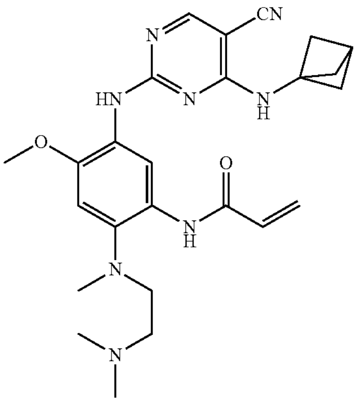 |
| 014 | 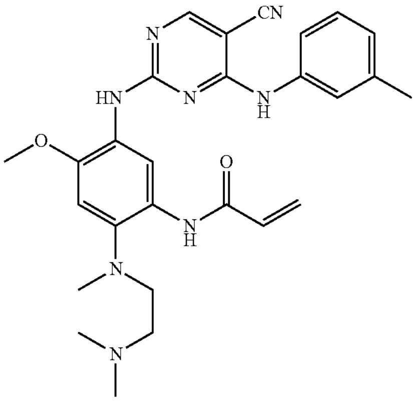 |
| 015 | 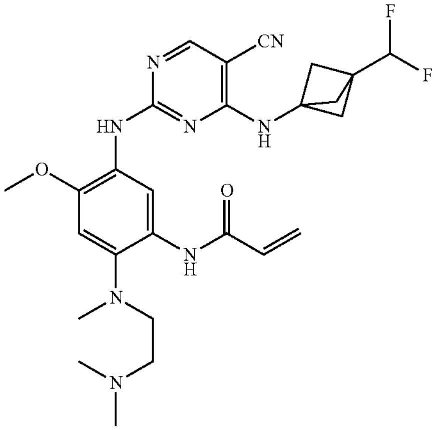 [SMILES: C=CC(=O)Nc1cc(Nc2ncc(C#N)c(NC34CC(C(F)F)(C3)C4)n2)c(OC)cc1N(C)CCN(C)C] |

TABLE 1-continued
| Compound No. | Structure |
|---|---|
| 016 | 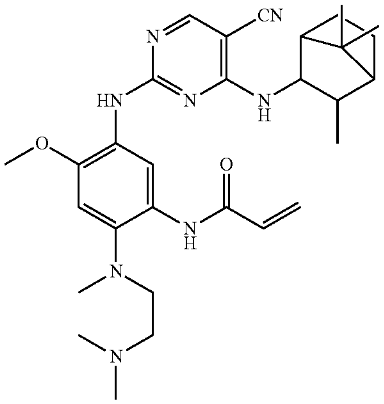 |
| 017 | 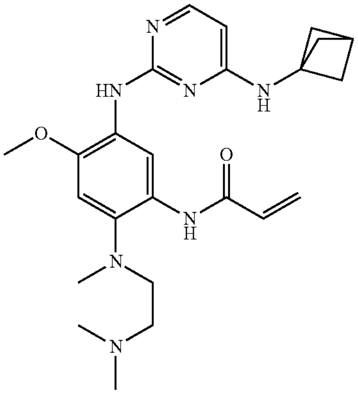 [SMILES: C=CC(=O)Nc1cc(Nc2nccc(NC34CC(C3)C4)n2)c(OC)cc1N(C)CCN(C)C] |
| 018 | 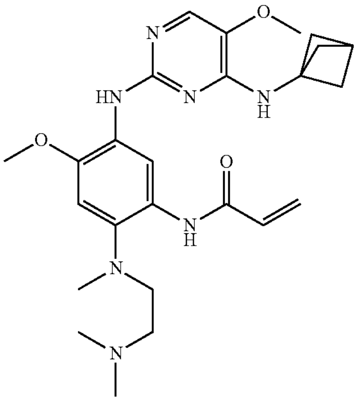 [SMILES: C=CC(=O)Nc1cc(Nc2ncc(OC)c(NC34CC(C3)C4)n2)c(OC)cc1N(C)CCN(C)C] |
TABLE 1-continued
| Compound No. | Structure |
|---|---|
| 019 | 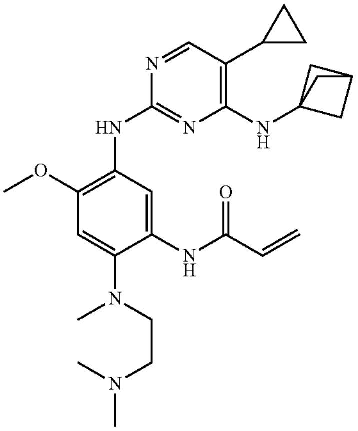 [SMILES: C=CC(=O)Nc1cc(Nc2ncc(C3CC3)c(NC34CC(C3)C4)n2)c(OC)cc1N(C)CCN(C)C] |
| 020 | 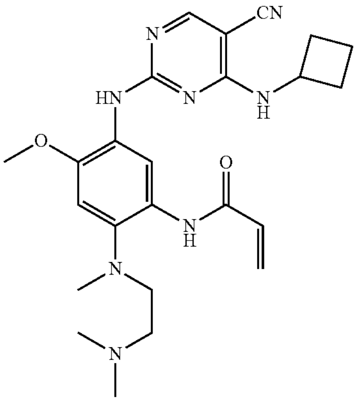 [SMILES: C=CC(=O)Nc1cc(Nc2ncc(C#N)c(NC3CCC3)n2)c(OC)cc1N(C)CCN(C)C] |
| 021 | 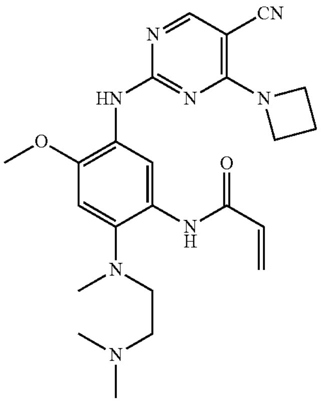 [SMILES: C=CC(=O)Nc1cc(Nc2ncc(C#N)c(N3CCC3)n2)c(OC)cc1N(C)CCN(C)C] |
| 022 | 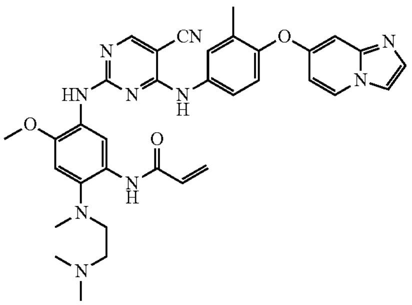 [SMILES: C=CC(=O)Nc1cc(Nc2ncc(C#N)c(Nc3ccc(Oc4ccn5ccnc5c4)c(C)c3)n2)c(OC)cc1N(C)CCN(C)C] |

TABLE 1-continued
| Compound No. | Structure |
|---|---|
| 023 | 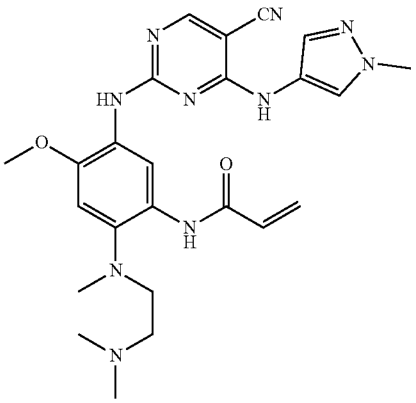 |
| 024 | 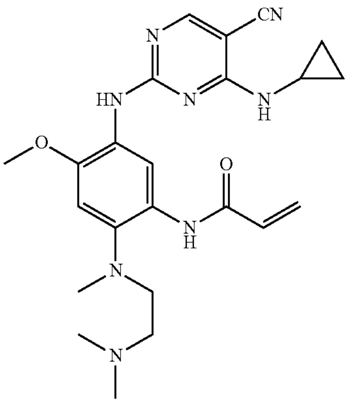 [SMILES: C=CC(=O)Nc1cc(Nc2ncc(C#N)c(NC3CC3)n2)c(OC)cc1N(C)CCN(C)C] |
| 025 | 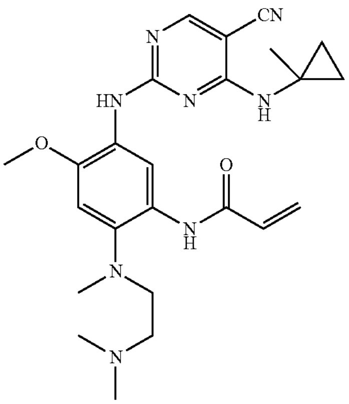 [SMILES: C=CC(=O)Nc1cc(Nc2ncc(C#N)c(NC3(C)CC3)n2)c(OC)cc1N(C)CCN(C)C] |
TABLE 1-continued
| Compound No. | Structure |
|---|---|
| 026 | 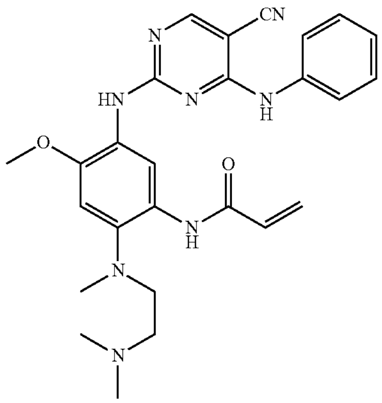 [SMILES: C=CC(=O)Nc1cc(Nc2ncc(C#N)c(Nc3ccccc3)n2)c(OC)cc1N(C)CCN(C)C] |
| 027 | 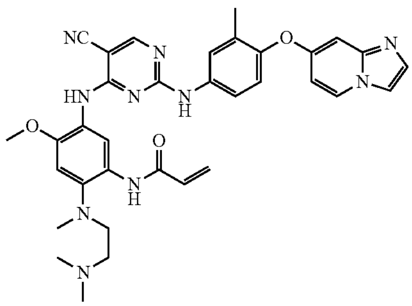 [SMILES: C=CC(=O)Nc1cc(Nc2nc(Nc3ccc(Oc4ccn5ccnc5c4)c(C)c3)ncc2C#N)c(OC)cc1N(C)CCN(C)C] |
| 028 | 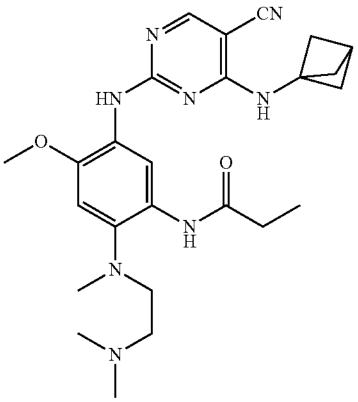 [SMILES: CCC(=O)Nc1cc(Nc2ncc(C#N)c(NC34CC(C3)C4)n2)c(OC)cc1N(C)CCN(C)C] |
| 029 | 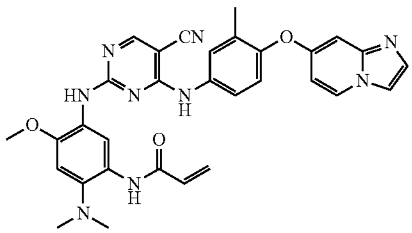 [SMILES: C=CC(=O)Nc1cc(Nc2ncc(C#N)c(Nc3ccc(Oc4ccn5ccnc5c4)c(C)c3)n2)c(OC)cc1N(C)C] |

TABLE 1-continued
| Compound No. | Structure |
|---|---|
| 030 | 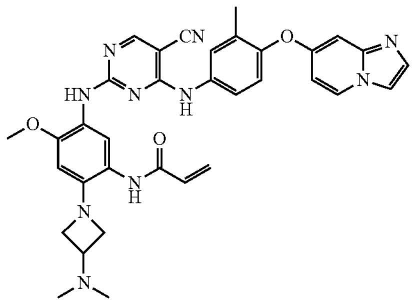 [SMILES: C=CC(=O)Nc1cc(Nc2ncc(C#N)c(Nc3ccc(Oc4ccn5ccnc5c4)c(C)c3)n2)c(OC)cc1N1CC(N(C)C)C1] |
| 031 | 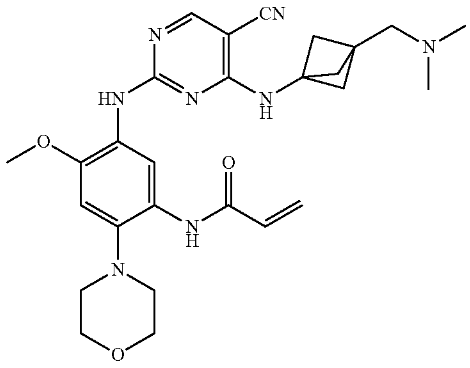 |
| 032 | 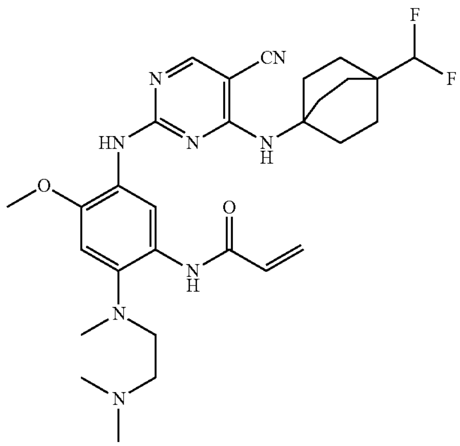 [SMILES: C=CC(=O)Nc1cc(Nc2ncc(C#N)c(NC34CCC(C(F)F)(CC3)CC4)n2)c(OC)cc1N(C)CCN(C)C] |
| 033 | 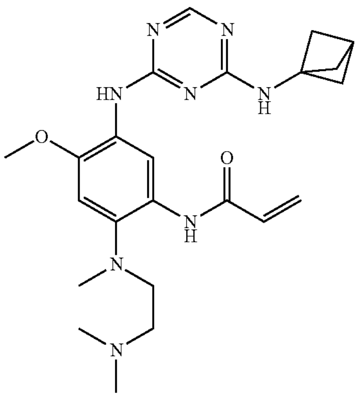 [SMILES: C=CC(=O)Nc1cc(Nc2ncnc(NC34CC(C3)C4)n2)c(OC)cc1N(C)CCN(C)C] |
TABLE 1-continued
| Compound No. | Structure |
|---|---|
| 034 | 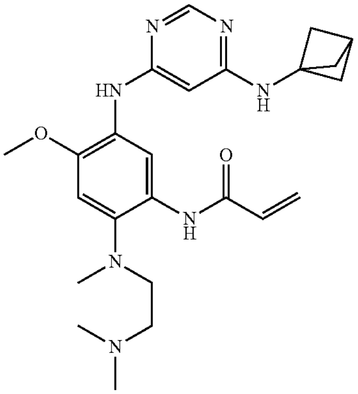 [SMILES: C=CC(=O)Nc1cc(Nc2cc(NC34CC(C3)C4)ncn2)c(OC)cc1N(C)CCN(C)C] |
| 035 | 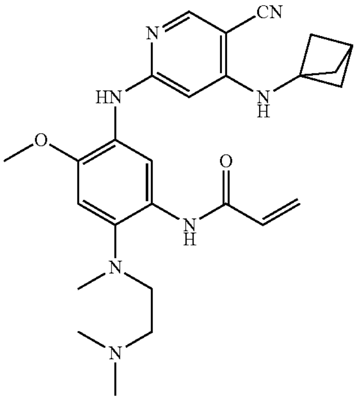 [SMILES: C=CC(=O)Nc1cc(Nc2cc(NC34CC(C3)C4)c(C#N)cn2)c(OC)cc1N(C)CCN(C)C] |
| 036 | 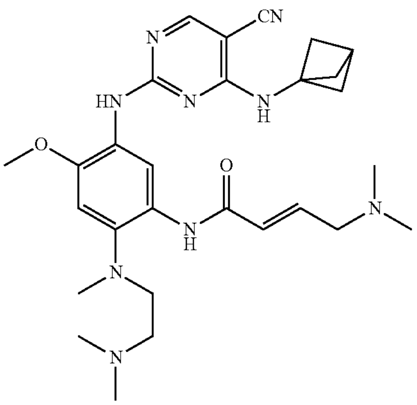 |

TABLE 1-continued
| Compound No. | Structure |
|---|---|
| 037 | 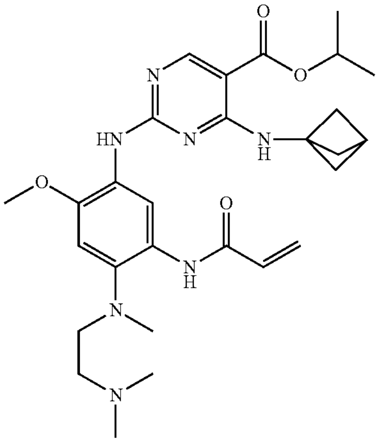 [SMILES: C=CC(=O)Nc1cc(Nc2ncc(C(=O)OC(C)C)c(NC34CC(C3)C4)n2)c(OC)cc1N(C)CCN(C)C] |
| 038 | 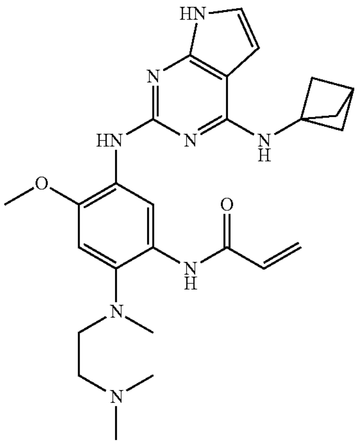 [SMILES: C=CC(=O)Nc1cc(Nc2nc(NC34CC(C3)C4)c3cc[nH]c3n2)c(OC)cc1N(C)CCN(C)C] |
| 039 | 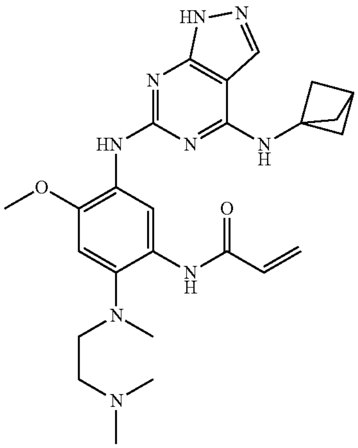 [SMILES: C=CC(=O)Nc1cc(Nc2nc(NC34CC(C3)C4)c3cn[nH]c3n2)c(OC)cc1N(C)CCN(C)C] |
TABLE 1-continued
| Compound No. | Structure |
|---|---|
| 040 | 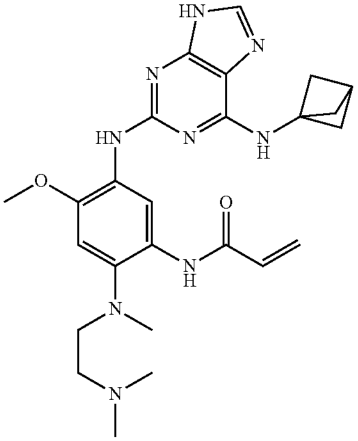 [SMILES: C=CC(=O)Nc1cc(Nc2nc(NC34CC(C3)C4)c3nc[nH]c3n2)c(OC)cc1N(C)CCN(C)C] |
| 041 | 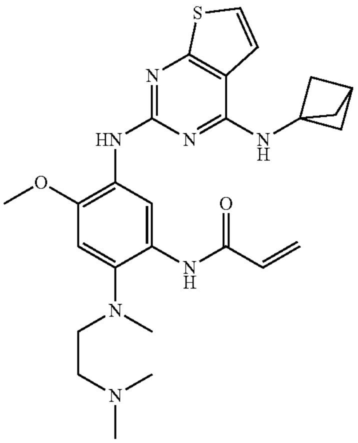 [SMILES: C=CC(=O)Nc1cc(Nc2nc(NC34CC(C3)C4)c3ccsc3n2)c(OC)cc1N(C)CCN(C)C] |
| 042 | 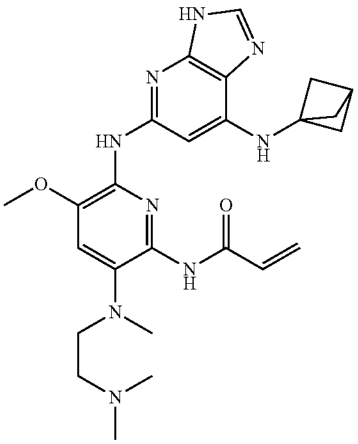 [SMILES: C=CC(=O)Nc1nc(Nc2cc(NC34CC(C3)C4)c3nc[nH]c3n2)c(OC)cc1N(C)CCN(C)C] |

TABLE 1-continued

| Compound No. | Structure |
|---|---|
| 043 | 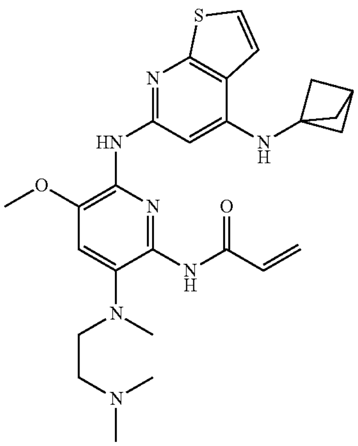 [SMILES: C=CC(=O)Nc1nc(Nc2cc(NC34CC(C3)C4)c3ccsc3n2)c(OC)cc1N(C)CCN(C)C] |

or a pharmaceutically acceptable salt thereof.

In yet another aspect, provided herein are methods of treating cancer in an individual in need thereof, comprising administering to the individual a therapeutically effective amount of any of the compounds or compositions described herein.

In an aspect, provided herein are methods of inhibiting EGFR and/or HER2 in an individual in need thereof, comprising administering to the individual a therapeutically effective amount of any of the compounds or compositions described herein.

DETAILED DESCRIPTION

Provided herein are compounds, or pharmaceutically acceptable salts thereof, that are useful in the treatment of cancer or a neurodegenerative disease in an individual in need thereof.

In a non-limiting aspect, these compounds can inhibit EGFR and/or HER2. In a particular embodiment, the compounds provided herein are considered EGFR and/or HER2 inhibitors. As such, in one aspect, the compounds provided herein are useful in the treatment of cancer in an individual by acting as an EGFR and/or HER2 inhibitor.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "treat," "treated," "treating," or "treatment" includes the diminishment or alleviation of at least one symptom associated or caused by the state, disorder or disease being treated. In certain embodiments, the treatment comprises bringing into contact with EGFR and/or HER2 an effective amount of a compound of the invention for conditions related to cancers, hemoglobinopathies, or myelodysplastic syndrome.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example, in Remington's Pharmaceutical Sciences (Genaro, Ed., Mack Publishing Co., 1985, Easton, PA), which is incorporated herein by reference.

The term "EGFR" refers to epidermal growth factor receptor, which is a transmembrane protein that is a receptor for members of the epidermal growth factor family (EGF family) of extracellular protein ligands. The epidermal growth factor receptor is a member of the ErbB family of receptors, a subfamily of four closely related receptor tyrosine kinases: EGFR (ErbB-1), HER2/neu (ErbB-2), Her 3 (ErbB-3) and Her 4 (ErbB-4). In many cancer types, mutations affecting EGFR expression or activity could result in cancer.

The term "HER2" refers to a protein that in humans is encoded by the ERBB2 gene. It is also frequently called HER2/neu. HER2 is a member of the human epidermal growth factor receptor (HER/EGFR/ERBB) family. Amplification or over-expression of this oncogene has been shown to play an important role in the development and progression of certain aggressive types of breast cancer. In recent years the protein has become an important biomarker and target of therapy for approximately 30% of breast cancer patients.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. In an embodiment, $C_1$-$C_6$ alkyl groups are provided herein. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkylamine," refers to the groups alkyl-$NH_2$, alkyl-NH(alkyl), and alkyl-N$(alkyl)_2$, wherein alkyl is as defined herein. Alkylamine includes, by way of example, ethanamine, methanamine, dimethylamine, trimethylamine, dimethylethanamine, and the like. In an embodiment, $C_1$-$C_6$ alkylamine groups are provided herein.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_4$ alkoxy groups are provided herein.

As used herein, the term "cyano," refers to the group —CN, wherein the cyano group consists of a carbon atom triple-bonded to a nitrogen atom.

As used herein, the term "halo" or "halogen" alone or as part of another substituent means, unless otherwise stated, a fluorine (fluoro), chlorine (chloro), bromine (bromo), or iodine (iodo) atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused, bridged, and/or spiro. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclo-propyl, cyclobutyl, cyclopentyl, cyclohexyl, bicyclo[3.1.0]hexyl, spiro[3.3]heptanyl, bicyclo[1.1.1]-pentyl, bicyclo[2.2.2]octane, and the like. In an embodiment, $C_3$-$C_8$ cycloalkyl groups are provided herein. It is to be understood that if a cycloalkyl moiety may be bonded or otherwise attached to a designated moiety through differing ring atoms (i.e., shown or described without denotation of a specific point of attachment), then all possible points are intended.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazo-lidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1]heptanyl, 2-azabicyclo[2.2.1]heptanyl, 3-azabicyclo[3.1.1]heptanyl, 2-azabicyclo[3.1.1]heptanyl, 3-aza-bicyclo[3.1.0]hexanyl, 2-azabicyclo[3.1.0]hexanyl, 3-azabicyclo[3.2.1]octanyl, 8-azabicyclo-[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]-heptanyl, 6-oxa-3-azabicyclo[3.1.1]heptanyl, 2-azaspiro[3.3]heptanyl, 2-oxa-6-azaspiro-[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In an embodiment, 3-10 membered heterocycloalkyl groups are provided herein.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms. In an embodiment, $C_5$-$C_7$ aryl groups are provided herein.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroiso-quinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta-[c]pyrazolyl, 5,6-dihydro-4H-pyrrolo[1,2-b]pyrazolyl, 6,7-dihydro-5H-pyrrolo[1,2-b][1,2,4]-triazolyl, 5,6,7,8-tetrahydro-[1,2,4]triazolo[1,5-a]pyridinyl, 4,5,6,7-tetrahydropyrazolo[1,5-a]-pyridinyl, 4,5,6,7-tetrahydro-1H-indazolyl and 4,5,6,7-tetrahydro-2H-indazolyl. In an embodiment, 5-10 membered heteroaryl groups are provided herein.

It is to be understood that if an aryl, heteroaryl, cycloalkyl, or heterocycloalkyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thioenyl, and so forth.

As used herein, the term "hydroxy," refers to the group —OH, wherein the hydroxy group consists of an oxygen carbon singly bonded to a hydrogen atom and a carbon atom.

As used herein, the term "nitro," refers to the group —$NO_2$, wherein the neutral nitro group consists of a positively charged nitrogen atom singly bonded to a carbon atom, singly bonded to a negatively charged oxygen atom, and doubly bonded to an oxygen atom.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

In an aspect, provided herein are compounds of Formula I:

(I)

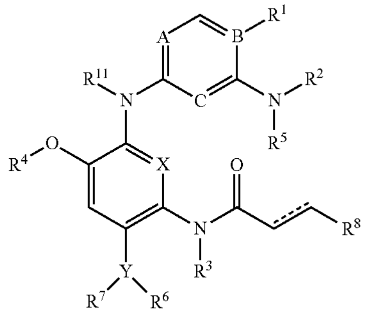

or a pharmaceutically acceptable salt thereof;

wherein:

⎓ is an optional double bond;

A, B, and C are independently, at each occurrence, N, C, C—CN, or CH;

X is N or CH;

Y is N or O, provided that when Y is O, $R^6$ is absent;

$R^1$ is selected from the group consisting of hydrogen, halo, hydroxy, cyano, nitro, $C_1$-$C_3$ alkyl, $C_3$-$C_6$ cycloalkyl, $COR^{11}$, $CO_2R^{11}$, and $C_1$-$C_4$ alkoxy, wherein $R^1$ is absent if B is N or B is C—CN, and $C_1$-$C_3$ alkyl is optionally substituted with halo;

$R^2$ is selected from the group consisting of $C_6$-$C_8$ aryl, 5-7 membered heteroaryl, and $C_3$-$C_8$ cycloalkyl; wherein $C_6$-$C_8$ aryl, 5-7 membered heteroaryl, and $C_3$-$C_8$ cycloalkyl are optionally substituted with one, two, or three Re;

$R^3$ is hydrogen or $C_1$-$C_6$ alkyl;

$R^4$ is hydrogen or $C_1$-$C_4$ alkyl;

$R^5$ is hydrogen or methyl;

alternatively, $R^2$ and $R^5$, together with the nitrogen atom to which they are attached, form a 4-7 membered heterocyclic ring;

$R^6$ is hydrogen or $C_1$-$C_6$ alkyl;

$R^7$ is $C_1$-$C_6$ alkyl or —$C_1$-$C_4$ alkyl-N($C_1$-$C_4$ alkyl)$_2$;

or, alternatively, $R^6$ and $R^7$, together with the nitrogen to which they are attached, form a 4- or 5-membered heterocyclic ring; wherein the 4- or 5-membered heterocyclic ring is optionally substituted with one or two $R^{10}$;

$R^8$ is hydrogen or $CH_2N(CH_3)_2$;

$R^9$ is, independently at each occurrence, selected from the group consisting of halo, $C_1$-$C_6$ alkyl, hydroxy, $C_1$-$C_6$ alkoxy, 5-10 membered heteroaryl, O-(5-10 membered heteroaryl), and $C_1$-$C_6$ alkylamine, wherein $C_1$-$C_6$ alkyl is optionally substituted with one, two, or three halo or $N(CH_3)_2$;

or, alternatively, two $R^9$ groups, together with the atoms to which they are attached, form a 3-, 4-, or 5-membered ring;

$R^{10}$ is selected from the group consisting of —OH, $C_1$-$C_4$ alkoxy, and $N(CH_3)_2$; and $R^{11}$ is independently, at each occurrence, selected from the group consisting of hydrogen, $C_1$-$C_6$ alkyl, and $C_3$-$C_8$ cycloalkyl.

In an embodiment, ═══ is a double bond.

In an embodiment, the compound of Formula I is a compound of Formula Ia:

(Ia)

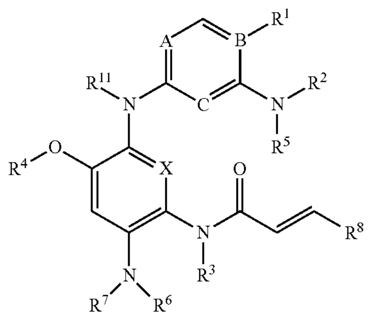

or a pharmaceutically acceptable salt thereof;

wherein:

A, B, and C are independently, at each occurrence, N, C, or CH;

X is CH;

$R^1$ is selected from the group consisting of hydrogen, halo, cyano, $C_1$-$C_3$ alkyl, $COR^{11}$, $CO_2R^{11}$, and $C_1$-$C_4$ alkoxy, wherein $R^1$ is absent if B is N, and $C_1$-$C_3$ alkyl is optionally substituted with halo;

$R^9$ is, independently at each occurrence, selected from the group consisting of halo, $C_1$-$C_6$ alkyl, hydroxy, $C_1$-$C_6$ alkoxy, 5-10 membered heteroaryl, O-(5-10 membered heteroaryl), and $C_1$-$C_6$ alkylamine, wherein $C_1$-$C_6$ alkyl is optionally substituted with one, two, or three halo;

$R^3$ is hydrogen;

$R^4$ is $C_1$-$C_4$ alkyl;

$R^5$ is hydrogen;

alternatively, $R^2$ and $R^5$, together with the nitrogen atom to which they are attached, form a 4-7 membered heterocyclic ring;

$R^6$ is hydrogen or $C_1$-$C_6$ alkyl;

$R^7$ is —$CH_2CH_2N(CH_3)_2$;

or, alternatively, $R^6$ and $R^7$, together with the nitrogen to which they are attached, form a 4- or 5-membered heterocyclic ring; wherein the 4- or 5-membered heterocyclic ring is optionally substituted with one or two $R^{10}$;

$R^8$ is hydrogen or $CH_2N(CH_3)_2$;

$R^9$ is, independently at each occurrence, selected from the group consisting of halo, $C_1$-$C_6$ alkyl, hydroxy, $C_1$-$C_6$ alkoxy, 5-10 membered heteroaryl, O-(5-10 membered heteroaryl), and $C_1$-$C_6$ alkylamine, wherein $C_1$-$C_6$ alkyl is optionally substituted with one, two, or three halo or $N(CH_3)_2$;

or, alternatively, two $R^9$ groups, together with the atoms to which they are attached, form a 3-, 4-, or 5-membered ring;

$R^{10}$ is —OH or $N(CH_3)_2$; and $R^{11}$ is independently, at each occurrence, selected from the group consisting of hydrogen, $C_1$-$C_6$ alkyl, and $C_3$-$C_6$ cycloalkyl.

In an embodiment, $R^4$ is $C_1$-$C_4$ alkyl. In another embodiment, $R^4$ is methyl. In still another embodiment, $R^5$ is hydrogen. In an embodiment, $R^7$ is —$C_1$-$C_4$ alkyl-N($C_1$-$C_4$ alkyl)$_2$. In another embodiment, $R^7$ is —$CH_2CH_2N(CH_3)_2$.

In an embodiment of Formula (I) and (Ia), no more than one of A, B, or C are C—CN. In another embodiment of Formula (I) and (Ia), C is C—CN. In yet another embodiment or Formula (I) and (Ia), A, B, and C are N, C, or CH.

In still another embodiment, the compound of Formula I is a compound of Formula II:

(II)

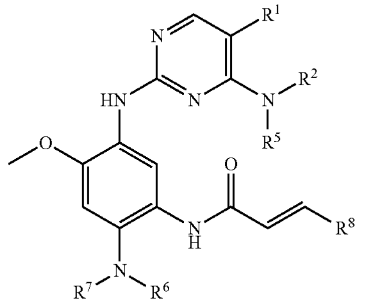

or a pharmaceutically acceptable salt thereof.

In an embodiment, the compound of Formula I is a compound of Formula III:

(III)

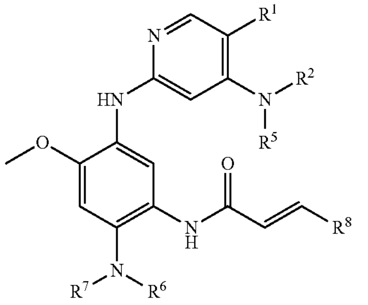

or a pharmaceutically acceptable salt thereof.

In another embodiment, the compound of Formula I is a compound of Formula IV:

(IV)

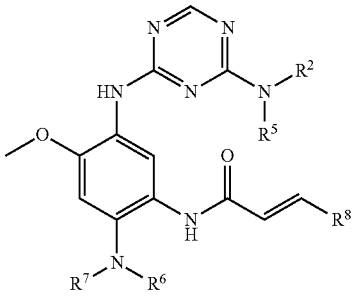

or a pharmaceutically acceptable salt thereof.

In yet another embodiment, the compound of Formula I is a compound of Formula V:

(V)

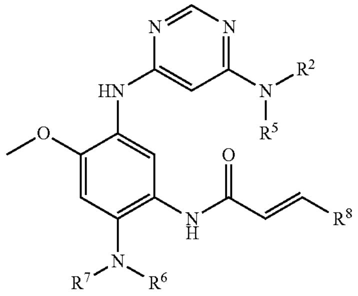

or a pharmaceutically acceptable salt thereof.

In another aspect, provided herein is a compound of Formula VI:

(VI)

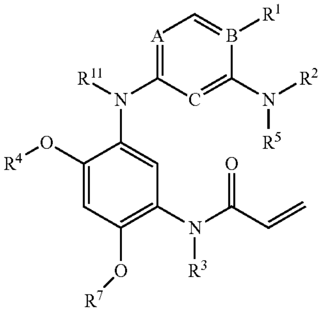

or a pharmaceutically acceptable salt thereof.

In another aspect, provided herein are compounds of Formula X:

(X)

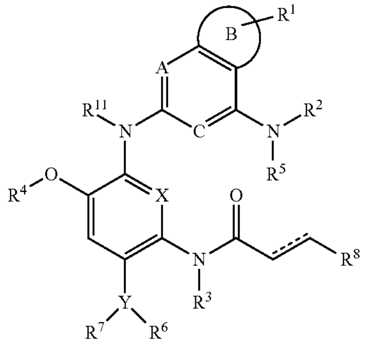

or a pharmaceutically acceptable salt thereof;

wherein:

=== is an optional double bond;

A and C are independently, at each occurrence, N, C, C—CN, or CH;

B is 5-10 membered heteroaryl;

X is N or CH;

Y is N or O, provided that when Y is O, $R^8$ is absent;

$R^1$ is selected from the group consisting of hydrogen, halo, hydroxy, cyano, nitro, $C_1$-$C_3$ alkyl, $C_1$-$C_3$ haloalkyl, $C_3$-$C_6$ cycloalkyl, $COR^{11}$, $CO_2R^{11}$, and $C_1$-$C_4$ alkoxy;

$R^2$ is selected from the group consisting of $C_6$-$C_8$ aryl, 5-7 membered heteroaryl, and $C_3$-$C_8$ cycloalkyl; wherein $C_6$-$C_8$ aryl, 5-7 membered heteroaryl, and $C_3$-$C_8$ cycloalkyl are optionally substituted with one, two, or three Re;

$R^3$ is hydrogen or $C_1$-$C_6$ alkyl;

$R^4$ is hydrogen or $C_1$-$C_4$ alkyl;

$R^5$ is hydrogen or methyl;

alternatively, $R^2$ and $R^5$, together with the nitrogen atom to which they are attached, form a 4-7 membered heterocyclic ring;

$R^6$ is hydrogen or $C_1$-$C_6$ alkyl;

$R^7$ is $C_1$-$C_6$ alkyl or —$C_1$-$C_4$ alkyl-N($C_1$-$C_4$ alkyl)$_2$;

or, alternatively, $R^6$ and $R^7$, together with the nitrogen to which they are attached, form a 4- or 5-membered heterocyclic ring; wherein the 4- or 5-membered heterocyclic ring is optionally substituted with one or two $R^{10}$;

$R^8$ is hydrogen or $CH_2N(CH_3)_2$;

$R^9$ is, independently at each occurrence, selected from the group consisting of halo, $C_1$-$C_6$ alkyl, hydroxy, $C_1$-$C_6$ alkoxy, 5-10 membered heteroaryl, O-(5-10 membered heteroaryl), and $C_1$-$C_6$ alkylamine, wherein $C_1$-$C_6$ alkyl is optionally substituted with one, two, or three halo or $N(CH_3)_2$;

or, alternatively, two $R^9$ groups, together with the atoms to which they are attached, form a 3-, 4-, or 5-membered ring;

$R^{10}$ is selected from the group consisting of —OH, $C_1$-$C_4$ alkoxy, and $N(CH_3)_2$; and $R^{11}$ is selected from the group consisting of hydrogen, $C_1$-$C_6$ alkyl, and $C_3$-$C_6$ cycloalkyl.

In an embodiment of Formula X, B is 5-membered heteroaryl.

In another embodiment of Formula X, B is selected from the group consisting of:

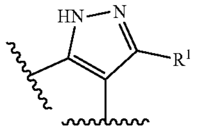
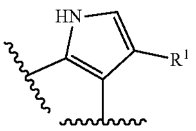
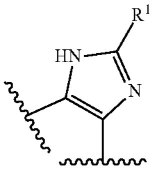

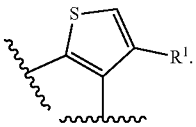

In an embodiment, the compound of Formula X is a compound of Formula Xa:

(Xa)

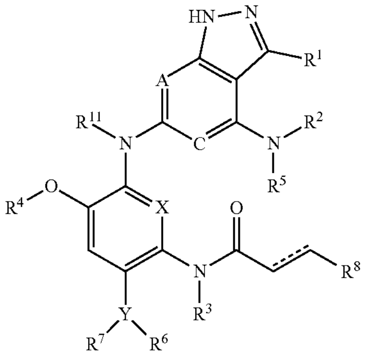

or a pharmaceutically acceptable salt thereof.

In another embodiment, the compound of Formula X is a compound of Formula Xb:

(Xb)

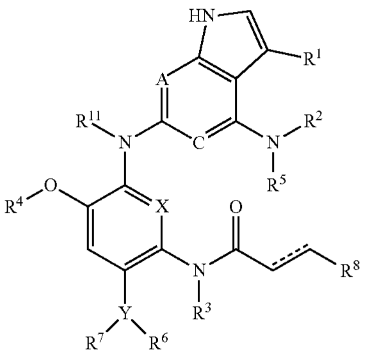

or a pharmaceutically acceptable salt thereof.

In yet another embodiment, the compound of Formula X is a compound of Formula Xc:

(Xc)

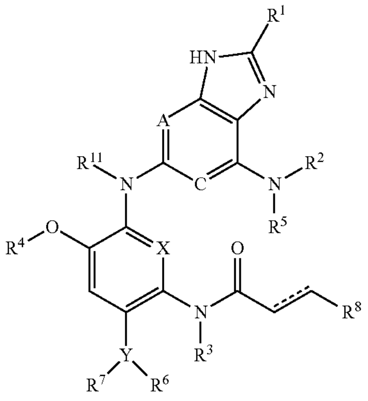

or a pharmaceutically acceptable salt thereof.

In still another embodiment, the compound of Formula X is a compound of Formula Xd:

(Xd)

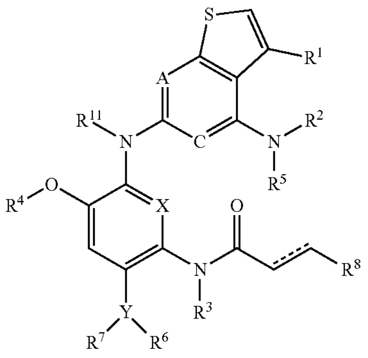

or a pharmaceutically acceptable salt thereof.

In still another embodiment, $R^1$ is cyano. In an embodiment, $R^1$ is selected from the group consisting of hydroxy, methoxy, and cyclopropyl. In another embodiment, $R^1$ is $CF_3$.

In yet another embodiment, $R^2$ is

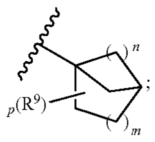

wherein:

m is 0, 1, or 2;

n is 1 or 2; and p is 0, 1, 2, or 3.

In still another embodiment, $R^6$ is $C_1$-$C_6$ alkyl. In an embodiment, $R^6$ is methyl and $R^7$ is $—CH_2CH_2N(CH_3)_2$. In another embodiment, $R^6$ and $R^7$, together with the nitrogen to which they are attached, form a 4- or 5-membered heterocyclic ring selected from the group consisting of

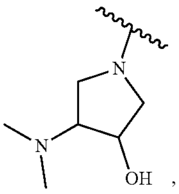
,
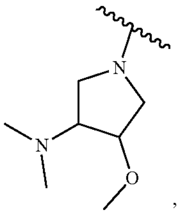
,
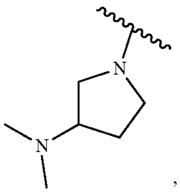
, and

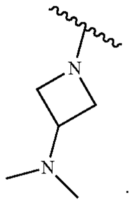
.

In yet another embodiment, $R^2$ is bicyclo[1.1.1]pentane that is optionally substituted with one, two, or three $R^9$. In still another embodiment, $R^2$ is bicyclo[1.1.1]pentane that is substituted with one $R^9$. In yet another embodiment, $R^2$ is bicyclo[1.1.1]pentane that is substituted with two $R^9$. In an embodiment, $R^2$ is bicyclo[1.1.1]pentane that is substituted with three $R^9$. In another embodiment, $R^2$ is bicyclo[2.2.2]octane that is optionally substituted with one, two, or three $R^9$. In yet another embodiment, $R^2$ is bicyclo[2.2.2]octane that is substituted with one $R^9$. In still another embodiment, $R^2$ is bicyclo[2.2.2]octane that is substituted with two $R^9$. In an embodiment, $R^2$ is bicyclo[2.2.2]octane that is substituted with three $R^9$.

In another embodiment, $R^2$ is selected from the group consisting of:

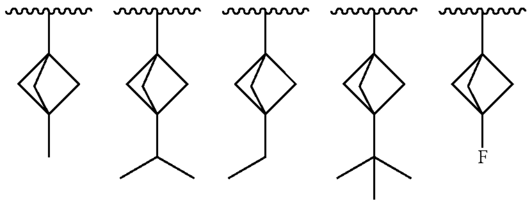

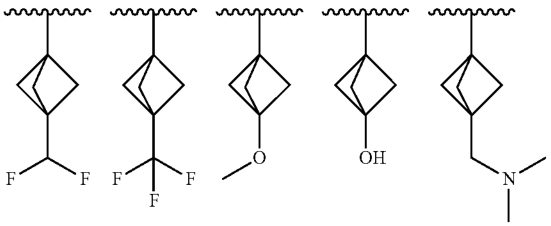

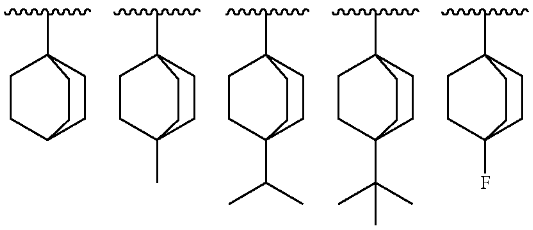

-continued

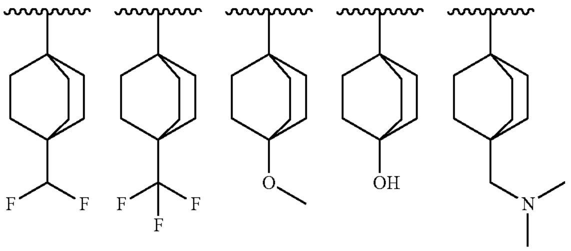

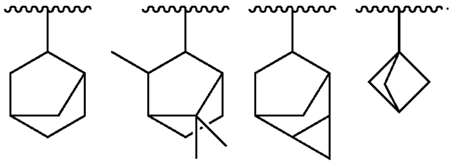
.

In an embodiment, the compound of Formula I is selected from the group consisting of

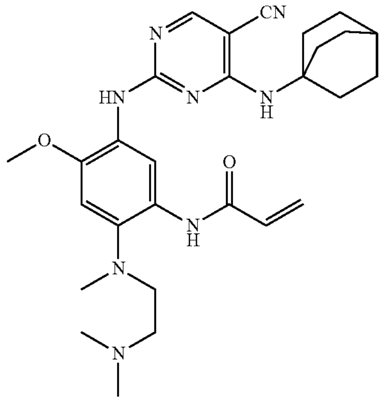 [SMILES: C=CC(=O)Nc1cc(Nc2ncc(C#N)c(NC34CCC(CC3)CC4)n2)c(OC)cc1N(C)CCN(C)C]

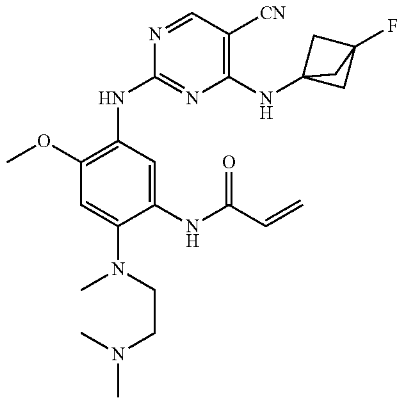 [SMILES: C=CC(=O)Nc1cc(Nc2ncc(C#N)c(NC34CC(F)(C3)C4)n2)c(OC)cc1N(C)CCN(C)C]

-continued
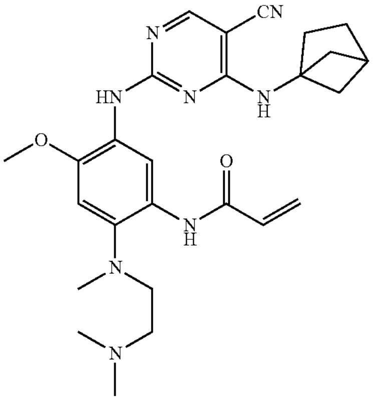 [SMILES: C=CC(=O)Nc1cc(Nc2ncc(C#N)c(NC34CCC(C3)C4)n2)c(OC)cc1N(C)CCN(C)C]
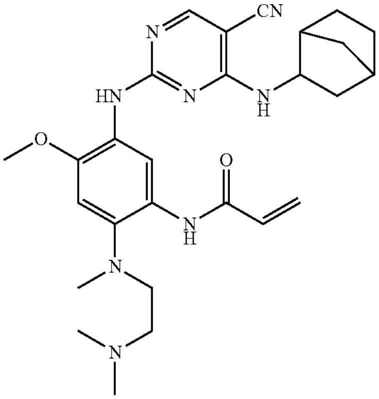 [SMILES: C=CC(=O)Nc1cc(Nc2ncc(C#N)c(NC3CC4CCC3C4)n2)c(OC)cc1N(C)CCN(C)C]
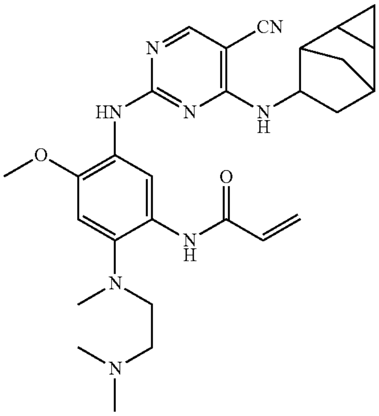 [SMILES: C=CC(=O)Nc1cc(Nc2ncc(C#N)c(NC3CC4CC3C3CC43)n2)c(OC)cc1N(C)CCN(C)C]
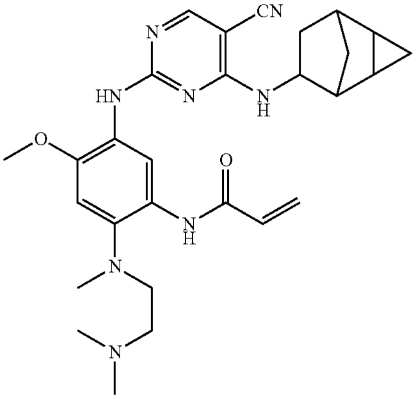
-continued
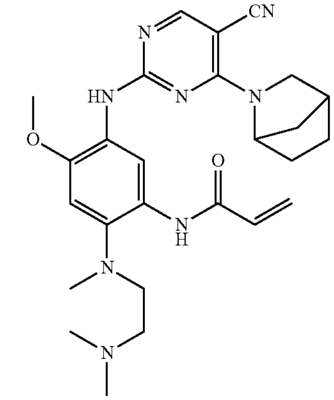
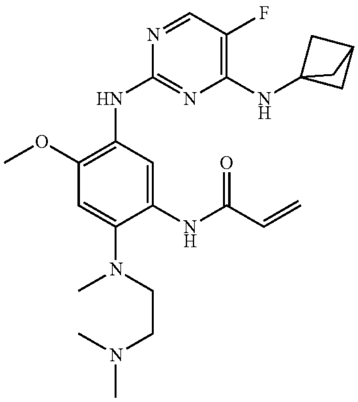
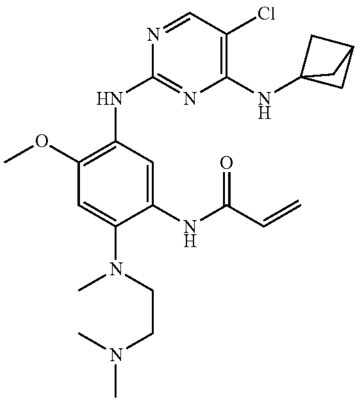
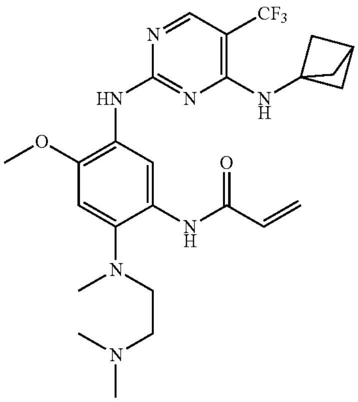

-continued
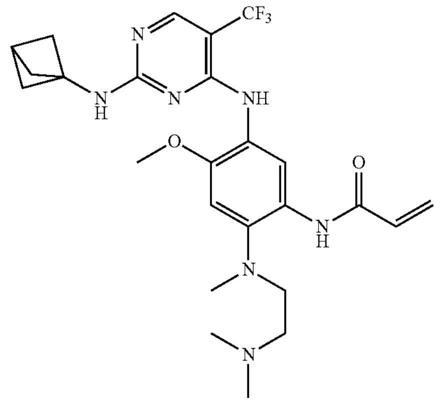
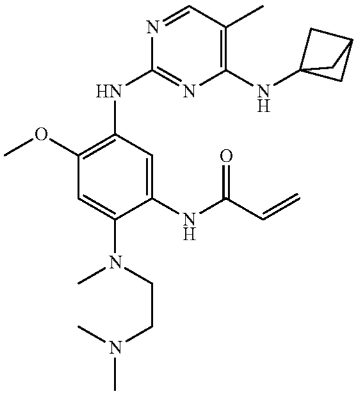
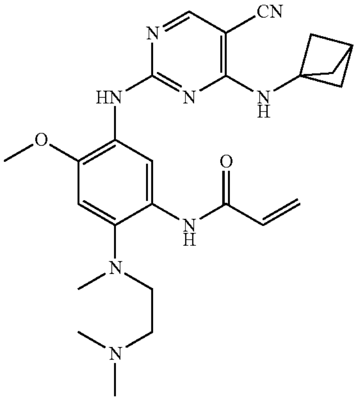
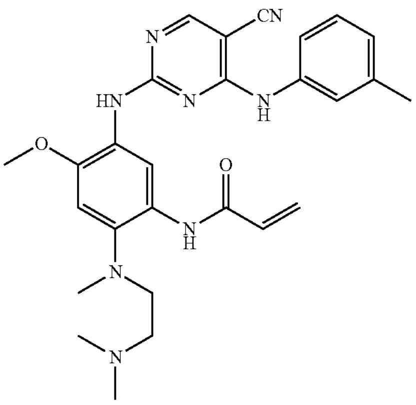
-continued
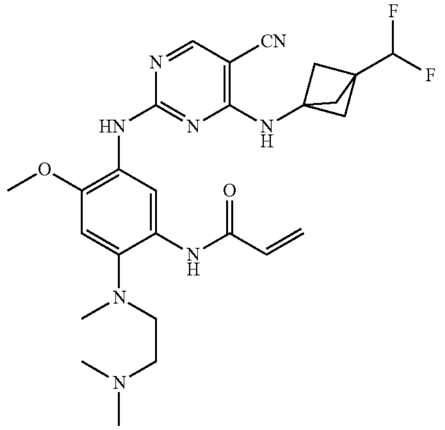
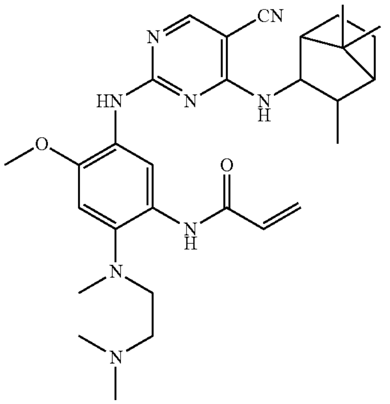
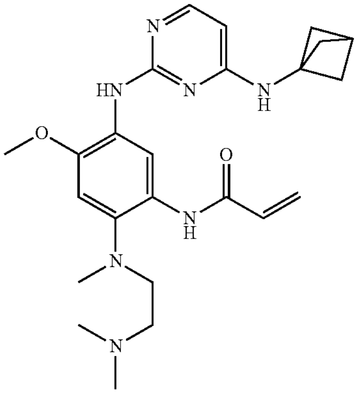
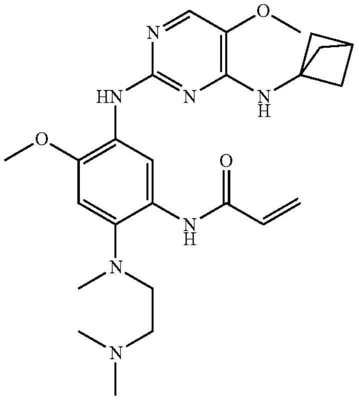

-continued
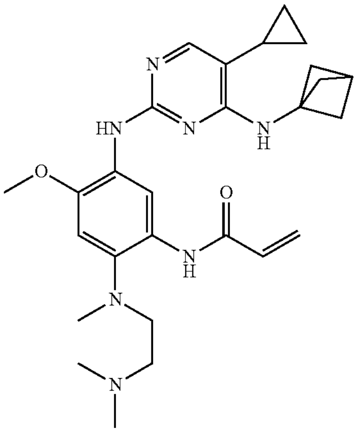
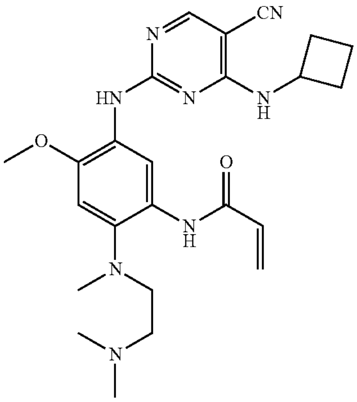
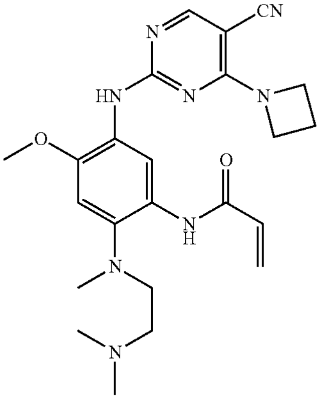
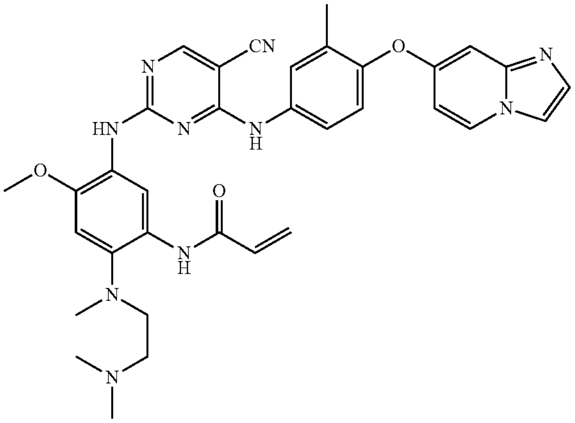
-continued
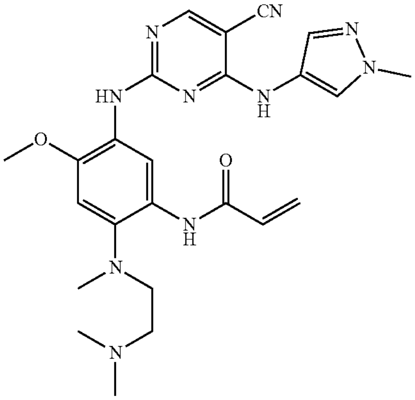
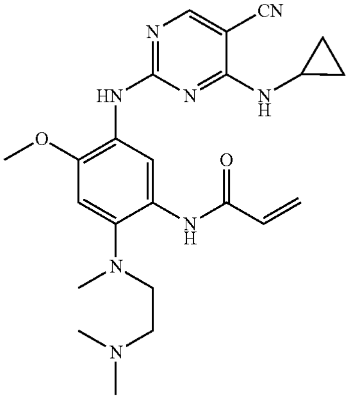
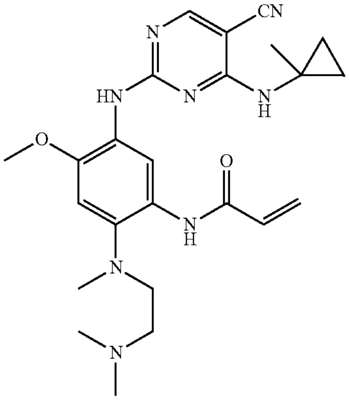
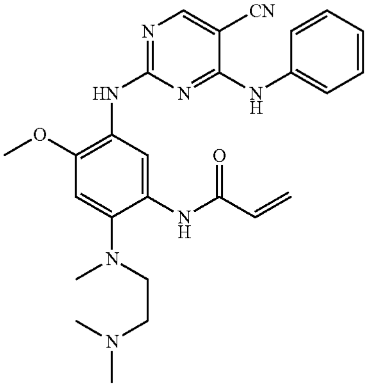

-continued
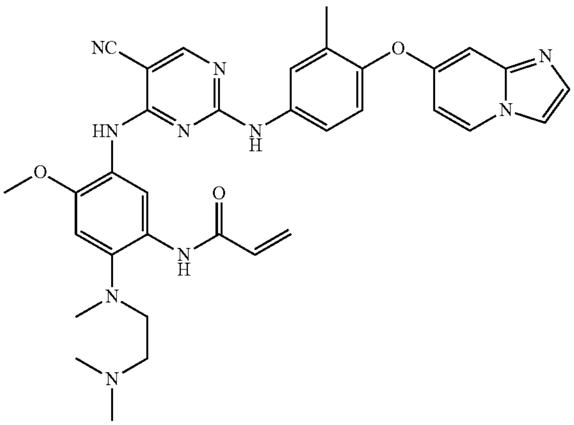
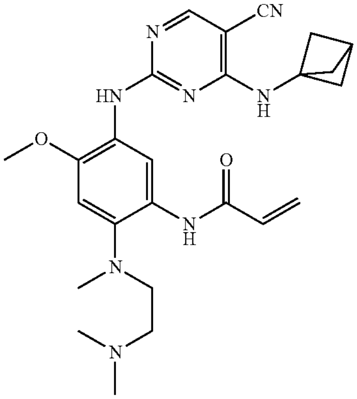
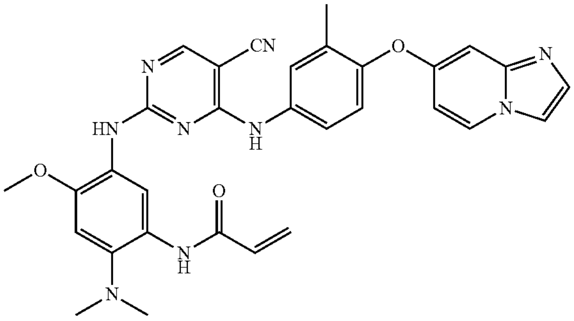
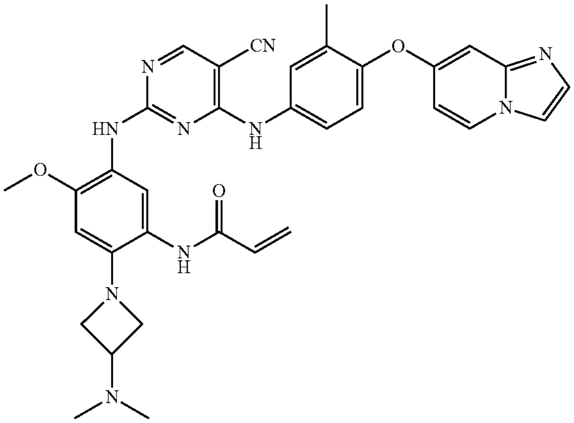
-continued
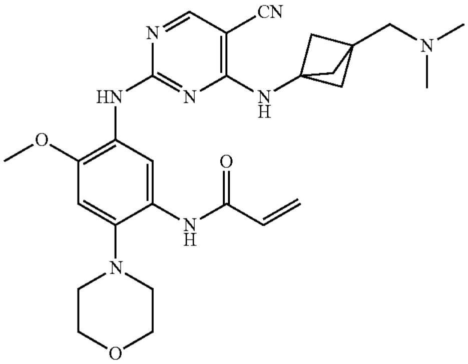
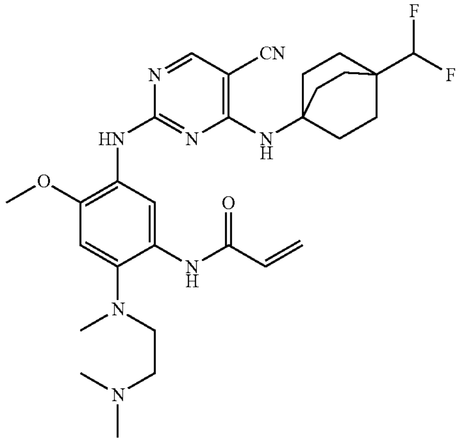
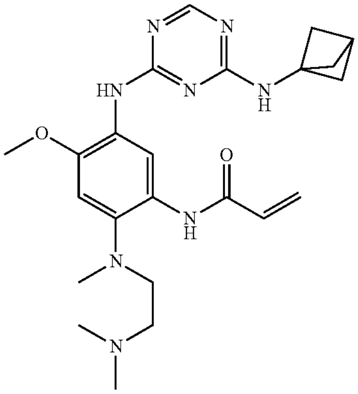
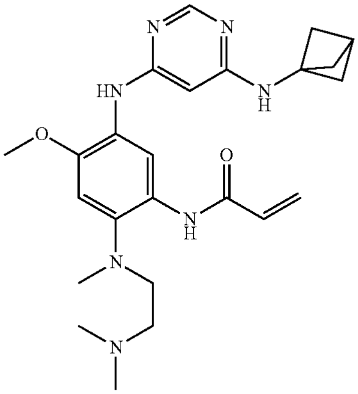

-continued
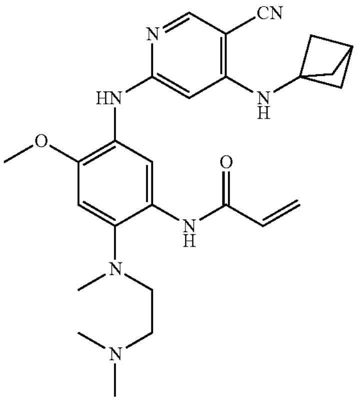
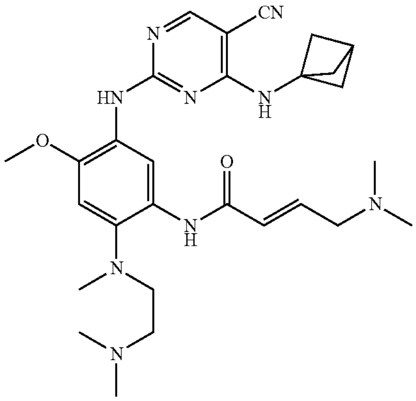
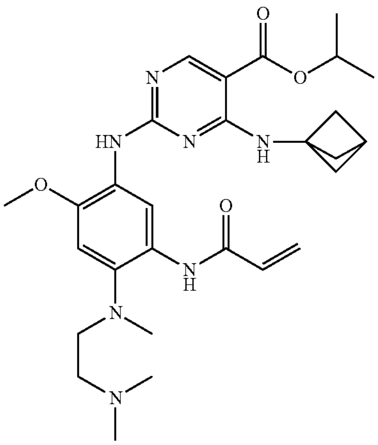
or a pharmaceutically acceptable salt thereof.
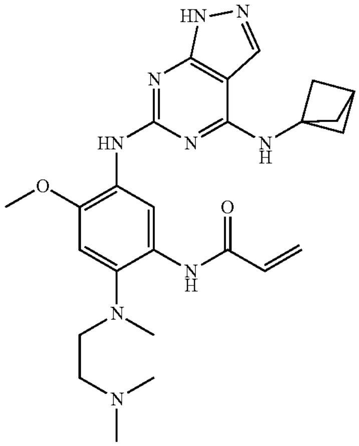
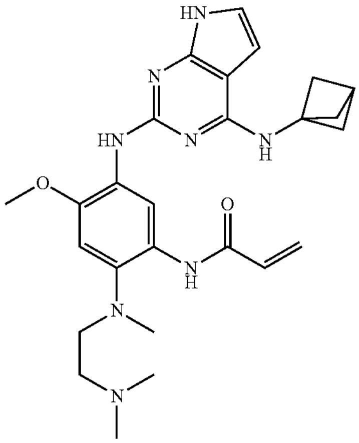
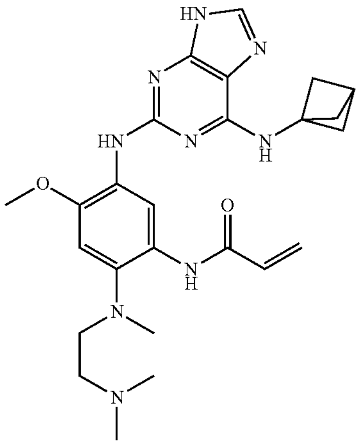
In another embodiment, the compound of Formula X is selected from the group consisting of -continued

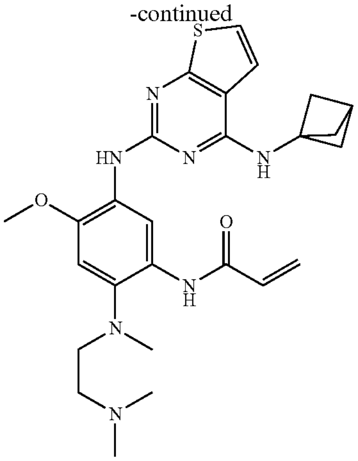

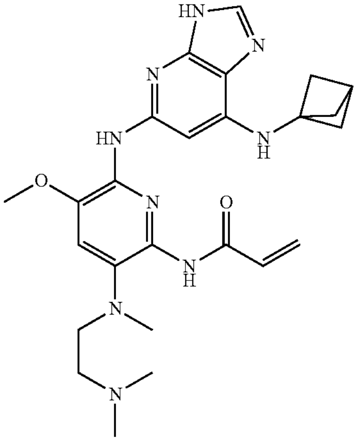

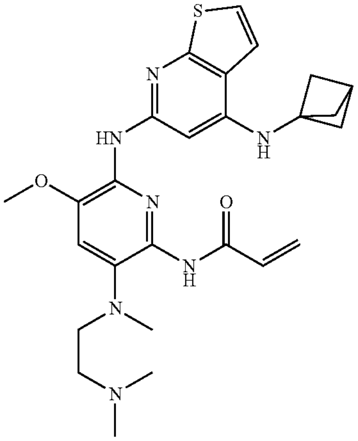

or a pharmaceutically acceptable salt thereof.

In another aspect, provided herein are pharmaceutical compositions comprising any of the compounds described herein, or a pharmaceutically acceptable salt thereof, together with a pharmaceutically acceptable carrier.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In another embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, the compounds described herein include a $^{2}H$ (i.e., deuterium) isotope.

In still another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The compounds described herein can be asymmetric (e.g., having one or more stereocenters). All stereoisomers, such as enantiomers and diastereomers, are intended unless otherwise indicated.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

The specific compounds described herein, and other compounds encompassed by one or more of the formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry $4^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds of the invention can be used in a method of treating a disease or condition in a subject, said method comprising administering to the subject a compound of the invention, or a pharmaceutical composition comprising a compound of the invention.

In an aspect, provided herein are methods of treating cancer in an individual in need thereof, comprising administering to the individual a therapeutically effective amount of any of the compounds or compositions described herein. In an embodiment, the subject is human.

In an embodiment of the methods, the cancer is selected from the group consisting of lung cancer, colon cancer, breast cancer, endometrial cancer, and thyroid cancer. In another embodiment, the cancer is non-small cell lung cancer (NSCLC). In yet another embodiment, the cancer is characterized by an EGFR mutation. In still another embodiment, the cancer is characterized by an HER2 mutation. In an embodiment, the cancer is characterized by small deletions in exon 19. In another embodiment, the cancer is characterized by the L858R point mutation. In yet another embodiment, the cancer is characterized by in-frame insertions in exon 20.

In still another embodiment, the method comprises administering a second active agent. In another embodiment, the second active agent is selected from the group consisting of a MEK inhibitor, a PI3K inhibitor, and an mTor inhibitor. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osimertinib.

In still another aspect, provided herein are methods of inhibiting EGFR and/or HER2 in an individual in need thereof, comprising administering to the individual a therapeutically effective amount of any of the compounds or compositions described herein. In an embodiment, EGFR is characterized by in-frame insertions in exon 20. In another embodiment, HER2 is characterized by in-frame insertions in exon 20. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osimertinib.

In another aspect, provided herein are methods of selectively inhibiting EGFR and/or HER2 in a subject, comprising administering to the subject a compound or composition disclosed herein. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osimertinib.

In another aspect, provided herein are methods of inhibiting the activity of EGFR and/or HER2 in an individual in need thereof, comprising administering to the individual any of the compounds or compositions described herein. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osimertinib.

In yet another aspect, provided herein are methods of treating a disease mediated by EGFR and/or HER2 in an individual in need thereof, comprising administering to the individual any of the compounds or compositions described herein. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osimertinib.

In still another aspect, provided herein are methods of modulating EGFR activity in an individual in need thereof, comprising administering to the individual any of the compounds or compositions described herein. In an embodiment, the method comprises inhibiting or decreasing EGFR activity. In another embodiment, the method comprises modulating (e.g., inhibiting or decreasing) the activity of EGFR containing one or more mutations. In yet another embodiment, the mutant EGFR contains one or more mutations selected from T790M, L718Q, L844V, L858R, and Del. In still another embodiment, the mutant EGFR contains a combination of mutations, wherein the combination is selected from Del/L718Q, Del/L844V, De/T790M, Del/T790M/L718Q, Del/T790M/L844V, L858R/L718Q, L858R/L844V, L858R/T790M, and L858R/T790M/L718Q. In an embodiment, the mutant EGFR contains a combination of mutations, wherein the combination is selected from Del/L718Q, Del/L844V, Del/T790M, Del/T790M/L844V, L858R/L844V, and L858R/T790M. In one embodiment, the mutant EGFR contains a combination of mutations, wherein the combination is selected from L858R/T790M, Del/T790M, Del/T790M/L718Q, and L858R/T790M/L718Q. In another embodiment, the mutant EGFR is characterized by in-frame insertions in exon 20. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osimertinib.

In one embodiment, the method comprises modulating (e.g., inhibiting or decreasing) the activity of EGFR containing one or more mutations, but do not affect the activity of a wild-type EGFR. In one embodiment, the method further comprises administering to the subject a second active agent, wherein said second active agent prevents EGFR dimer formation. In another embodiment, the method further comprises an ATP competitive EGFR inhibitor. In another embodiment, the ATP competitive EGFR inhibitor is osimertinib.

Modulation of EGFR containing one or more mutations, such as those described herein, but not a wild-type EGFR, provides a novel approach to the treatment, prevention, or amelioration of diseases including, but not limited to, cancer and metastasis, inflammation, arthritis, systemic lupus erythematosus, skin-related disorders, pulmonary disorders, cardiovascular disease, ischemia, neurodegenerative disorders, liver disease, gastrointestinal disorders, viral and bacterial infections, central nervous system disorders, Alzheimer's disease, Parkinson's disease, Huntington's disease, amyotrophic lateral sclerosis, spinal cord injury, and peripheral neuropathy.

In one embodiment, the compounds described herein exhibit greater inhibition of EGFR containing one or more mutations as described herein relative to a wild-type EGFR. In certain embodiments, the compounds provided herein exhibit at least 2-fold, 3-fold, 5-fold, 10-fold, 25-fold, 50-fold or 100-fold greater inhibition of EGFR containing one or more mutations as described herein relative to a wild-type EGFR. In various embodiments, the compounds provided herein exhibit up to 1000-fold greater inhibition of EGFR containing one or more mutations as described herein relative to a wild-type EGFR. In various embodiments, the compounds provided herein exhibit up to 10000-fold greater inhibition of EGFR having a combination of mutations selected from L858R/T790M, Del/T790M, Del/T790M/L718Q, and L858R/T790M/L718Q relative to a wild-type EGFR.

In various embodiments, the compounds of the invention exhibit from about 2-fold to about 10-fold greater inhibition of EGFR containing one or more mutations as described herein relative to a wild-type EGFR. In various embodiments, the compounds of the invention exhibit from about 10-fold to about 100-fold greater inhibition of EGFR containing one or more mutations as described herein relative to a wild-type EGFR. In various embodiments, the compounds provided herein exhibit from about 100-fold to about 1000-fold greater inhibition of EGFR containing one or more mutations as described herein relative to a wild-type EGFR. In various embodiments, the compounds provided herein exhibit from about 1000-fold to about 10000-fold greater inhibition of EGFR containing one or more mutations as described herein relative to a wild-type EGFR.

In certain embodiments, the compounds provided herein exhibit at least 2-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds provided herein exhibit at least 3-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds provided herein exhibit at least 5-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds provided herein exhibit at least 10-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds provided herein exhibit at least 25-fold greater inhibition of EGFR having a combination of mutations selected from L858R/T790M, Del/T790M, Del/T790M/L718Q, and L858R/T790M/L718Q relative to a wild-type EGFR. In certain embodiments, the compounds provided herein exhibit at least 50-fold greater inhibition of EGFR having a combination of mutations selected from L858R/T790M, De/T790M, Del/T790M/L718Q, and L858R/T790M/L718Q relative to a wild-type EGFR. In certain embodiments, the compounds provided herein exhibit at least 100-fold greater inhibition of EGFR having a combination of mutations selected from L858R/T790M, Del/T790M, Del/T790M/L718Q, and L858R/T790M/L718Q relative to a wild-type EGFR.

In some embodiments, the inhibition of EGFR activity is measured by $IC_{50}$.

In some embodiments, the inhibition of EGFR activity is measured by $EC_{50}$.

In some embodiments, the compounds of the invention covalently modify Cysteine 797 in EGFR.

In some embodiments, the invention provides a compound comprising an irreversible kinase inhibitor, wherein the compound is a more potent inhibitor of a drug-resistant EGFR mutant relative to a wild type EGFR. For example, the compound can be at least about 2-fold, 3-fold, 5-fold, 10-fold, 25-fold, 50-fold or about 100-fold more potent at inhibiting the kinase activity of the drug-resistant EGFR mutant relative to a wild-type EGFR. In some embodiments, the drug-resistant EGFR mutant is resistant to one or more known EGFR inhibitors, including but not limited to gefitinib, erlotinib, lapatinib, WZ4002, HKI-272, CL-387785 (EKI-785), and osimertinib.

In an embodiment, the compounds provided herein are irreversible kinase inhibitors, wherein the compound inhibits kinase activity of a drug-resistant EGFR mutant harboring a sensitizing mutation (e.g., Del and L858R) and a drug-resistance mutation (e.g., T790M, L718Q, and L844V) with less than a 10-fold difference in potency (e.g., as measured by $IC_{50}$) relative to an EGFR mutant harboring the sensitizing mutation but not the drug-resistance mutation. In some embodiments, the difference in potency is less than about 9-fold, 8-fold, 7-fold, 6-fold, 5-fold, 4-fold, 3-fold, or 2-fold.

In another embodiment, the compounds provided herein are irreversible kinase inhibitors, wherein the compound is more potent than one or more known EGFR inhibitors, including but not limited to gefitinib, erlotinib, lapatinib, WZ4002, HKI-272, CL-387,785, and osimertinib, at inhibiting the activity of EGFR containing one or more mutations as described herein, such as T790M, L718Q, L844V, L858R, and Del. For example, the compound can be at least about 2-fold, 3-fold, 5-fold, 10-fold, 25-fold, 50-fold or about 100-fold more potent (e.g., as measured by $IC_{50}$) than gefitinib, erlotinib, lapatinib, WZ4002, HKI-272, CL-387,785, and osimertinib at inhibiting the activity of the EGFR containing one or more mutations as described herein.

In yet another embodiment, the compounds provided herein are irreversible kinase inhibitors, wherein the compound is less potent than one or more known EGFR inhibitors, including but not limited to gefitinib, erlotinib, lapatinib, WZ4002, HKI-272, CL-387,785, and osimertinib, at inhibiting the activity of a wild-type EGFR. For example, the compound can be at least about 2-fold, 3-fold, 5-fold, 10-fold, 25-fold, 50-fold or about 100-fold less potent (e.g., as measured by $IC_{50}$) than gefitinib, erlotinib, lapatinib, WZ4002, HKI-272, CL-387,785, and osimertinib, at inhibiting the activity of a wild-type EGFR.

Potency of the inhibitor can be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an EGFR-dependent phosphorylation level in 3T3 cells expressing a wild type EGFR, a mutant EGFR, or a fragment of any thereof.

An EGFR sensitizing mutation comprises without limitation L858R, G719S, G719C, G719A, L861Q, a deletion in exon 19 and/or an insertion in exon 20. A drug-resistant EGFR mutant can have without limitation a drug resistance mutation comprising T790M, T854A, L718Q or D761Y.

The selectivity between wild-type EGFR and EGFR containing one or more mutations as described herein can also be measured using cellular proliferation assays where cell proliferation is completely dependent on kinase activity. For example, murine Ba/F3 cells transfected with a suitable version of wild-type EGFR (containing a WT EGFR kinase domain), or Ba/F3 cells transfected with L858R/T790M, Del/T790M/L718Q, L858R/T790M/L718Q or Exon 19 deletion/T790M can be used. Proliferation assays are performed at a range of inhibitor concentrations (10 μM, 3 μM, 1.1 μM, 330 nM, 110 nM, 33 nM, 11 nM, 3 nM, 1 nM) and an $EC_{50}$ is calculated.

An alternative method to measure effects on EGFR activity is to assay EGFR phosphorylation. Wild type or mutant (L858R/T790M, Del/T790M, Del/T790M/L718Q, or L858R/T790M/L718Q) EGFR can be transfected into NIH-3T3 cells (which do not normally express endogenous EGFR) and the ability of the inhibitor (using concentrations as above) to inhibit EGFR phosphorylation can be assayed. Cells are exposed to increasing concentrations of inhibitor for 6 hours and stimulated with EGF for 10 minutes. The effects on EGFR phosphorylation are assayed by Western Blotting using phospho-specific (Y1068) EGFR antibodies.

In another aspect, provided herein are compounds that covalently modify Cysteine 797 in EGFR, wherein the compound exhibits greater than 2-fold, 3-fold, 5-fold, 10-fold, 25-fold, 50-fold, 100-fold, or 1000-fold inhibition of EGFR containing one or more mutations as described herein (e.g., L858R/T790M, Del/T790M, Del/T790M/L718Q, or L858R/T790M/L718Q) relative to a wild-type EGFR.

In another aspect, the application provides a method of inhibiting a kinase, comprising contacting the kinase with a compound disclosed herein, or a pharmaceutically acceptable salt, hydrate, solvate, or stereoisomer thereof. In some embodiments, the kinase comprises a mutated cysteine residue. In further embodiments, the mutated cysteine residue is located in or near the position equivalent to Cys 797 in EGFR, including such position in Jak3, Blk, Bmx, Btk, HER2 (ErbB2), HER4 (ErbB4), Itk, Tec, and Txk. In some embodiments, the kinase is EGFR. In some embodiments, the kinase is a Her-kinase. In other embodiments, the method further comprises a second agent that prevents kinase dimer formation. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In another aspect, provided herein are methods of inhibiting a kinase, the method comprising administering to a subject in need thereof an effective amount of a compound disclosed herein, or a pharmaceutically acceptable salt, hydrate, solvate, or stereoisomer thereof.

In some embodiments, the kinase is EGFR. In some embodiments, the kinase is a Her-kinase. In other embodiments, the method further comprises administering a second agent that prevents dimer formation of the kinase. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In still another aspect, provided herein are methods of inhibiting EGFR, the method comprising administering to a subject in need thereof an effective amount of a compound disclosed herein, or a pharmaceutically acceptable salt, hydrate, solvate, or stereoisomer thereof.

In some embodiments, the method further comprises administering a second agent that prevents EGFR dimer formation. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab.

In another aspect, provided herein are methods of treating or preventing a disease, the method comprising administering to a subject in need thereof an effective amount of a compound disclosed herein, or a pharmaceutically acceptable salt, hydrate, solvate, or stereoisomer thereof. In some embodiments, the disease is mediated by a kinase. In further embodiments, the kinase comprises a mutated cysteine residue. In further embodiments, the mutated cysteine residue is located in or near the position equivalent to Cys 797 in EGFR, including such positions in Jak3, Blk, Bmx, Btk, HER2 (ErbB2), HER4 (ErbB4), Itk, Tec, and Txk. In some embodiments, the method further comprises administering a second agent that prevents dimer formation of the kinase. In some embodiments, the second agent that prevents kinase dimer formation is an antibody. In further embodiments, the second agent prevents EGFR dimer formation. In further embodiments, the second agent that prevents EGFR dimer formation is cetuximab, trastuzumab, or panitumumab. In further embodiments, the second agent that prevents EGFR dimer formation is cetuximab.

In some embodiments, the disease is mediated by EGFR (e.g., EGFR plays a role in the initiation or development of the disease). In further embodiments, the EGFR is a Her-kinase. In further embodiments, the Her-kinase is HER1, HER2, or HER4. In some embodiments, the EGFR comprises one or more mutations, as described herein.

In certain embodiments, the disease is cancer or a proliferation disease.

In further embodiments, the disease is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

In other embodiments, the disease is inflammation, arthritis, rheumatoid arthritis, spondyloarthropathies, gouty arthritis, osteoarthritis, juvenile arthritis, and other arthritic conditions, systemic lupus erythematosus (SLE), skin-related conditions, psoriasis, eczema, burns, dermatitis, neuroinflammation, allergy, pain, neuropathic pain, fever, pulmonary disorders, lung inflammation, adult respiratory distress syndrome, pulmonary sarcoidosis, asthma, silicosis, chronic pulmonary inflammatory disease, and chronic obstructive pulmonary disease (COPD), cardiovascular disease, arteriosclerosis, myocardial infarction (including post-myocardial infarction indications), thrombosis, congestive heart failure, cardiac reperfusion injury, as well as complications associated with hypertension and/or heart failure such as vascular organ damage, restenosis, cardiomyopathy, stroke including ischemic and hemorrhagic stroke, reperfusion injury, renal reperfusion injury, ischemia including stroke and brain ischemia, and ischemia resulting from cardiac/coronary bypass, neurodegenerative disorders, liver disease and nephritis, gastrointestinal conditions, inflammatory bowel disease, Crohn's disease, gastritis, irritable bowel syndrome, ulcerative colitis, ulcerative diseases, gastric ulcers, viral and bacterial infections, sepsis, septic shock, gram negative sepsis, malaria, meningitis, HIV infection, opportunistic infections, cachexia secondary to infection or malignancy, cachexia secondary to acquired immune deficiency syndrome (AIDS), AIDS, ARC (AIDS related complex), pneumonia, herpes virus, myalgias due to infection, influenza, autoimmune disease, graft vs. host reaction and allograft rejections, treatment of bone resorption diseases, osteoporosis, multiple sclerosis, cancer, leukemia, lymphoma, colorectal cancer, brain cancer, bone cancer, epithelial call-derived neoplasia (epithelial carcinoma), basal cell carcinoma, adenocarcinoma, gastrointestinal cancer, lip cancer, mouth cancer, esophageal cancer, small bowel cancer, stomach cancer, colon cancer, liver cancer, bladder cancer, pancreas cancer, ovarian cancer, cervical cancer, lung cancer, breast cancer, skin cancer, squamous cell and/or basal cell cancers, prostate cancer, renal cell carcinoma, and other known cancers that affect epithelial cells throughout the body, chronic myelogenous leukemia (CML), acute myeloid leukemia (AML) and acute promyelocytic leukemia (APL), angiogenesis including neoplasia, metastasis, central nervous system disorders, central nervous system disorders having an inflammatory or apoptotic component, Alzheimer's disease, Parkinson's disease, Huntington's disease, amyotrophic lateral sclerosis, spinal cord injury, and peripheral neuropathy, or B-Cell Lymphoma.

In further embodiments, the disease is inflammation, arthritis, rheumatoid arthritis, spondyloarthropathies, gouty arthritis, osteoarthritis, juvenile arthritis, and other arthritic conditions, systemic lupus erythematosus (SLE), skin-related conditions, psoriasis, eczema, dermatitis, pain, pulmonary disorders, lung inflammation, adult respiratory distress syndrome, pulmonary sarcoidosis, asthma, chronic pulmonary inflammatory disease, and chronic obstructive pulmonary disease (COPD), cardiovascular disease, arteriosclerosis, myocardial infarction (including post-myocardial infarction indications), congestive heart failure, cardiac reperfusion injury, inflammatory bowel disease, Crohn's disease, gastritis, irritable bowel syndrome, leukemia or lymphoma.

In another aspect, provided herein are methods of treating a kinase mediated disorder, the method comprising administering to a subject in need thereof an effective amount of a compound disclosed herein, or a pharmaceutically acceptable salt, hydrate, solvate, or stereoisomer thereof. In other embodiments, the compound is an inhibitor of HER1, HER2, or HER4. In other embodiments, the subject is administered an additional therapeutic agent. In other embodiments, the compound and the additional therapeutic agent are administered simultaneously or sequentially.

In another aspect, provided herein are methods of treating a kinase mediated disorder, the method comprising administering to a subject in need thereof an effective amount of a compound disclosed herein, or a pharmaceutically acceptable salt, hydrate, solvate, or stereoisomer thereof, and a second agent that prevents EGFR dimer formation. In other embodiments, the compound is an inhibitor of HER1, HER2, or HER4. In other embodiments, the subject is administered an additional therapeutic agent. In other embodiments, the compound, the second agent that prevents EGFR dimer formation, and the additional therapeutic agent are administered simultaneously or sequentially. In some embodiments, the second agent that prevents EGFR dimer formation is an antibody. In further embodiments, the second agent that prevents EGFR dimer formation is cetuximab, trastuzumab, or panitumumab. In further embodiments, the second agent that prevents EGFR dimer formation is cetuximab. In further embodiments, the second agent that prevents EGFR dimer formation is osimertinib.

In other embodiments, the disease is cancer. In further embodiments, the cancer is lung cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors.

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as corn-starch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth.

EXAMPLES

The invention is further illustrated by the following examples, which should not be construed as further limiting. The practice of the present invention will employ, unless otherwise indicated, conventional techniques of organic synthesis, cell biology, cell culture, and molecular biology, which are within the skill of the art.

Abbreviations

ACN acetonitrile
AcOH acetic acid
BnOH benzyl alcohol
BuOH butanol
DAST diethylaminosulfur trifluoride
dba dibenzylideneacetone
DCM dichloromethane
DIEA/DIPEA diisopropylethylamine
DMF dimethylformamide
DMSO dimethylsulfoxide
DPPA diphenylphosphoryl azide
DPPF 1,1'-ferrocenediyl-bis(diphenylphosphine)
$Et_2O$ diethyl ether
EtOAc/EA ethyl acetate
FA formic acid
iPrOH isopropanol
MeOH methanol
PCC pyridinium chlorochromate
PE petroleum ether
PrOH propanol
pTsOH p-toluenesulfonic acid
TEA triethylamine
TFA trifluoroacetic acid
THF tetrahydrofuran
Xantphos 4,5-bis(diphenylphosphino)-9,9-dimethylxanthene

Example 1—Synthetic Procedures

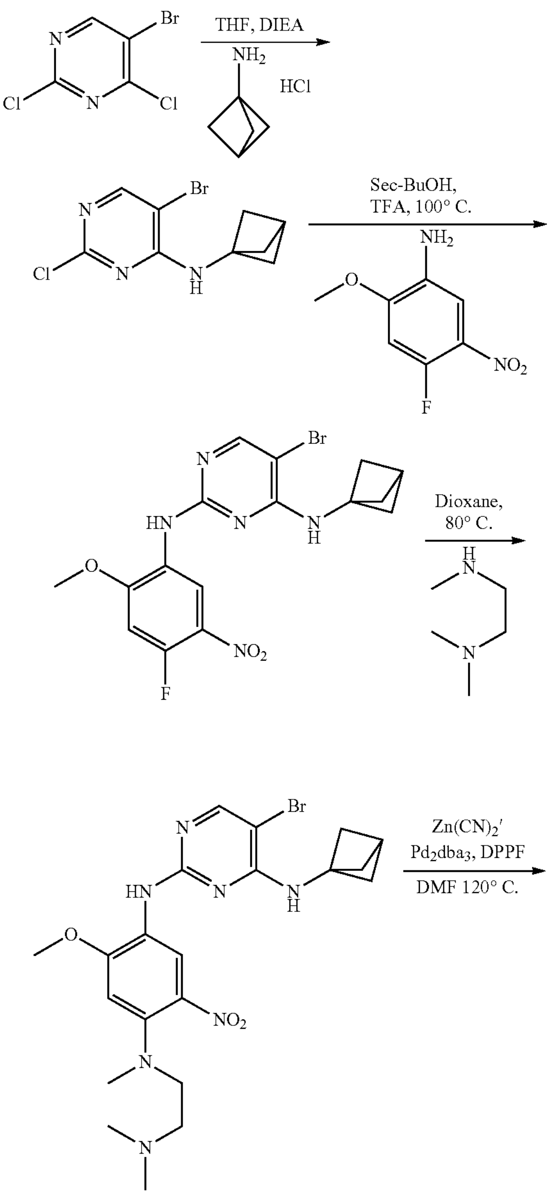

-continued

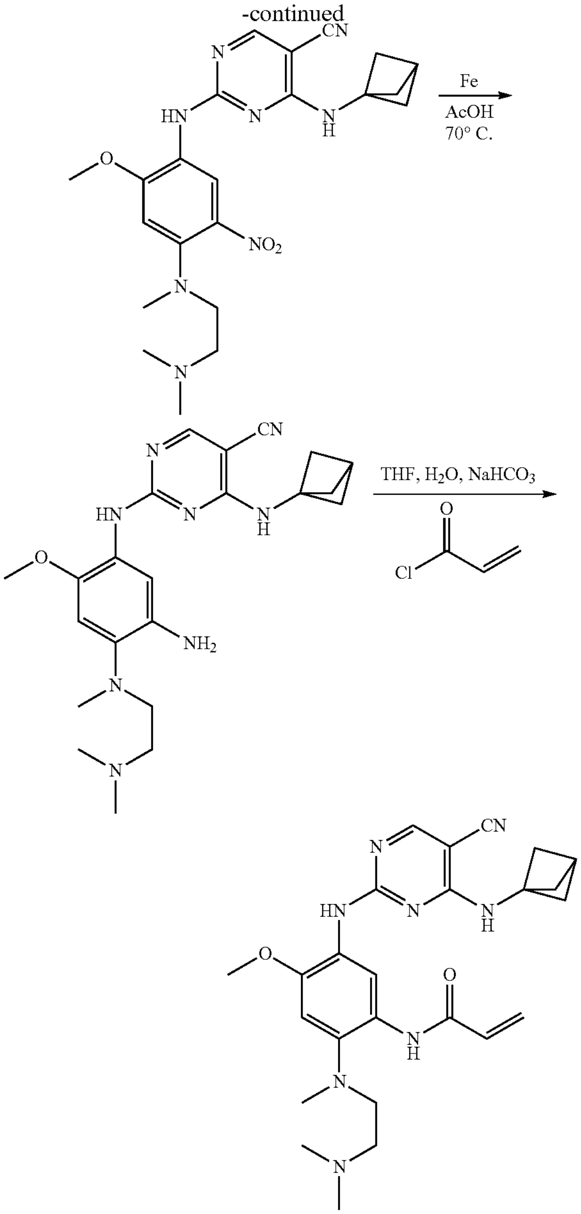

013

N-(bicyclo[1.1.1]pentan-1-yl)-5-bromo-2-chloropyrimidin-4-amine

To a solution of 5-bromo-2,4-dichloropyrimidine (500 mg, 2.19 mmol) in THF (5 mL) was added bicyclo[1.1.1]pentan-1-amine HCl (629 mg, 2.63 mmol) followed by DIEA (1.14 mL, 6.57 mmol). The mixture was stirred for 4 hours at rt and then quenched with $H_2O$ and extracted with EtOAc. The combined organic layers were washed with $H_2O$, Brine, dried over $MgSO_4$ and condensed to give the desired product as a clear oil that was used without further purification. (ESI) m/z: 276.41 $(M+H)^+$ N4-(bicyclo[1.1.1]pentan-1-yl)-5-bromo-N2-(4-fluoro-2-methoxy-5-nitrophenyl)-pyrimidine-2,4-diamine To a solution of N-(bicyclo[1.1.1]pentan-1-yl)-5-bromo-2-chloropyrimidin-4-amine (300 mg, 1.09 mmol) in Sec-BuOH (8 mL) was added 4-fluoro-2-methoxy-5-nitroaniline (488 mg, 2.62 mmol) along with TFA (1 mL). The mixture was stirred at 100° C. for 4 hours, cooled to rt and then poured into diethyl ether (100 mL). The resulting precipitate was filtered and rinsed with diethyl ether (300 mL) to remove excess 4-fluoro-2-methoxy-5-nitroaniline. The resulting solid was dried under $N_2$ to give a beige solid that was used without further purification (260 mg). (ESI) m/z: 425.78 $(M+H)^+$ N4-(bicyclo[1.1.1]pentan-1-yl)-5-bromo-N2-(4-((2-(dimethylamino)ethyl)methyl)amino)-2-methoxy-5-nitrophenyl)pyrimidine-2,4-diamine To a solution of N4-(bicyclo[1.1.1]pentan-1-yl)-5-bromo-N2-(4-fluoro-2-methoxy-5-nitrophenyl)pyrimidine-2,4-diamine (260 mg, 0.613 mmol) in 1,4-dioxane (8 mL) was added N1,N1,N2-trimethylethane-1,2-diamine (500 mg, 4.9 mmol). The mixture was stirred at 80° C. for 2 hours and then quenched with $H_2O$ and extracted with EtOAc. The combined organic layers were washed with $H_2O$, Brine, dried over $MgSO_4$ and condensed to give the desired product as an orange-brown oil that was used without further purification (310 mg). (ESI) m/z: 508.24 $(M+H)^+$ 4-(bicyclo[1.1.1]pentan-1-ylamino)-2-((4-((2-(dimethylamino)ethyl)methyl)amino)-2-methoxy-5-nitrophenyl)amino)pyrimidine-5-carbonitrile To a solution of N4-(bicyclo[1.1.1]pentan-1-yl)-5-bromo-N2-(4-((2-(dimethylamino)ethyl)(methyl)amino)-2-methoxy-5-nitrophenyl)pyrimidine-2,4-diamine (310 mg, 0.592 mmol) in DMF (6 mL) was added $Zn(CN)_2$ (153 mg, 1.303 mmol). The mixture was thoroughly degassed using sonication. $Pd_2dba_3$ (65 mg, 0.071 mmol) and DPPF (79 mg, 0.142 mmol) were added and the vial flushed with $N_2$ and sealed. The mixture was stirred at 120° C. for 2 hours. The mixture was filtered through celite washing with EtOAc. The resulting solution was washed with $H_2O$, Brine, dried over $MgSO_4$ and condensed to give the desired product as a brown oil that was used without further purification (300 mg). (ESI) m/z: 453.65 $(M+H)^+$ 2-((5-amino-4-((2-(dimethylamino)ethyl)(methyl)amino)-2-methoxyphenyl)amino)-4-(bicyclo[1.1.1]pentan-1-ylamino)pyrimidine-5-carbonitrile To a solution of 4-(bicyclo[1.1.1]pentan-1-ylamino)-2-((4-((2-(dimethylamino)ethyl)-(methyl)amino)-2-methoxy-5-nitrophenyl)amino)pyrimidine-5-carbonitrile (300 mg, 0.664 mmol) in AcOH (8 mL) was added Fe powder (371 mg, 6.63 mmol). The mixture was stirred at 70° C. for 2 hours, cooled to rt and the solvent removed under vacuum. The resulted residue was suspended in EtOAc and washed with sat. aq. $NaHCO_3$ and filtered through celite. The resulting solution was washed with $H_2O$, Brine, dried over $MgSO_4$ and condensed to give the desired product as a brown oil that was used without further purification (300 mg). (ESI) m/z: 423.58 $(M+H)^+$ Compound 013: N-(5-((4-(bicyclo[1.1.1]pentan-1-ylamino)-5-cyanopyrimidin-2-yl)amino)-2-((2-(dimethylamino)ethyl)(methyl)amino)-4-methoxyphenyl)acrylamide To a solution of 2-((5-amino-4-((2-(dimethylamino)ethyl)(methyl)amino)-2-methoxyphenyl)amino)-4-(bicyclo[1.1.1]

pentan-1-ylamino)pyrimidine-5-carbonitrile (300 mg, 0.71 mmol) in a 1:1 mixture of THF and sat. aq. $NaHCO_3$ (8 mL) was added acryloyl chloride (69 μL). The mixture was stirred for 20 minutes, then quenched with $H_2O$ and extracted with EtOAc. The combined organic layers were washed with $H_2O$, Brine, dried over $MgSO_4$ and condensed to give the desired product as a brown oil that was purified by reverse phase HPLC using a gradient of 1 to 70% ACN in $H_2O$ with 0.035% TFA to give the desired product as a white solid. (ESI) m/z: 477.31 $(M+H)^+$ The subsequent compounds were prepared following the protocol in Scheme 1.

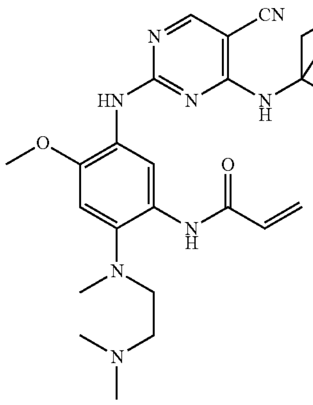

Compound 001: N-(5-((4-(bicyclo[2.2.2]octan-1-ylamino)-5-cyanopyrimidin-2-yl)amino)-2-((2-(dimethylamino)ethyl)(methyl)amino)-4-methoxyphenyl) acrylamide (ESI) m/z: 419.83 $(M+H)^+$

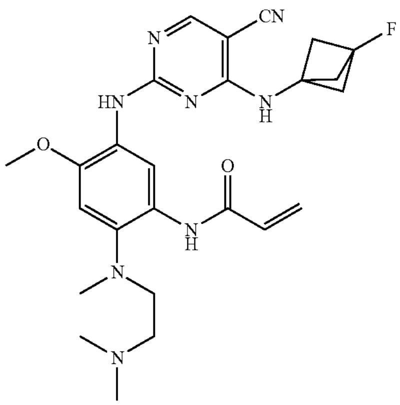

Compound 002: N-(5-((5-cyano-4-((3-fluorobicyclo[1.1.1]pentan-1-yl)amino)pyrimidin-2-yl)amino)-2-((2-(dimethylamino)ethyl)(methyl)amino)-4-methoxyphenyl)acrylamide (ESI) m/z 495.38 $(M+H)^+$

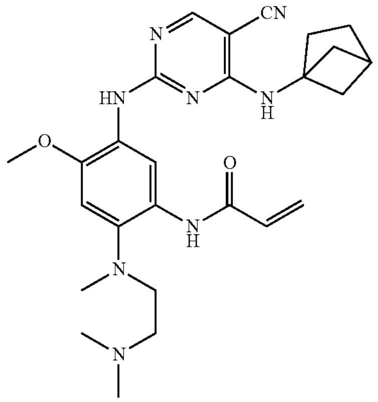

Compound 003: N-(5-((4-(bicyclo[2.1.1]hexan-1-ylamino)-5-cyanopyrimidin-2-yl)amino)-2-((2-(dimethylamino)ethyl)(methyl)amino)-4-methoxyphenyl) acrylamide (ESI) m/z: 492.19 $(M+H)^+$

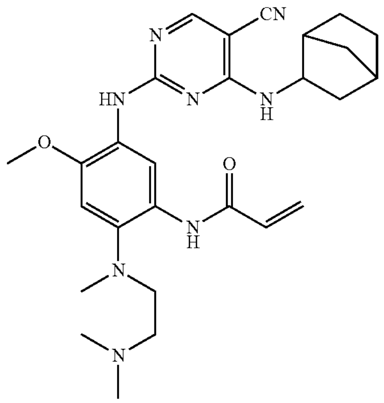

Compound 004: N-(5-((4-(bicyclo[2.2.1]heptan-2-ylamino)-5-cyanopyrimidin-2-yl)amino)-2-((2-(dimethylamino)ethyl)(methyl)amino)-4-methoxyphenyl) acrylamide (ESI) m/z: 505.49 $(M+H)^+$

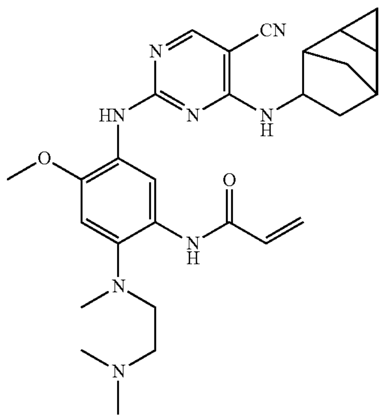

Compound 005: N-(5-((5-cyano-4-(tricyclo[3.2.1.02,4]octan-6-ylamino)pyrimidin-2-yl)amino)-2-((2-(dimethylamino)ethyl)(methyl)amino)-4-methoxyphenyl)acrylamide (ESI) m/z: 517.29 $(M+H)^+$

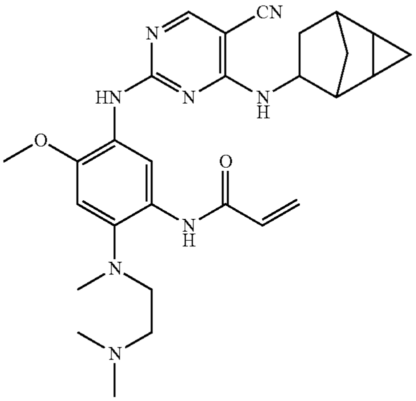 [SMILES: C=CC(=O)Nc1cc(Nc2ncc(C#N)c(NC3CC4CC3C3CC43)n2)c(OC)cc1N(C)CCN(C)C]

Compound 006: N-(5-((5-cyano-4-(tricyclo[3.2.1.02,4]octan-6-ylamino)pyrimidin-2-yl)amino)-2-((2-(dimethylamino)ethyl)(methyl)amino)-4-methoxyphenyl)acrylamide (ESI) m/z: 517.37 $(M+H)^+$

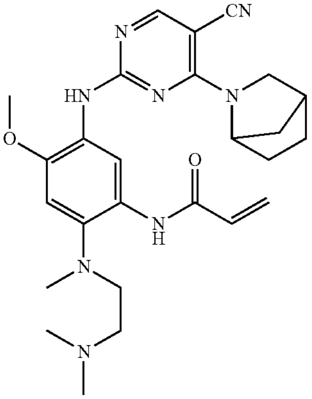 [SMILES: C=CC(=O)Nc1cc(Nc2ncc(C#N)c(N3CC4CCC3C4)n2)c(OC)cc1N(C)CCN(C)C]

Compound 007: N-(5-((4-(2-azabicyclo[2.2.1]heptan-2-yl)-5-cyanopyrimidin-2-yl)amino)-2-((2-(dimethylamino)ethyl)(methyl)amino)-4-methoxyphenyl) acrylamide (ESI) m/z: 491.62 $(M+H)^+$

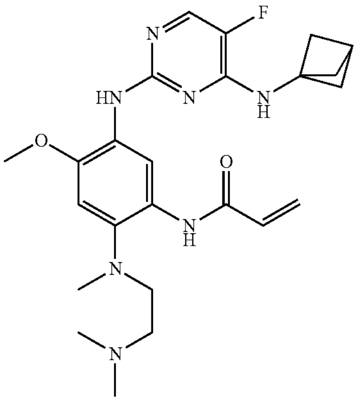

Compound 008: N-(5-((4-(bicyclo[1.1.1]pentan-1-ylamino)-5-fluoropyrimidin-2-yl)amino)-2-((2-(dimethylamino)ethyl)(methyl)amino)-4-methoxyphenyl) acrylamide (ESI) m/z: 470.81 $(M+H)^+$

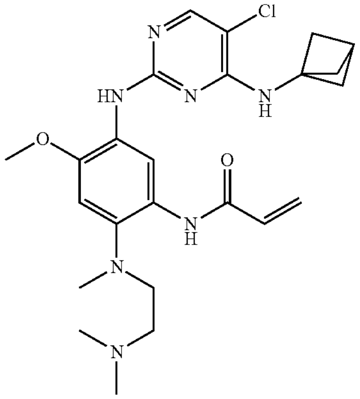

Compound 009: N-(5-((4-(bicyclo[1.1.1]pentan-1-ylamino)-5-chloropyrimidin-2-yl)amino)-2-((2-(dimethylamino)ethyl)(methyl)amino)-4-methoxyphenyl) acrylamide (ESI) m/z: 488.31 $(M+H)^+$

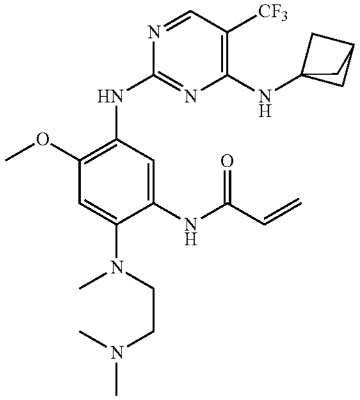

Compound 010: N-(5-((4-(bicyclo[1.1.1]pentan-1-ylamino)-5-(trifluoromethyl)pyrimidin-2-yl)amino)-2-((2-(dimethylamino)ethyl)(methyl)amino)-4-methoxyphenyl)acrylamide (ESI) m/z: 520.19 $(M+H)^+$

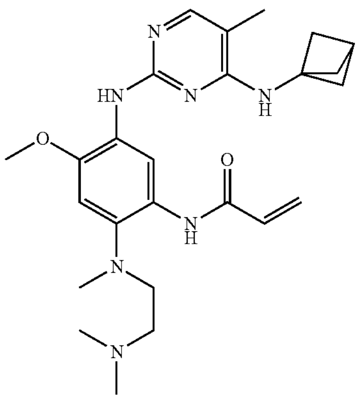

Compound 012: N-(5-((4-(bicyclo[1.1.1]pentan-1-ylamino)-5-methylpyrimidin-2-yl)amino)-2-((2-(dimethylamino)ethyl)(methyl)amino)-4-methoxyphenyl)acrylamide (ESI) m/z: 466.72 (M+H)$^+$

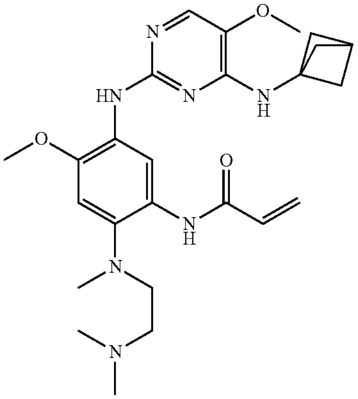

Compound 018: N-(5-((4-(bicyclo[1.1.1]pentan-1-ylamino)-5-methoxypyrimidin-2-yl)amino)-2-((2-(dimethylamino)ethyl)(methyl)amino)-4-methoxyphenyl)acrylamide (ESI) m/z: 482.27 (M+H)$^+$

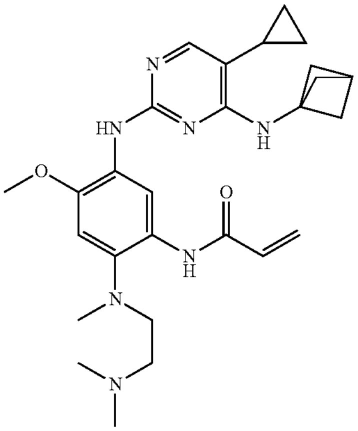

Compound 019: N-(5-((4-(bicyclo[1.1.1]pentan-1-ylamino)-5-cyclopropylpyrimidin-2-yl)amino)-2-((2-(dimethylamino)ethyl)(methyl)amino)-4-methoxyphenyl)acrylamide (ESI) m/z: 491.87 (M+H)$^+$ Scheme 2.

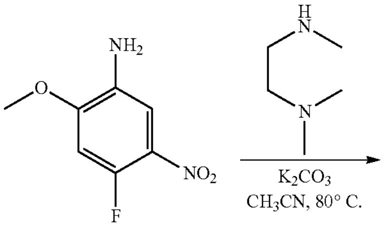

-continued

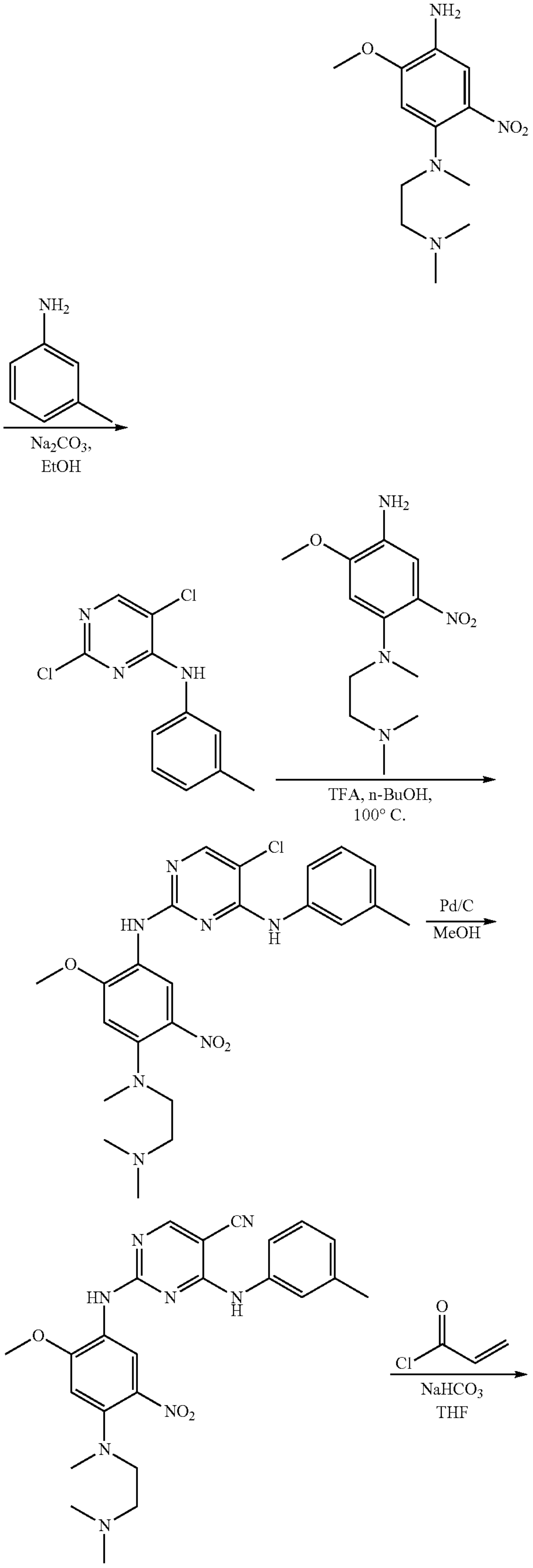

-continued

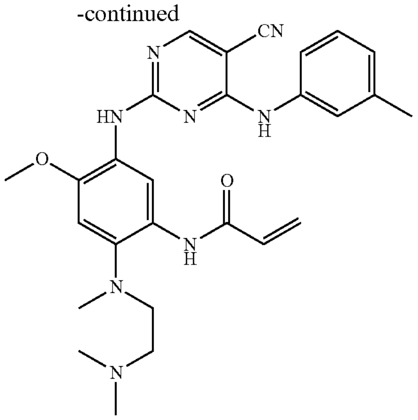

014

N1-(2-(dimethylamino)ethyl)-5-methoxy-N1-methyl-2-nitrobenzene-1,4-diamine

A mixture of 4-fluoro-2-methoxy-5-nitroaniline (5 g, 26.8 mmol), N1,N1,N2-trimethyl-ethane-1,2-diamine (5 g, 53.7 mmol) and $K_2CO_3$ (9.246 g, 67.0 mmol) in $CH_3CN$ (80 mL) was stirred at 80° C. for 6 h. The mixture was concentrated in vacuum, the residue was diluted with water (200 mL) and extracted with EtOAc (100 mL×2), the combined organic was dried over anhydrous $Na_2SO_4$, concentrated and purified by flash column chromatography (silica gel, MeOH/DCM=1/20) to afford desired product (7.0 g, yield 97%) as brown oil. LCMS (m/z): 269.2 $[M+H]^+$.

2-chloro-4-(m-tolylamino)pyrimidine-5-carbonitrile

A mixture of 2,4-dichloropyrimidine-5-carbonitrile (1.5 g, 8.6 mmol), m-toluidine (1.927 g, 8.6 mmol) and $Na_2CO_3$ (1.367 g, 12.9 mmol) in EtOH (40.0 mL) was stirred at rt for 16 h. The mixture was concentrated in vacuum, the residue was diluted with water (100 mL) and extracted with EtOAc (50 mL×2), the combined organic was dried over anhydrous $Na_2SO_4$, concentrated and purified by flash column chromatography (silica gel, EA/PE=1/5) to afford desired product (700 mg, yield 33%) as white solid. LCMS (m/z): 245.1 $[M+H]^+$.

2-((4-((2-(dimethylamino)ethyl)methyl)amino)-2-methoxy-5-nitrophenyl)amino)-4-(m-tolylamino)pyrimidine-5-carbonitrile A mixture of 2-chloro-4-(m-tolylamino)pyrimidine-5-carbonitrile (550 mg, 2.25 mmol), N1-(2-(dimethylamino)ethyl)-5-methoxy-N1-methyl-2-nitrobenzene-1,4-diamine (725 mg, 2.70 mmol) and TFA (1026 mg, 9.0 mmol) in n-BuOH (20.0 mL) was stirred at 100° C. for 16 h. The mixture was concentrated in vacuum, the residue was diluted with brine (100 mL) and extracted with EtOAc (50 mL×2), the combined organic was dried over anhydrous $Na_2SO_4$, concentrated and purified by flash column chromatography (silica gel, MeOH/DCM=1/20) to afford desired product (400 mg, yield 37%) as brow oil. LCMS (m/z): 477.3 $[M+H]^+$.

2-((5-amino-4-((2-(dimethylamino)ethyl(methyl)amino)-2-methoxyphenyl)amino)-4-(m-tolylamino)pyrimidine-5-carbonitrile A mixture of 2-(4-((2-(dimethylamino)ethyl)(methyl)amino)-2-methoxy-5-nitrophenylamino)-4-(m-tolylamino)pyrimidine-5-carbonitrile (300 mg, 0.63 mmol) and Pd/C (10%, 150 mg) in MeOH (20.0 mL) was stirred at rt under $H_2$ (1 atm) for 2 h, the mixture was filtered through celite, the filtrate was concentrated to leave crude product (250 mg, crude) as oil. LCMS (m/z): 447.3 $[M+H]^+$.

Compound 014: N-(5-((5-cyano-4-(m-tolylamino)pyrimidin-2-yl)amino)-2-((2-(dimethyl-amino)ethyl)(methyl)amino)-4-methoxyphenyl)acrylamide A mixture of 2-(5-amino-4-((2-(dimethylamino)ethyl)(methyl)amino)-2-methoxyphenyl-amino)-4-(m-tolylamino)pyrimidine-5-carbonitrile (200 mg, 0.44 mmol), acryloyl chloride (40 mg, 0.44 mmol) and saturated $NaHCO_3$ solution (2.0 mL) in THF (5.0 mL) was stirred at rt for 1 h. The mixture was diluted with brine (100 mL) and extracted with ethyl acetate (100 mL×2), the combined organic phase was washed with brine (100 mL×2), dried over anhydrous $Na_2SO_4$, filtered and concentrated in vacuum, the residue was purified by preparative HPLC (C18 column, $CH_3CN/H_2O$, containing 0.05% $NH_4HCO_3$) to obtain 014 as white solid (126 mg, yield 38%). LCMS (m/z): 501.3 [M+H]+; $^1H$ NMR (400 MHz, DMSO-$d_6$) δ (ppm) 10.05 (s, 1H), 9.15 (s, 1H), 9.03 (br, 1H), 8.42 (s, 1H), 8.26 (s, 1H), 7.39-7.34 (m, 2H), 6.98 (s, 2H), 6.78 (br, 1H), 6.38 (dd, J=16.8 Hz, 10 Hz, 1H), 6.19 (d, J=16.4 Hz, 1H), 5.73 (dd, J=10 Hz, 2.0 Hz, 1H), 3.72 (s, 3H), 2.85-2.83 (m, 2H), 2.70 (s, 3H), 2.32-2.29 (m, 2H), 2.20-2.17 (m, 9H).

Scheme 3.

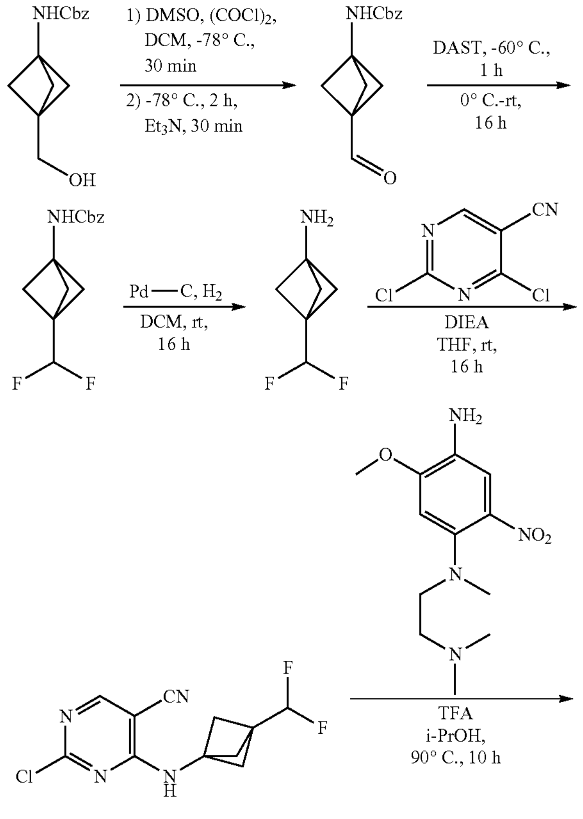

-continued

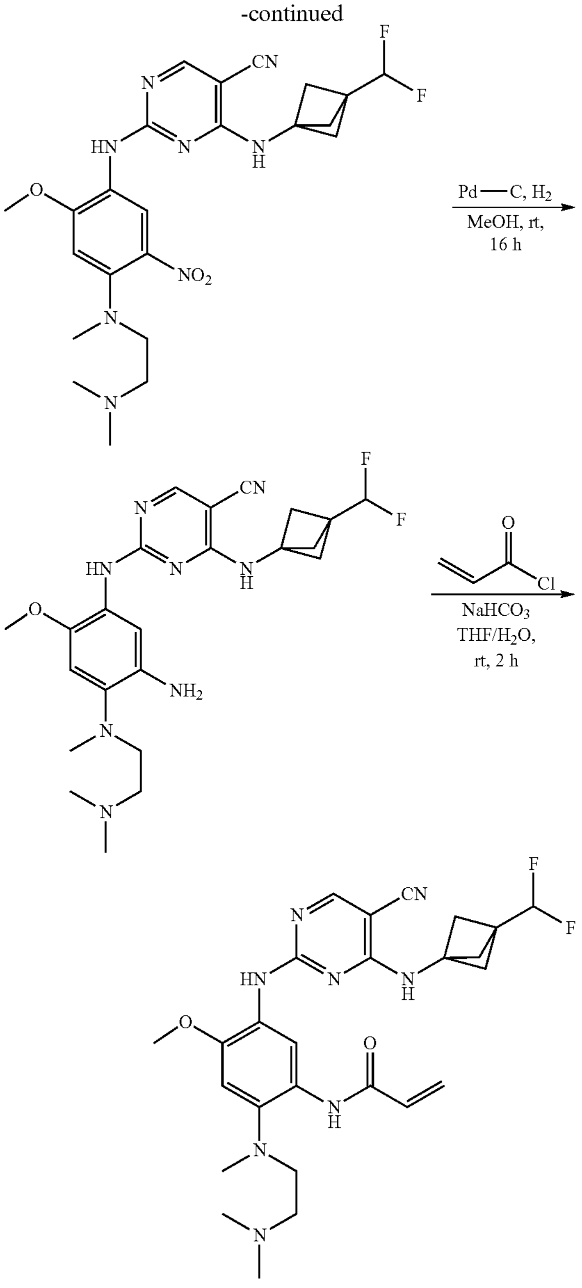

015

Benzyl 3-formylbicyclo[1.1.1]pentan-1-ylcarbamate

To a solution of $(COCl)_2$ (761 mg, 6.0 mmol) in dry DCM (5 mL) was added dropwise a solution of DMSO (938 mg, 12.0 mmol) in dry DCM (5 mL) at −78° C. The mixture was stirred at −78° C. for 30 minutes, and then a solution of benzyl 3-(hydroxymethyl)bicyclo[1.1.1]pentan-1-ylcarbamate (988 mg, 4.0 mmol) in DCM (10 mL) was added. The resulting mixture was stirred at −78° C. for 2 h and then quenched with TEA (607 mg). The mixture was stirred at −78° C. for 30 minutes and at rt for 1 h, diluted with DCM (100 mL), washed with saturated $NH_4Cl$ solution (20 mL) and brine (20 mL), dried over anhydrous $MgSO_4$, filtered and concentrated to leave crude product (1.2 g) as a colorless oil. LCMS: (m/z) 246.1 $[M+H]^+$ Benzyl 3-(difluoromethyl)bicyclo[1.1.1]pentan-1-ylcarbamate To a solution of benzyl 3-formylbicyclo[1.1.1]pentan-1-ylcarbamate (620 mg, 2.53 mmol) in dry DCM (10 mL) was added a solution of DAST (816 mg, 5.06 mmol) in dry DCM (5 mL) at −60° C. The mixture was stirred at −60° C. for 1 h, and then at rt for 3 h. The mixture was quenched with $H_2O$ (20 mL) and extracted with DCM (50 mL×3), the combined organics were washed with brine (100 mL), dried over anhydrous $Na_2SO_4$, concentrated and purified by flash chromatograph (silica gel, EtOAc/PE=1/10) to give the product (310 mg, yield 45%) as an orange solid. LCMS: (m/z) 290.1$[M+H]^+$ 3-(Difluoromethyl)bicyclo[1.1.1]pentan-1-amine To a mixture of benzyl 3-(difluoromethyl)bicyclo[1.1.1]pentan-1-ylcarbamate (520 mg, 1.95 mmol) in DCM (50 mL) was added Pd—C (10%, 260 mg). The mixture was stirred at rt under $H_2$ (1 atm) for 16 h, the mixture was filtered through celite, the cake was washed with DCM (20 mL×2), the combined filtrate and washing was concentrated to leave crude product (230 mg, yield 88.7%) as a grey solid. LCMS: (m/z) 134.1 $[M+H]^+$ 2-Chloro-4-(3-(difluoromethyl)bicyclo[1.1.1]pentan-1-ylamino)pyrimidine-5-carbonitrile To a mixture of 3-(difluoromethyl)bicyclo[1.1.1]pentan-1-amine (230 mg, 1.73 mmol) and DIEA (446 mg, 3.46 mmol) in THF (6 mL) was added a solution of 2,4-dichloropyrimidine-5-carbonitrile (301 mg, 1.73 mmol) in THF (4 mL) at 0° C. The mixture was stirred at rt for 16 h and concentrated in vacuum, the residue was purified by flash chromatograph (silica gel, EtOAc/PE=1/10) to give the product (123 mg, yield 26%) as a white solid. LCMS: (m/z) 271.1$[M+H]^+$ 4-(3-(Difluoromethyl)bicyclo[1.1.1]pentan-1-ylamino)-2-(4-((2-(dimethylamino)ethyl)-(methyl)amino)-2-methoxy-5-nitrophenylamino)pyrimidine-5-carbonitrile To a mixture of 2-chloro-4-(3-(difluoromethyl)bicyclo[1.1.1]pentan-1-ylamino)pyrimidine-5-carbonitrile (123 mg, 0.454 mmol) and N1-(2-(dimethylamino)ethyl)-5-methoxy-N1-methyl-2-nitrobenzene-1,4-diamine (158 mg, 1.3 mmol) in i-PrOH (10 mL) was added TFA (207 mg, 1.816 mmol). The mixture was stirred at 90° C. for 10 h, after cooled down to rt the mixture was diluted with EtOAc (100 mL), washed with saturated $NaHCO_3$ solution (100 mL×2) and brine (100 mL), dried over anhydrous $Na_2SO_4$, concentrated and purified by flash chromatograph (silica gel DCM/MeOH=100/5) to give the product (46 mg, yield 20%) as a brown solid. LCMS: (m/z) 503.3 $[M+H]^+$ 2-(5-Amino-4-((2-(dimethylamino)ethyl(methyl)amino)-2-methoxyphenylamino)-4-(3-(difluoromethyl)bicyclo[1.1.1]pentan-1-ylamino)pyrimidine-5-carbonitrile To a mixture of 4-(3-(difluoromethyl)bicyclo[1.1.1]pentan-1-ylamino)-2-(4-((2-(dimethylamino)ethyl)(methyl)amino)-2-methoxy-5-nitrophenylamino)pyrimidine-5-carbonitrile (46 mg, 0.091 mmol) in MeOH (10 mL) was added Pd—C (10%, 23 mg), the mixture was stirred at rt under $H_2$ (1 atm) for 2 h and filtered through celite, the cake was washed with MeOH (20 mL×2), the combined filtrate and washing was concentrated to leave crude product (35 mg, yield 82%) as a grey solid. LCMS: (m/z) 473.3 $[M+H]^+$ Compound 015: N-(5-(5-cyano-4-(3-(difluoromethyl)bicycle[1.1.1]pentan-1-ylamino)-pyrimidin-2-ylamino)-2-((2-(dimethylamino)ethyl)(methyl)amino)-4-methoxyphenyl)-acrylamide To a mixture of 2-(5-amino-4-((2-(dimethylamino)ethyl)(methyl)amino)-2-methoxyphenylamino)-4-(3-(difluoromethyl)bicyclo[1.1.1]pentan-1-ylamino)pyrimidine-5-carbonitrile (35 mg, 0.074 mmol) in THF (5 mL) was added aqueous $NaHCO_3$ solution (0.1 M, 1.5 mL), and then a solution of acryloyl chloride in dry THF (0.1 M, 1.1 mL, 0.11 mmol) was added dropwise at 0° C. The mixture was stirred at rt for 2 h and concentrated in vacuum, the residue was purified by prep-HPLC (C18 column, $CH_3CN/H_2O$, containing 0.05% $NH_4HCOs$) to give the product (6.3 mg, yield 8.8%) as a white solid. LCMS: (m/z) 527.3 $[M+H]^+$; $^1H$ NMR (500 MHz, DMSO-$d_6$) δ (ppm) 10.06 (s, 1H), 8.92 (s, 1H), 8.27 (s, 1H), 8.20 (s, 2H), 6.96 (s, 1H), 6.39-6.33 (m, 1H), 6.21-6.17 (m, 1H), 6.11-5.82 (m, 1H), 5.74-5.70 (m, 1H), 3.74 (s, 3H), 2.83 (t, J=5.6 Hz, 2H), 2.68 (s, 3H), 2.30 (t, J=5.6 Hz, 2H), 2.18 (s, 6H), 2.01-1.74 (m, 6H).

Scheme 4.

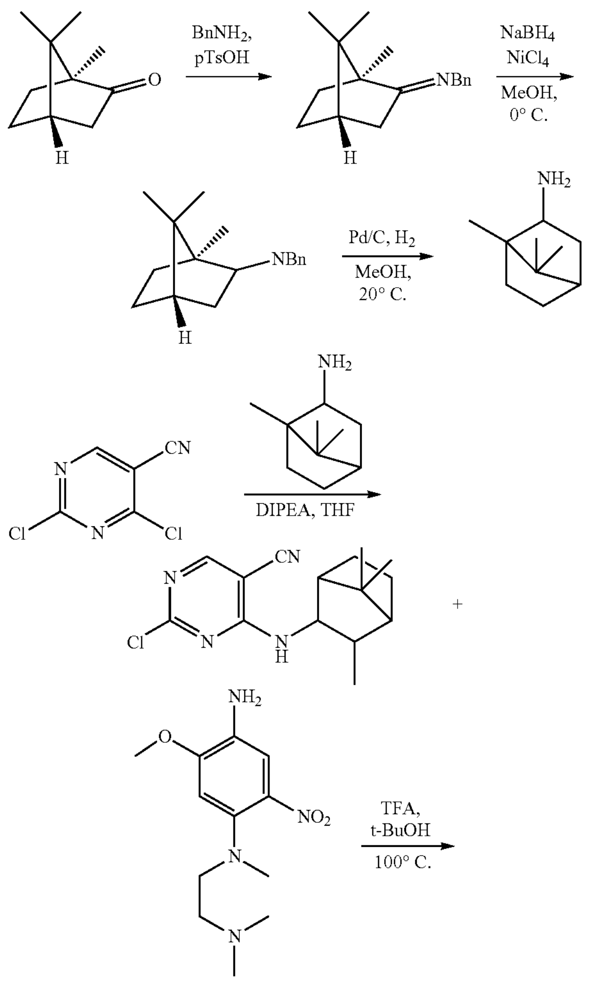

-continued

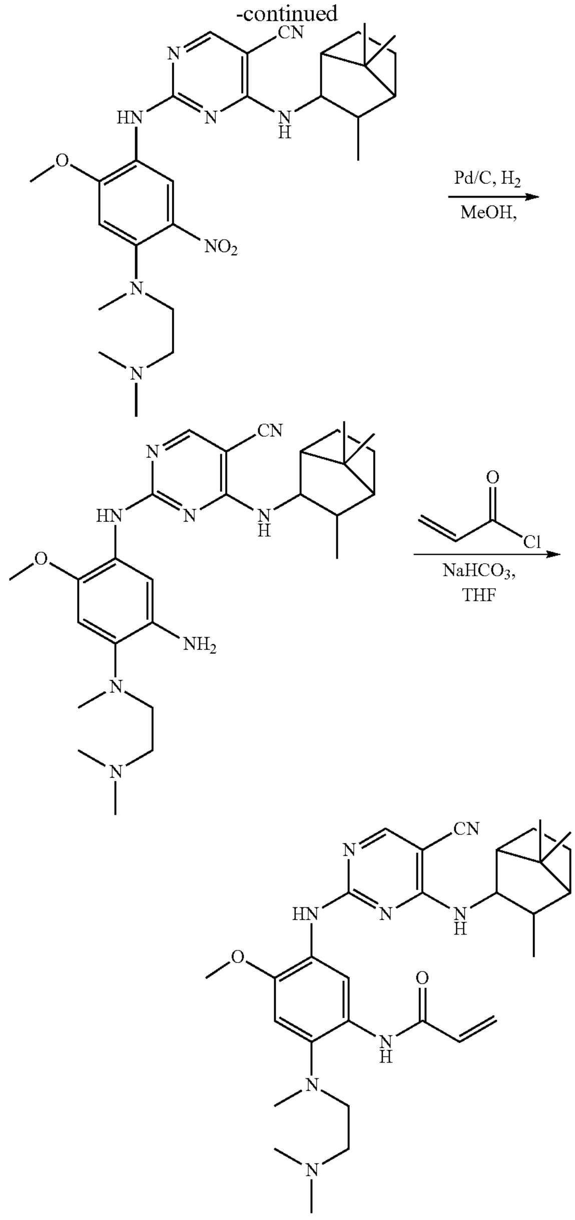

016

(1S,4S,Z)—N-Benzyl-1,7,7-trimethylbicyclo[2.2.1]heptan-2-imine

To a solution of (1S,4S)-1,7,7-trimethylbicyclo[2.2.1]heptan-2-one (5.0 g, 32.8 mmol) and benzylamine (5 g, 46.7 mmol) in toluene (60 mL) was added 4-methylbenzenesulfonic acid (283 mg, 1.64 mmol). The mixture was stirred at reflux (130° C.) under $N_2$ protection for 12 h. LCMS showed the starting material was consumed. The mixture was concentrated and purified by flash chromatograph (silica gel, PE:EA=5:1) to give the desired product (2.50 g, 31% yield) as colorless oil. LCMS (m/z): 242.1 $[M+H]^+$.

(1S,4S)—N-Benzyl-1,7,7-trimethylbicyclo[2.2.1]heptan-2-amine

To a solution of (E)-1-phenyl-N-((1S,4S)-1,7,7-trimethylbicyclo[2.2.1]heptan-2-ylidene)methanamine (2.2 g, 9.11 mmol) in MeOH (50 mL) was added $NaBH_4$ (690 mg, 18.2 mmol) and $NiCl_2$ (12 mg, 0.09 mmol) at 0° C. The reaction mixture was stirred at 20° C. for 12 h and used directly for the next step without any work up. LCMS (m/z): 244.3 $[M+H]^+$.

(1S,4S)-1,7,7-Trimethylbicyclo[2.2.1]heptan-2-amine

To a solution of (1S,4S)—N-benzyl-1,7,7-trimethylbicyclo[2.2.1]heptan-2-amine (1100 mg, 4.52 mmol) in MeOH (50 mL) was added Pd/C (10%, 481 mg). The reaction mixture was stirred at 20° C. under $H_2$ (15 psi) for 4 h. LCMS showed the starting material was consumed, and the desired mass was found. The reaction mixture was concentrated and purified by column chromatography (silica gel, DCM:MeOH (5% $Et_3N$ in MeOH)=20:1) to give the desired product (460 mg, 33% yield) as an off-white solid. LCMS (m/z): 154.3 $[M+H]^+$.

2-Chloro-4-((3,7,7-trimethylbicyclo[2.2.1]heptan-2-yl)amino)pyrimidine-5-carbonitrile To a solution of 2,4-dichloropyrimidine-5-carbonitrile (500 mg, 2.87 mmol) in THF (15 mL) was added DIPEA (557 mg, 4.31 mmol) and 1,7,7-trimethylbicyclo[2.2.1]heptan-2-amine (440 mg, 2.87 mmol) at 0° C. The reaction mixture was stirred at 20° C. for 12 h and concentrated in vacuo, the crude was purified by column chromatography (silica gel, PE:EA=20:1) to give the desired product (640 mg, 76% yield) as an yellow oil. LCMS (m/z): 291.2 $[M+H]^+$.

2-((4-((2-(Dimethylamino)ethyl)(methyl)amino)-2-methoxy-5-nitrophenyl)amino)-4-((3,7,7-trimethylbicyclo[2.2.1]heptan-2-yl)amino)pyrimidine-5-carbonitrile A mixture of 2-chloro-4-(3,7,7-trimethylbicyclo[2.2.1]heptan-2-ylamino)pyrimidine-5-carbonitrile (290 mg, 1.0 mmol), N1-(2-(dimethylamino)ethyl)-5-methoxy-N1-methyl-2-nitrobenzene-1,4-diamine (405 mg, 1.5 mmol) and TFA (500 mg, 4.0 mmol) in 2-BuOH (10.0 mL) was stirred at 100° C. for 16 h. The mixture was concentrated and purified by column chromatography (silica gel, MeOH/DCM=1/20) to obtained the desired product as brown solid (250 mg yield: 47%). LCMS (m/z): 523.3 $[M+H]^+$.

2-((5-Amino-4-((2-(dimethylamino)ethyl)(methyl)amino)-2-methoxyphenyl)amino)-4-((3,7,7-trimethylbicyclo[2.2.1]heptan-2-yl)amino)pyrimidine-5-carbonitrile A mixture of 2-(4-((2-(dimethylamino)ethyl)(methyl)amino)-2-methoxy-5-nitrophenylamino)-4-(3,7,7-trimethylbicyclo[2.2.1]heptan-2-ylamino)pyrimidine-5-carbonitrile (250 mg, 0.47 mmol) and Pd/C (10%, 150 mg) in MeOH (30.0 mL) was stirred at rt under $H_2$ (1 atm) for 2 h, the mixture was filtered through celite, the filtrate was concentrated to leave crude product (200 mg) as brown oil. LCMS (m/z): 493.4 $[M+H]^+$.

Compound 016: N-(5-((5-cyano-4-((3,7,7-trimethylbicyclo[2.2.1]heptan-2-yl)amino)-pyrimidin-2-yl)amino)-2-((2-(dimethylamino)ethyl)(methyl)amino)-4-methoxyphenyl)-acrylamide A mixture of 2-(5-amino-4-((2-(dimethylamino)ethyl)(methyl)amino)-2-methoxyphenyl-amino)-4-(3,7,7-trimethylbicyclo[2.2.1]heptan-2-ylamino)pyrimidine-5-carbonitrile (200 mg, 0.40 mmol), acryloyl chloride (45 mg, 0.40 mmol) and saturated $NaHCO_3$ solution (4.0 mL) in THF (6.0 mL) was stirred at rt for 1 h. The mixture was concentrated to remove the solvent, the residue was diluted with ethyl acetate (50 mL), washed with brine (30 mL×2), dried over anhydrous $Na_2SO_4$, concentrated and purified by preparative HPLC (C18 column, $CH_3CN/H_2O$, containing 0.05% $NH_4HCO_3$) to obtain 016 as white solid (100.3 mg, yield 45%). LCMS (m/z): 547.4 [M+H]; $^1H$ NMR (400 MHz, DMSO-$d_6$) δ (ppm) 10.16 (s, 1H), 8.68 (s, 1H), 8.30-8.26 (m, 2H), 7.24 (d, J=8.0 Hz, 1H), 7.01 (s, 1H), 6.37-6.32 (m, 1H), 6.24-6.19 (m, 1H), 5.73 (dd, $J_1$=10.0 Hz, $J_2$=2.0 Hz, 1H), 3.85-3.81 (m, 4H), 2.85 (br, 2H), 2.70 (s, 3H), 2.29 (br, 2H), 2.18 (s, 6H), 1.74-1.53 (m, 4H), 1.25-1.18 (m, 1H), 0.95-0.87 (m, 5H), 0.80-0.68 (m, 3H), 0.58 (s, 3H).

Scheme 5.

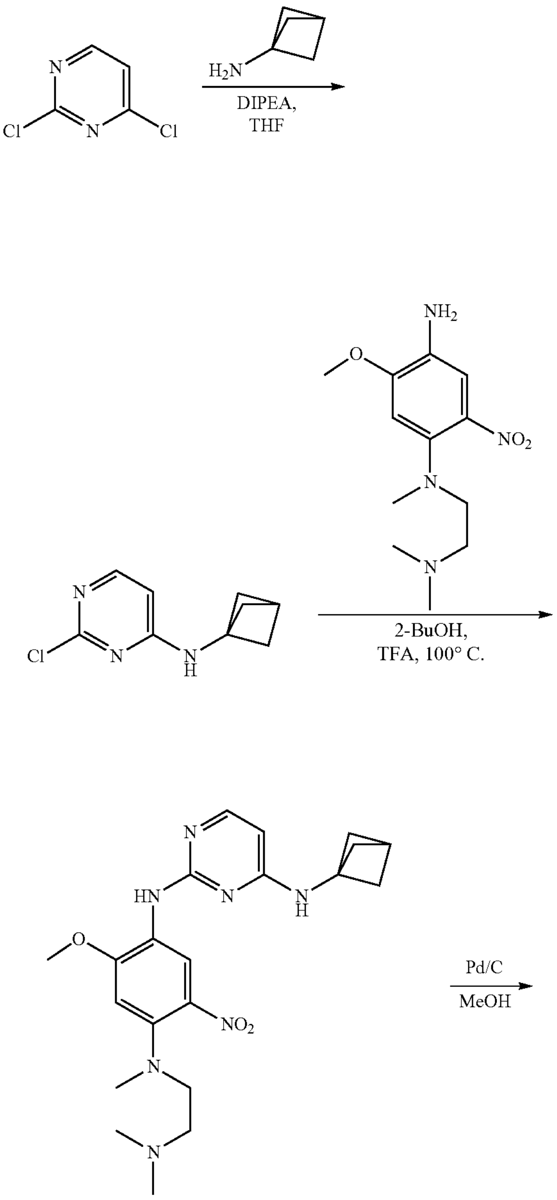

-continued

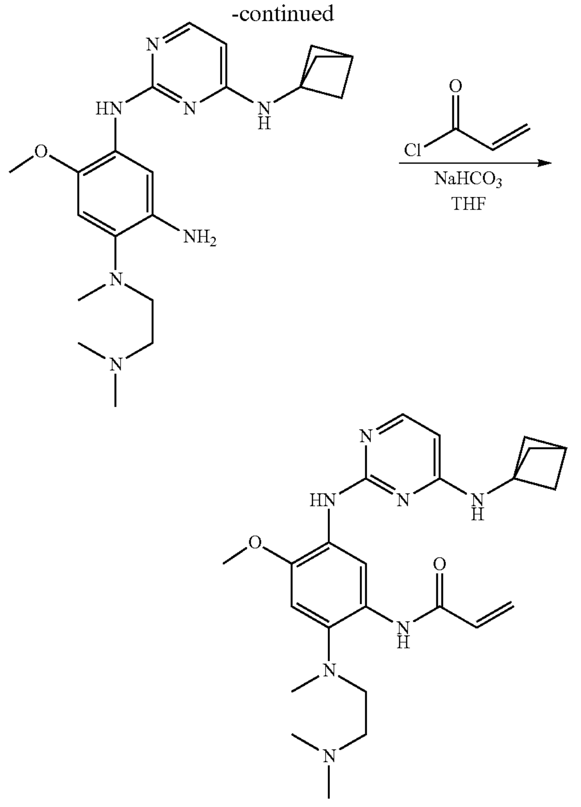

017

N-(bicyclo[1.1.1]pentan-1-yl)-2-chloropyrimidin-4-amine

A mixture of 2,4-dichloropyrimidine (414 mg, 2.8 mmol), bicyclo[1.1.1]pentan-1-amine (400 mg, 3.3 mmol) and DIPEA (1080 mg, 8.4 mmol) in THF (20.0 mL) was stirred at 60° C. for 16 h. The mixture was concentrated in vacuum, the residue was diluted with water (100 mL) and extracted with EtOAc (50 mL×2), the combined organic was dried over anhydrous $Na_2SO_4$, concentrated and purified by flash column chromatography (silica gel, EA/PE=1/5) to afford desired product (350 mg, yield 64%) as white solid. LCMS (m/z): 196.1 $[M+H]^+$.

N4-(bicyclo[1.1.1]pentan-1-yl)-N2-(4-((2-(dimethyl-amino)ethyl)(methyl)amino)-2-methoxy-5-nitrophenyl)pyrimidine-2,4-diamine A mixture of N-(bicyclo[1.1.1]pentan-1-yl)-2-chloropyrimidin-4-amine (300 mg, 1.53 mmol), N1-(2-(dimethyl-amino)ethyl)-5-methoxy-N1-methyl-2-nitrobenzene-1,4-diamine (615 mg, 2.30 mmol) and TFA (1.4 g, 12.2 mmol) in 2-BuOH (15.0 mL) was stirred at 100° C. for 16 h. The mixture was concentrated in vacuum, the residue was diluted with brine (100 mL) and extracted with EtOAc (50 mL×2), the combined organic was dried over anhydrous $Na_2SO_4$, concentrated and purified by flash column chromatography (silica gel, MeOH/DCM=1/20) to afford desired product (300 mg, yield: 34%) as brown solid. LCMS (m/z): 428.3 $[M+H]^+$.

N4-(4-(bicyclo[1.1.1]pentan-1-ylamino)pyrimidin-2-yl)-N1-(2-(dimethylamino)ethyl)-5-methoxy-N1-methylbenzene-1,2,4-triamine A mixture of N4-(bicyclo[1.1.1]pentan-1-yl)-N2-(4-((2-(dimethylamino)ethyl)(methyl)-amino)-2-methoxy-5-nitrophenyl)pyrimidine-2,4-diamine (250 mg, 0.58 mmol) and Pd/C (10%, 150 mg) in MeOH (15.0 mL) was stirred at rt under $H_2$ (1 atm) for 2 h. The mixture was filtered through celite, the filtrate was concentrated to leave crude product (250 mg, crude) as brown solid. LCMS (m/z): 398.3 $[M+H]^+$.

Compound 017: N-(5-((4-(bicyclo[1.1.1]pentan-1-ylamino)pyrimidin-2-yl)amino)-2-((2-(dimethyl-amino)ethyl)(methyl)amino)-4-methoxyphenyl)acrylamide A mixture of N4-(4-(bicyclo[1.1.1]pentan-1-ylamino)pyrimidin-2-yl)-N1-(2-(dimethyl-amino)ethyl)-5-methoxy-N1-methylbenzene-1,2,4-triamine (200 mg, 0.50 mmol), acryloyl chloride (45 mg, 0.50 mmol) and saturated $NaHCO_3$ solution (4.0 mL) in THF (6.0 mL) was stirred at rt for 1 h. The mixture was diluted with brine (100 mL) and extracted with ethyl acetate (50 mL×2), the combined organic phase was washed with brine (50 mL×2), dried over anhydrous $Na_2SO_4$, filtered and concentrated in vacuum, the residue was purified by preparative HPLC (C18 column, $CH_3CN/H_2O$, containing 0.05% $NH_4HCO_3$) to obtain 017 as white solid (176 mg, yield 61%). LCMS (m/z): 452.2 [M+H]+; $^1H$ NMR (400 MHz, DMSO-$d_6$) δ (ppm) 10.19 (s, 1H), 8.62 (s, 1H), 7.78 (d, J=5.6 Hz, 1H), 7.63 (s, 1H), 7.38 (s, 1H), 6.93 (s, 1H), 6.33 (dd, J=16.8 Hz, 10 Hz, 1H), 6.19 (dd, J=17.2 Hz, 2.0 Hz, 1H), 5.89 (br, 1H), 5.70 (dd, $J_1$=10.0 Hz, $J_2$=2.0 Hz, 1H), 3.81 (s, 3H), 2.84 (t, J=5.6 Hz, 2H), 2.67 (s, 3H), 2.29 (s, 1H), 2.23-2.20 (m, 2H), 2.17 (s, 6H), 1.97 (s, 6H).

Scheme 6.

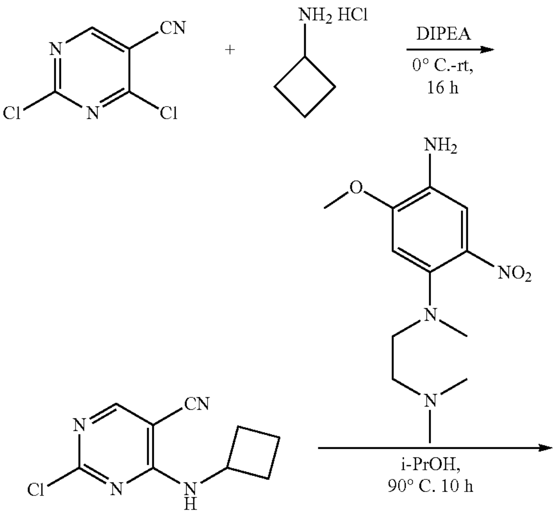

-continued

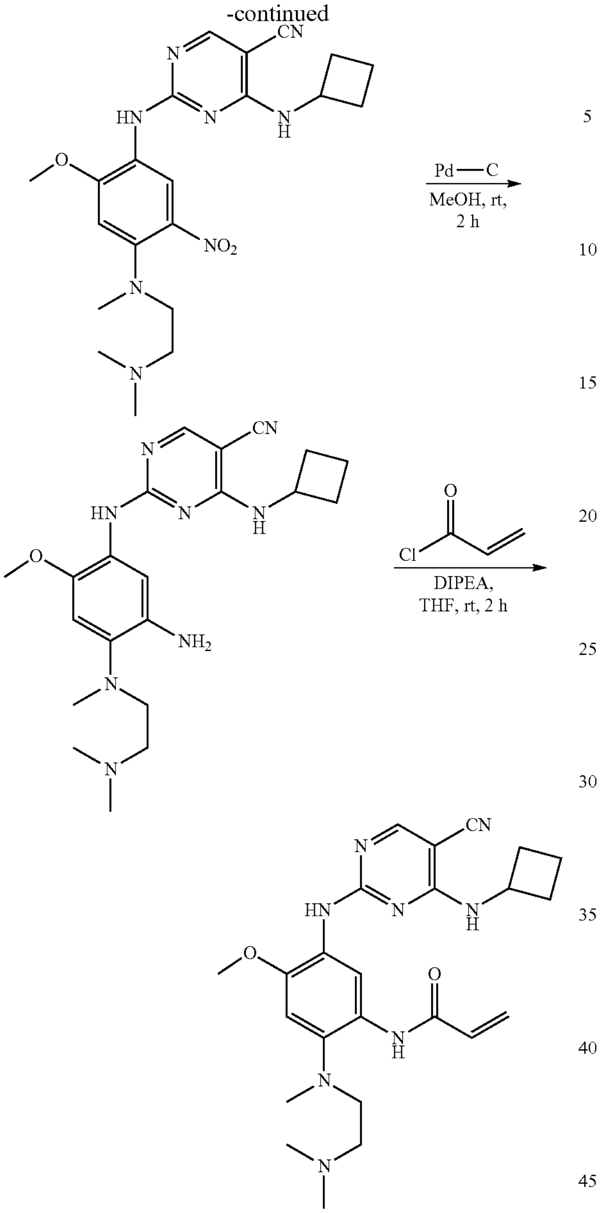

020

2-chloro-4-(cyclobutylamino)pyrimidine-5-carbonitrile

To a mixture of cyclobutanamine hydrochloride (317 mg, 3.0 mmol) and DIEA (775 mg, 6.0 mmol) in THF (10 mL) was added a solution of 2,4-dichloropyrimidine-5-carbonitrile (522 mg, 3.0 mmol) in THF (10 mL) at 0° C. The mixture was stirred at rt for 16 h and concentrated in vacuum, the residue was purified by flash column chromatograph (silica gel, PE/EtOAc=10/1) to give the desired product (180 mg, yield 29%) as a white solid. LCMS: (m/z) 209.1 $[M+H]^+$ 4-(cyclobutylamino)-2-(4-((2-(dimethylamino)ethyl)(methyl)amino)-2-methoxy-5-nitrophenylamino)pyrimidine-5-carbonitrile To a mixture of 2-chloro-4-(cyclobutylamino)pyrimidine-5-carbonitrile (180 mg, 1.06 mmol) and N-(2-(dimethylamino)ethyl)-5-methoxy-N-methyl-2-nitrobenzene-1,4-diamine (301 mg, 1.122 mmol) in i-PrOH (10 mL) was added TFA (394 mg, 3.452 mmol). The mixture was stirred at 90° C. for 10 h. After cooled down to rt the mixture was diluted with EtOAc (100 mL), washed with saturated $NaHCO_3$ solution (50 mL×2) and brine (50 mL), dried over anhydrous $Na_2SO_4$, concentrated and purified by flash column chromatograph (silica gel, DCM/MeOH=100/5) to give desired product (132 mg, yield 34%) as a brown solid. LCMS: (m/z) 441.1 $[M+H]^+$ 2-(5-amino-4-((2-(dimethylamino)ethyl)(methyl)amino)-2-methoxyphenylamino)-4-(cyclobutylamino)pyrimidine-5-carbonitrile To a solution of 4-(cyclobutylamino)-2-(4-((2-(dimethylamino)ethyl)(methyl)amino)-2-methoxy-5-nitrophenylamino)pyrimidine-5-carbonitrile (132 mg, 0.3 mmol) in MeOH (20 mL) was added Pd—C (10%, 66 mg). The mixture was stirred at rt under $H_2$ (1 atm). for 2 h and filtered through celite, the cake was washed with MeOH (20 mL×2), the combined filtrate and washing was concentrated to leave crude product (100 mg, yield 81%) as a grey solid. LCMS: (m/z) 411.3 $[M+H]^+$ Compound 020: N-(5-(5-cyano-4-(cyclobutylamino)pyrimidin-2-ylamino)-2-((2-dimethyl-amino)ethyl)(methyl)amino)-4-methoxyphenyl)acrylamide To a mixture of 2-(5-amino-4-((2-(dimethylamino)ethyl)(methyl)amino)-2-methoxyphenylamino)-4-(cyclobutylamino)pyrimidine-5-carbonitrile (100 mg, 0.244 mmol) and DIPEA (95 mg, 0.732 mmol) in dry THF (5 mL) was added a solution of acryloyl chloride (33 mg, 0.365 mmol) in dry THF (5 mL) at 0° C. The mixture was stirred at rt for 2 h and concentrated in vacuum, the residue was purified by preparative HPLC (C18 column, $CH_3CN/H_2O$, containing 0.05% $NH_4HCO_3$) to afford 020 (10 mg, yield 8.8%) as a white solid. LCMS: (m/z) 465.1 $[M+H]^+$; $^1H$ NMR (500 MHz, DMSO-$d_6$) δ (ppm) 10.11 (s, 1H), 8.87 (br, 1H), 8.30-8.23 (m, 2H), 7.84-7.83 (m, 1H), 6.97 (s, 1H), 6.39 (dd, J=17 Hz, 10.0 Hz, 1H), 6.24 (d, J=17 Hz, 1H), 5.75 (d, J=10.5 Hz, 1H), 4.74-4.70 (m, 1H), 3.82 (s, 3H), 2.85 (t, J=5.0 Hz, 2H), 2.69 (s, 3H), 2.27 (t, J=5.0 Hz, 2H), 2.18 (s, 6H), 2.16-2.01 (m, 4H), 1.60-1.51 (m, 2H).

Scheme 7.

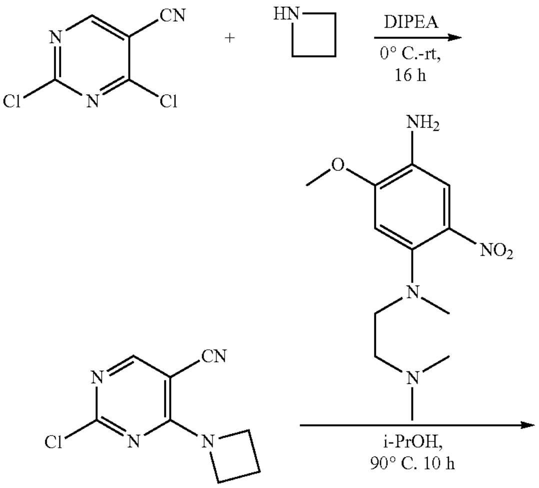

-continued

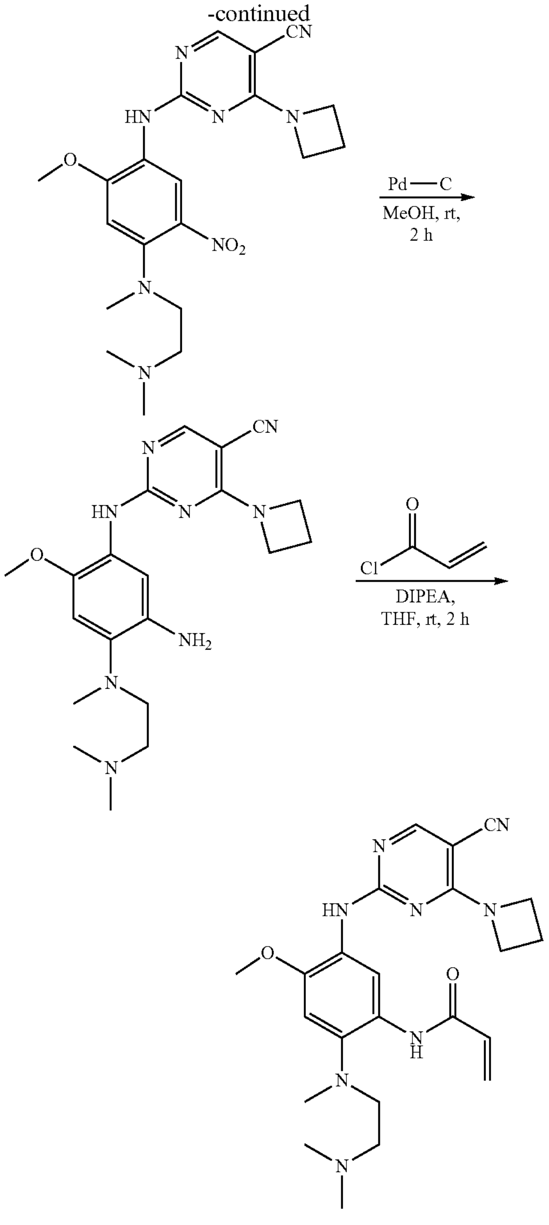

021

4-(azetidin-1-yl)-2-chloropyrimidine-5-carbonitrile

To a mixture of azetidine (171 mg, 3.0 mmol) and DIEA (775 mg, 6.0 mmol) in THF (10 mL) was added a solution of 2,4-dichloropyrimidine-5-carbonitrile (522 mg, 3.0 mmol) in THF (10 mL) at 0° C. The mixture was stirred at rt for 16 h and concentrated in vacuum, the residue was purified by flash column chromatograph (silica gel, EtOAc/PE=5%-10%) to give the desired product (226 mg, yield 39%) as a white solid. LCMS: (m/z) 195.1 $[M+H]^+$ 4-(azetidin-1-yl)-2-(4-((2-(dimethylamino)ethyl)(methyl)amino)-2-methoxy-5-nitrophenylamino)pyrimidine-5-carbonitrile To a mixture of 4-(azetidin-1-yl)-2-chloropyrimidine-5-carbonitrile (207 mg, 1.06 mmol) and N-(2-(dimethylamino)ethyl)-5-methoxy-N-methyl-2-nitrobenzene-1,4-diamine (370 mg, 1.378 mmol) in i-PrOH (10 mL) was added TFA (483 mg, 4.24 mmol). The mixture was stirred at 90° C. for 10 h. After cooled down to rt the mixture was diluted with EtOAc (100 mL), washed with saturated $NaHCO_3$ solution (50 mL×2) and brine (50 mL), dried over anhydrous $Na_2SO_4$, concentrated and purified by flash column chromatograph (silica gel, DCM/MeOH=100/5) to give desired product (186 mg, yield 38%) as a brown solid. LCMS: (m/z) 427.3 $[M+H]^+$ 2-(5-amino-4-((2-(dimethylamino)ethyl)(methyl)amino)-2-methoxyphenylamino)-4-(azetidin-1-yl)pyrimidine-5-carbonitrile To a solution of 4-(azetidin-1-yl)-2-(4-((2-(dimethylamino)ethyl)(methyl)amino)-2-methoxy-5-nitrophenylamino)pyrimidine-5-carbonitrile (186 mg, 0.44 mmol) in MeOH (20 mL) was added Pd—C (10%, 93 mg). The mixture was stirred at rt under $H_2$ (1 atm) for 2 h and filtered through celite, the cake was washed with MeOH (20 mL×2), the combined filtrate and washing was concentrated to leave crude product (140 mg, yield 80%) as a grey solid. LCMS: (m/z) 397.3 $[M+H]^+$ Compound 021: N-(5-(4-(azetidin-1-yl)-5-cyanopyrimidin-2-ylamino)-2-((2-(dimethyl-amino)ethyl)(methyl)amino)-4-methoxyphenyl)acrylamide To a mixture of 2-(5-amino-4-((2-(dimethylamino)ethyl)(methyl)amino)-2-methoxy-phenylamino)-4-(azetidin-1-yl)pyrimidine-5-carbonitrile (140 mg, 0.353 mmol) and DIPEA (137 mg, 1.059 mmol) in dry THF (5 mL) was added a solution of acryloyl chloride (48 mg, 0.53 mmol) in dry THF (5 mL) at 0° C. The mixture was stirred at rt for 2 h and concentrated in vacuum, the residue was purified by preparative HPLC (C18 column, $CH_3CN/H_2O$, containing 0.05% $NH_4HCO_3$) to afford 021 (40 mg, yield 25%) as a white solid. LCMS: (m/z) 451.3 $[M+H]^+$; $^1H$ NMR (500 MHz, DMSO-$d_6$) δ (ppm) 10.03 (s, 1H), 8.78 (br, 1H), 8.32-8.25 (m, 2H), 6.96 (s, 1H), 6.35 (dd, J=17 Hz, 10.0 Hz, 1H), 6.20 (d, J=17 Hz, 1H), 5.72 (d, J=10.5 Hz, 1H), 4.30 (br, 4H), 3.81 (s, 3H), 2.84 (t, J=5.5 Hz, 2H), 2.68 (s, 3H), 2.33 (q, J=7.5 Hz, 2H), 2.27 (t, J=6.0 Hz, 2H), 2.18 (s, 6H).

Scheme 8.

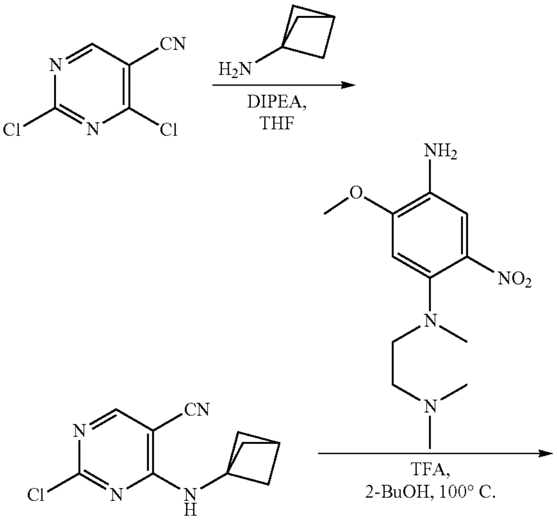

-continued

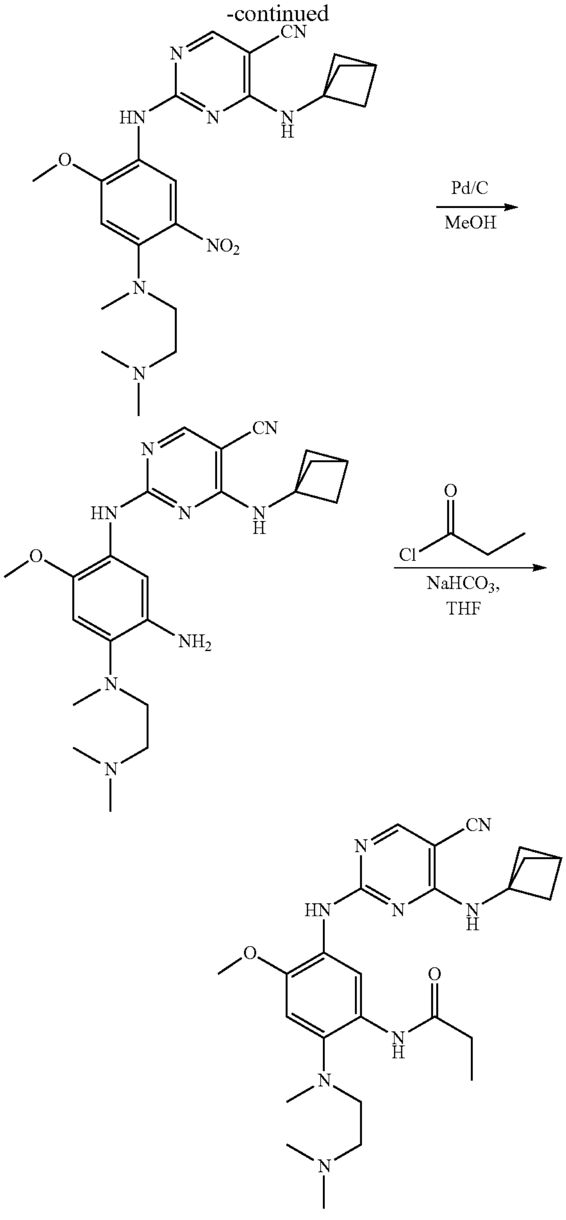

028

4-(bicyclo[1.1.1]pentan-1-ylamino)-2-chloropyrimidine-5-carbonitrile

A mixture of 2,4-dichloropyrimidine-5-carbonitrile (600 mg, 3.4 mmol), bicyclo[1.1.1]-pentan-1-amine (410 mg, 3.4 mmol) and DIPEA (1315 mg, 10.2 mmol) in THF (20.0 mL) was stirred at 0° C. for 16 h. The mixture was concentrated in vacuum, the residue was diluted with brine (50 mL) and extracted with EtOAc (50 mL×2), the combined organic was dried over anhydrous $Na_2SO_4$, filtered and concentrated to leave crude product (650 mg, yield: 86%) as white solid. LCMS (m/z): 221.1 $[M+H]^+$.

4-(bicyclo[1.1.1]pentan-1-ylamino)-2-((4-((2-(dimethylamino)ethyl)methyl)amino)-2-methoxy-5-nitrophenyl)amino)pyrimidine-5-carbonitrile A mixture of 4-(bicyclo[1.1.1]pentan-1-ylamino)-2-chloropyrimidine-5-carbonitrile (650 mg, 2.9 mmol), N1-(2-(dimethylamino)ethyl)-5-methoxy-N1-methyl-2-nitrobenzene-1,4-diamine (870 mg, 3.2 mmol) and TFA (1778 mg, 15.6 mmol) in 2-BuOH (30.0 mL) was stirred at 100° C. for 16 h. The mixture was cooled down to rt, diluted with saturated $NaHCO_3$ solution (50 mL) and extracted with EtOAc (50 mL×2), the combined organic was dried over anhydrous $Na_2SO_4$, concentrated and purified by flash column chromatograph (silica gel, MeOH/DCM=1/20) to obtain the desired product (1000 mg, yield: 76%) as brown solid. LCMS (m/z): 453.3 $[M+H]^+$.

2-((5-amino-4-((2-(dimethylamino)ethyl(methyl)amino)-2-methoxyphenyl)amino)-4-(bicyclo[1.1.1]pentan-1-ylamino)pyrimidine-5-carbonitrile A mixture of 4-(bicyclo[1.1.1]pentan-1-ylamino)-2-(4-((2-(dimethylamino)ethyl)-(methyl)-amino)-2-methoxy-5-nitrophenylamino)pyrimidine-5-carbonitrile (700 mg, 1.5 mmol) and Pd/C (10%, 350 mg) in MeOH (50.0 mL) was stirred at rt under $H_2$ (1 atm) for 2 h. The mixture was filtered through celite, the cake was washed with MeOH (20 mL×2), the combined filtrate and washing was concentrated to leave crude product (500 mg, crude) as brown oil. LCMS (m/z): 423.3 $[M+H]^+$.

Compound 028: N-(5-((4-(bicyclo[1.1.1]pentan-1-ylamino)-5-cyanopyrimidin-2-yl)amino)-2-((2-(dimethylamino)ethyl)(methyl)amino)-4-methoxyphenyl)propionamide A mixture of 2-(5-amino-4-((2-(dimethylamino)ethyl)(methyl)amino)-2-methoxyphenyl-amino)-4-(bicyclo[1.1.1]pentan-1-ylamino)pyrimidine-5-carbonitrile (150 mg, 0.35 mmol), propionyl chloride (32 mg, 0.35 mmol) and saturated $NaHCO_3$ solution (2.0 mL) in THF (6.0 mL) was stirred at rt for 1 h. The mixture was diluted with water (100 mL) and extracted with ethyl acetate (50 mL×2), the combined organic phase was washed with brine (50 mL×2), dried over anhydrous $Na_2SO_4$, concentrated and purified by preparative HPLC (C18 column, $CH_3CN/H_2O$, containing 0.05% $NH_4HCO_3$) to afford 028 as white solid (14.8 mg, yield 8.9%). LCMS (m/z): 479.3 $[M+H]^+$; $^1H$ NMR (400 MHz, DMSO-$d_6$) δ (ppm) 9.93 (br, 1H), 8.78 (br, 1H), 8.24 (s, 1H), 8.11 (br, 1H), 8.06 (s, 1H), 6.95 (s, 1H), 3.73 (s, 3H), 2.85 (t, J=5.2 Hz, 2H), 2.67 (s, 3H), 2.29-2.18 (m, 11H), 1.81 (br, 6H), 1.08 (t, J=7.6 Hz, 3H).

Scheme 9.

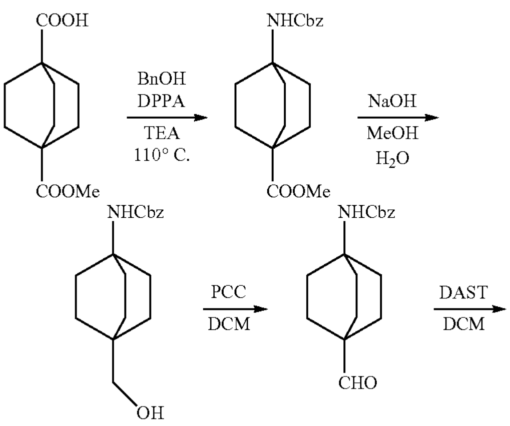

-continued

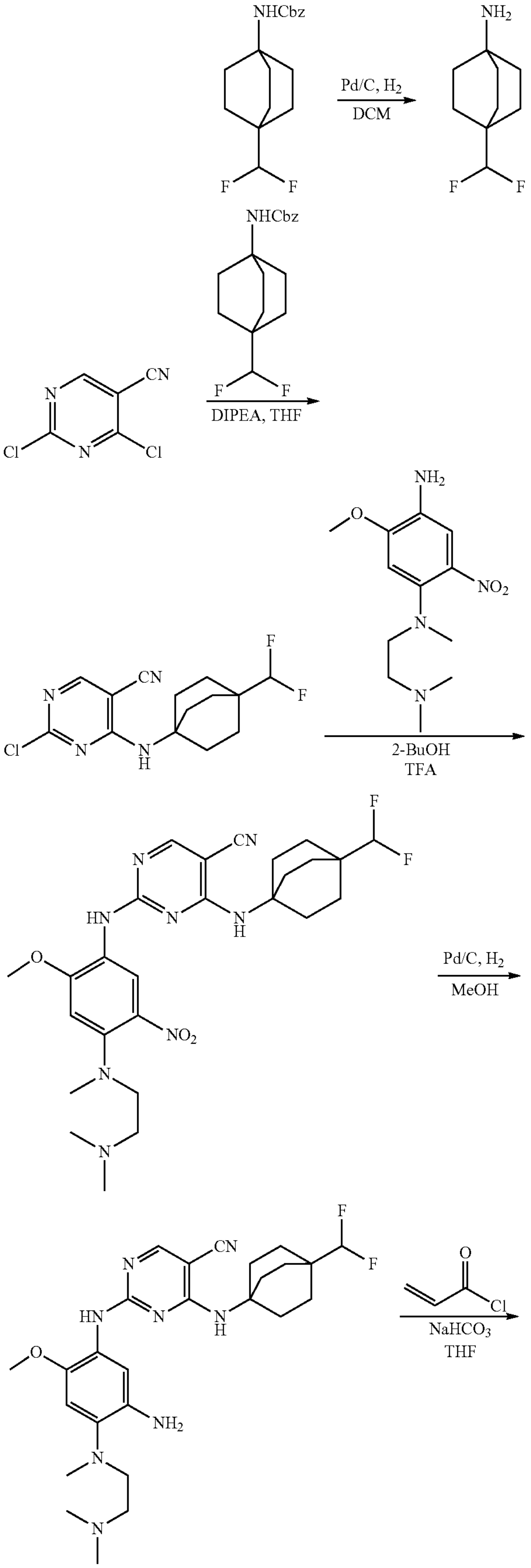

-continued

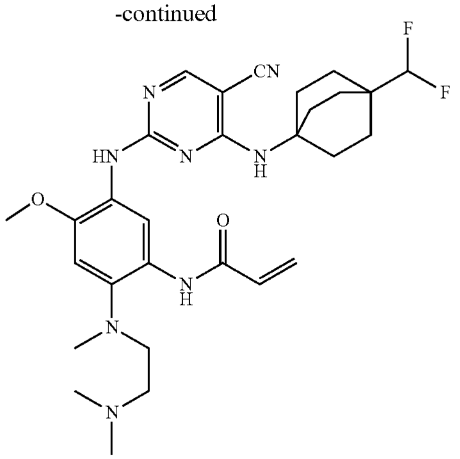

032

Methyl 4-(((benzyloxy)carbonyl)amino)bicyclo[2.2.2]octane-1-carboxylate

To a solution of 4-(methoxycarbonyl)bicyclo[2.2.2]octane-1-carboxylic acid (9.2 g, 5.0 mmol) in toluene (15.0 mL) was added DPPA (11.9 g, 43.3 mmol) and TEA (4.8 g, 47.6 mmol), the reaction mixture was stirred at rt for 1 h, and then heated at 110° C. for 1 h, BnOH (14.0 g, 130 mmol) was added and the reaction mixture was heated at 110° C. for 16 h, the mixture was concentrated in vacuo, the residue was diluted with saturated $NaHCO_3$ solution (100 mL) and extracted with EtOAc (100 mL×2), the combined organic was dried over anhydrous $Na_2SO_4$, concentrated and purified by flash chromatograph (silica gel, EA/PE=1/10) to give the product (5.0 g) as white solid. LCMS (m/z): 318.2 $[M+H]^+$.

4-(((Benzyloxy)carbonyl)amino)bicyclo[2.2.2]octane-1-carboxylic acid

A mixture of methyl 4-(benzyloxycarbonylamino)bicyclo[2.2.2]octane-1-carboxylate (4.8 g, 15.1 mmol) and NaOH (3.0 g, 75.7 mmol) in MeOH (20.0 mL) and $H_2O$ (5.0 mL) was stirred at 65° C. for 2 h, the mixture was concentrated in vacuo, the residue was diluted with water (50.0 mL), the mixture was washed with EtOAc (50 mL), the aqueous layer was adjusted to pH 4 with concentrated HCl and extracted with EtOAc (100 mL×3), the combine organic was dried over anhydrous $Na_2SO_4$, filtered and concentrated to get product as white solid (4.5 g yields: 93%). LCMS (m/z): 304.2 $[M+H]^+$.

Benzyl (4-(hydroxymethyl)bicyclo[2.2.2]octan-1-yl) carbamate $BH_3$-THF (10.0 mL) was added dropwise to the mixture of 4-(benzyloxycarbonyl-amino)bicyclo[2.2.2]octane-1-carboxylic acid (3000 mg, 10 mmol) in THF (15.0 mL) at 0° C., the mixture was stirred at rt for 2 h, quenched with MeOH (10 mL) and concentrated to get crude product as colorless oil (4.0 g, crude). LCMS (m/z): 290.2 $[M+H]^+$.

Benzyl (4-formylbicyclo[2.2.2]octan-1-yl)carbamate

PCC (2257 mg, 10.5 mmol) was added portionwise to the mixture of benzyl 4-(hydroxymethyl)bicyclo[2.2.2]octan-1- ylcarbamate (2000 mg, 7.0 mmol) in DCM (20.0 mL) at 0° C., the mixture was stirred at rt for 2 h and filtered, the filtrate was dissolved in EtOAc (100 mL), washed with saturated $NaHCO_3$ solution (50 mL), dried over anhydrous $Na_2SO_4$, filtered and concentrated to get crude product as oil (2.2 g). LCMS (m/z): 288.3 $[M+H]^+$.

Benzyl (4-(difluoromethyl)bicyclo[2.2.2]octan-1-yl) carbamate

DAST (0.65 mL, 5.2 mmol) was added to the mixture of benzyl 4-formylbicyclo-[2.2.2]octan-1-ylcarbamate (1500 mg, 5.2 mmol) in dry DCM (20.0 mL) at 0° C., the mixture was stirred at rt for 2 h, quenched carefully with water (10 mL), diluted with saturated $NaHCO_3$ solution (100 mL) and extracted with DCM (50 mL×2), the combined organic was dried over anhydrous $Na_2SO_4$, concentrated and purified by flash chromatograph (silica gel, EA/PE=1/10) to get the desired product as white solid (1.0 g, yield 62.5%). LCMS (m/z): 310.2 $[M+H]^+$.

4-(Difluoromethyl)bicyclo[2.2.2]octan-1-amine

A mixture of benzyl 4-(difluoromethyl)bicyclo[2.2.2]octan-1-ylcarbamate (900 mg, 3.0 mmol) and Pd/C (10%, 500 mg) in DCM (80.0 mL) was stirred at rt under $H_2$ (1 atm) for 16 h. The mixture was filtered through celite, the filtrate was concentrated to leave crude product (600 mg) as white solid. LCMS (m/z): 176.2 $[M+H]^+$.

2-Chloro-4-((4-(difluoromethyl)bicyclo[2.2.2]octan-1-yl)amino)pyrimidine-5-carbonitrile A mixture of 2,4-dichloropyrimidine-5-carbonitrile (600 mg, 3.4 mmol), 4-(difluoro-methyl)bicyclo[2.2.2]octan-1-amine (600 mg, 3.4 mmol) and DIPEA (877 mg, 6.8 mmol) in THF (15.0 mL) was stirred at 0° C. for 16 h. The mixture was concentrated and purified by preparative HPLC (C18 column, $CH_3CN/H_2O$, containing 0.05% FA) to afford desired product (170 mg) as white solid. LCMS (m/z): 313.2 $[M+H]^+$.

4-((4-(Difluoromethyl)bicyclo[2.2.2]octan-1-yl)amino)-2-((4-((2-(dimethylamino)-ethyl)(methyl)amino)-2-methoxy-5-nitrophenyl)amino)pyrimidine-5-carbonitrile A mixture of 2-chloro-4-(4-(difluoromethyl)bicyclo[2.2.2]octan-1-ylamino)pyrimidine-5-carbonitrile (150 mg, 0.48 mmol), N1-(2-(dimethylamino)ethyl)-5-methoxy-N1-methyl-2-nitrobenzene-1,4-diamine (154 mg, 0.57 mmol) and TFA (219 mg, 1.92 mmol) in 2-BuOH (12.0 mL) was stirred at 100° C. for 16 h. The mixture was concentrated in vacuum, the residue was diluted with saturated $NaHCO_3$ solution (50 mL) and extracted with EtOAc (50 mL), the organic layer was dried over anhydrous $Na_2SO_4$, concentrated and purified by flash chromatograph (silica gel, MeOH/DCM=1/20) to afford desired product (100 mg) as brown solid. LCMS (m/z): 545.3 $[M+H]^+$.

2-((5-Amino-4-((2-(dimethylamino)ethyl)(methyl)amino)-2-methoxyphenyl)amino)-4-((4-(difluoromethyl)bicyclo[2.2.2]octan-1-yl)amino)pyrimidine-5-carbonitrile A mixture of 4-(4-(difluoromethyl)bicyclo[2.2.2]octan-1-ylamino)-2-(4-((2-(dimethyl-amino)ethyl)(methyl)amino)-

2-methoxy-5-nitrophenylamino)pyrimidine-5-carbonitrile (100 mg, 0.18 mmol) and Pd/C (10%, 50 mg) in MeOH (30.0 mL) was stirred at rt under $H_2$ (1 atm) for 2 h. The mixture was filtered through celite, the filtrate was concentrated to leave crude product (70 mg) as brown oil. LCMS (m/z): 515.3 $[M+H]^+$.

Compound 032: N-(5-((5-cyano-4-((4-(difluoromethyl)bicyclo[2.2.2]octan-1-yl)amino)-pyrimidin-2-yl)amino)-2-((2-(dimethylamino)ethyl)(methyl)amino)-4-methoxyphenyl)-acrylamide A mixture of 2-(5-amino-4-((2-(dimethylamino)ethyl)(methyl)amino)-2-methoxyphenyl-amino)-4-(4-(difluoromethyl)bicyclo[2.2.2]octan-1-ylamino)pyrimidine-5-carbonitrile (70 mg, 0.13 mmol), acryloyl chloride (12.2 mg, 0.13 mmol) and saturated $NaHCO_3$ solution (2.0 mL) in THF (6.0 mL) was stirred at rt for 1 h. The mixture was concentrated to remove the solvent, the residue was diluted with ethyl acetate (50 mL), washed with brine (30 mL×2), dried over anhydrous $Na_2SO_4$, concentrated and purified by preparative HPLC (C18 column, $CH_3CN/H_2O$, containing 0.05% $NH_4HCO_3$) to obtain 032 (26.1 mg, yield 33.7%) as white solid. LCMS (m/z): 569.3 [M+H]; $^1H$ NMR (400 MHz, DMSO-$d_6$) δ (ppm) 10.06 (s, 1H), 8.89 (s, 1H), 8.44 (br, 1H), 8.23 (s, 2H), 6.98 (s, 1H), 6.40-6.33 (m, 1H), 6.22-6.15 (m, 2H), 5.74-5.39 (m, 2H), 3.73 (s, 3H), 2.84 (t, J=5.2 Hz, 2H), 2.70 (s, 3H), 2.32 (t, J=5.2 Hz, 2H), 2.19 (s, 6H), 1.78 (br, 6H), 1.34-1.28 (br, 6H).

Scheme 10

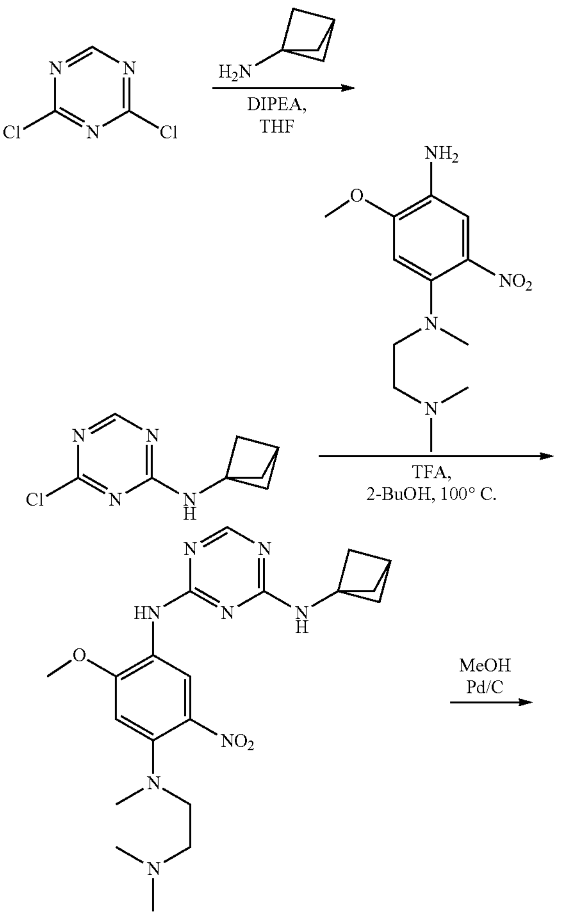

-continued

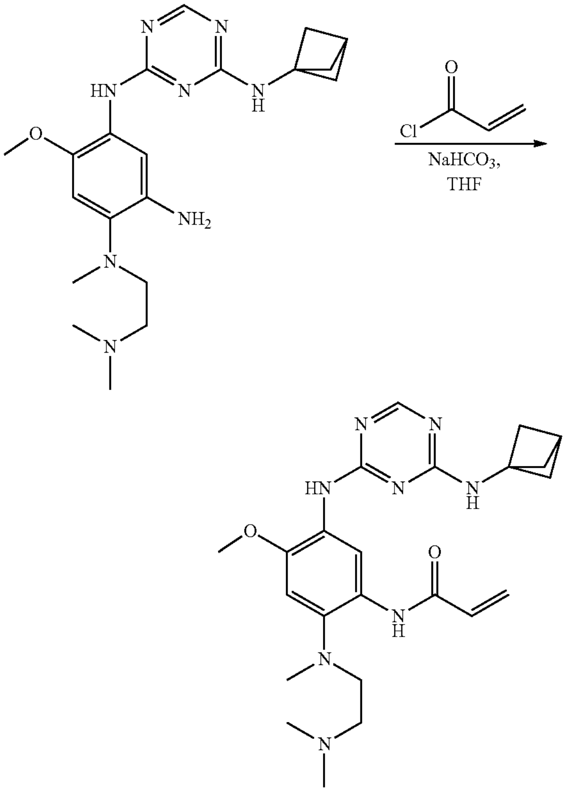

033

N-(bicyclo[1.1.1]pentan-1-yl)-4-chloro-1,3,5-triazin-2-amine

A mixture of 2,4-dichloro-1,3,5-triazine (300 mg, 2.0 mmol), bicyclo[1.1.1]pentan-1-amine (166 mg, 2.0 mmol) and DIPEA (516 mg, 4.0 mmol) in THF (20.0 mL) was stirred at 0° C. for 16 h. The mixture was concentrated in vacuum, the residue was diluted with brine (50 mL) and extracted with EtOAc (50 mL×2), the combined organic was dried over anhydrous $Na_2SO_4$, filtered and concentrated to leave crude product (350 mg, crude) as oil. LCMS (m/z): 197.1 $[M+H]^+$.

N2-(bicyclo[1.1.1]pentan-1-yl)-N4-(4-((2-(dimethylamino)ethyl)(methyl)amino)-2-methoxy-5-nitrophenyl)-1,3,5-triazine-2,4-diamine A mixture of N-(bicyclo[1.1.1]pentan-1-yl)-4-chloro-1,3,5-triazin-2-amine (350 mg, 1.7 mmol), N1-(2-(dimethylamino)ethyl)-5-methoxy-N1-methyl-2-nitrobenzene-1,4-diamine (574 mg, 2.1 mmol) and TFA (775 mg, 6.8 mmol) in 2-BuOH (20.0 mL) was stirred at 100° C. for 16 h. The mixture was cooled down to rt, diluted with saturated $NaHCO_3$ solution (50 mL) and extracted with EtOAc (50 mL×2), the combined organic was dried over anhydrous $Na_2SO_4$, concentrated and purified by flash column chromatograph (silica gel, MeOH/DCM=1/20) to afford desired product (200 mg, yield 27%) as brown solid. LCMS (m/z): 429.3 $[M+H]^+$.

N4-(4-(bicyclo[1.1.1]pentan-1-ylamino)-1,3,5-triazin-2-yl)-N1-(2-(dimethylamino)ethyl)-5-methoxy-N1-methylbenzene-1,2,4-triamine A mixture of N2-(bicyclo[1.1.1]pentan-1-yl)-N4-(4-((2-(dimethylamino)ethyl)(methyl)-amino)-2-methoxy-5-nitrophenyl)-1,3,5-triazine-2,4-diamine (200 mg, 0.346 mmol) and Pd/C (10%, 100 mg) in MeOH (30.0 mL) was stirred at rt under $H_2$ (1 atm) for 2 h, the mixture was filtered through celite, the cake was washed with MeOH (20 mL×2), the combined filtrate and washing was concentrated to leave crude product (200 mg, crude) as brown oil. LCMS (m/z): 399.3 $[M+H]^+$.

Compound 033: N-(5-((4-(bicyclo[1.1.1]pentan-1-ylamino)-1,3,5-triazin-2-yl)amino)-2-((2-(dimethylamino)ethyl)(methyl)amino)-4-methoxyphenyl)acrylamide A mixture of N4-(4-(bicyclo[1.1.1]pentan-1-ylamino)-1,3,5-triazin-2-yl)-N1-(2-(dimethylamino)ethyl)-5-methoxy-N1-methylbenzene-1,2,4-triamine (200 mg, 0.50 mmol), propionyl chloride (45 mg, 0.50 mmol) and saturated $NaHCO_3$ solution (2.0 mL) in THF (6.0 mL) was stirred at rt for 1 h. The mixture was diluted with water (100 mL) and extracted with ethyl acetate (50 mL×2), the combined organic phase was washed with brine (50 mL×2), dried over anhydrous $Na_2SO_4$, concentrated and purified by preparative HPLC (C18 column, $CH_3CN/H_2O$, containing 0.05% $NH_4HCO_3$) to afford 033 as white solid (117.2 mg, yield 51%). LCMS (m/z): 453.3 $[M+H]^+$; $^1H$ NMR (400 MHz, DMSO-$d_6$) δ (ppm) 10.22-10.01 (brs, 1H), 8.42-8.31 (m, 2H), 8.15-7.90 (m, 2H), 6.96 (s, 1H), 6.37-6.31 (m, 1H), 6.21-6.17 (m, 1H), 5.71 (d, J=10.4 Hz, 1H), 3.77 (s, 3H), 2.86 (br, 2H), 2.69 (s, 3H), 2.45-2.15 (m, 9H), 2.23-1.83 (m, 6H).

Scheme 11.

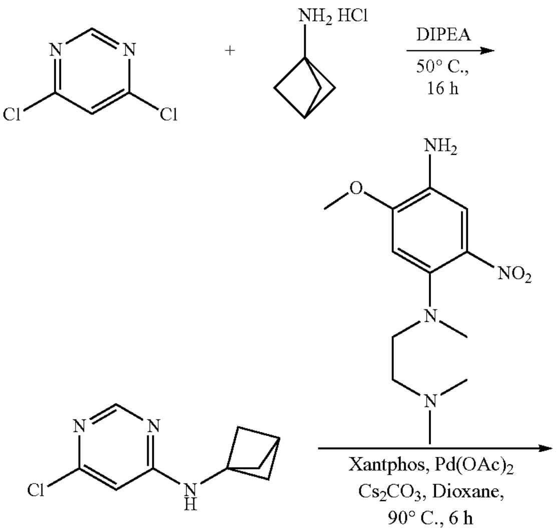

-continued

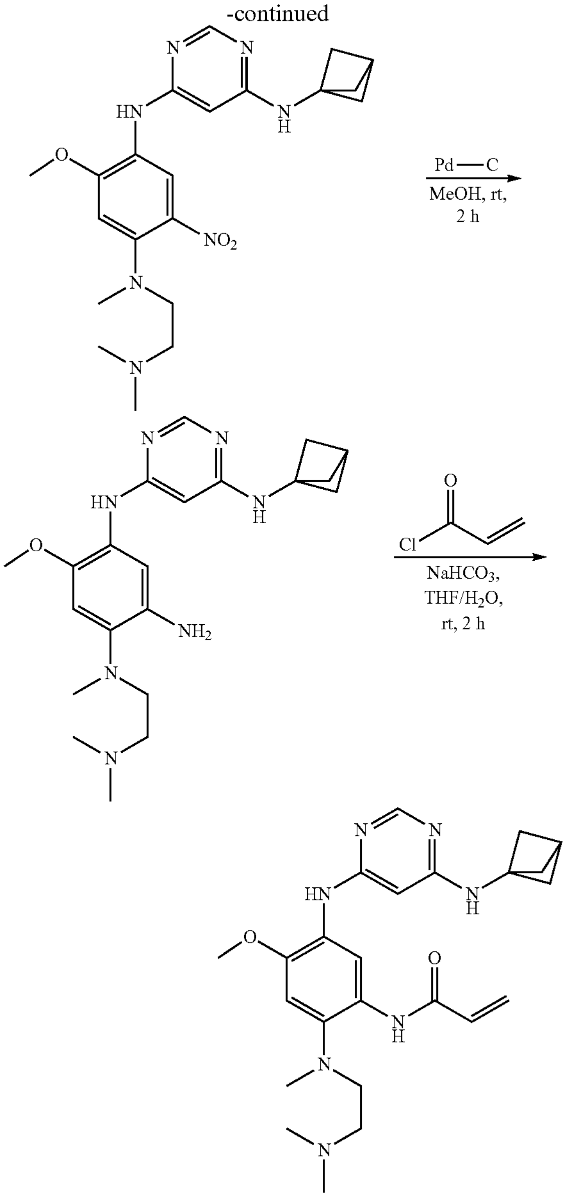

034

N-(bicyclo[1.1.1]pentan-1-yl)-6-chloropyrimidin-4-amine

To a mixture of bicyclo[1.1.1]pentan-1-amine hydrochloride (179 mg, 1.5 mmol) and DIEA (582 mg, 4.5 mmol) in THF (10 mL) was added a solution 4,6-dichloropyrimidine (223 mg, 2.0 mmol) in THF (5 mL) at rt. The mixture was stirred at 45° C. for 60 h, cooled down to rt and concentrated in vacuum, the residue was purified by flash column chromatography (silica gel, EtOAc/PE=5%-10%) to give desired product (219 mg, yield 75%) as a white solid. LCMS: (m/z) 196.1 $[M+H]^+$ $N^4$-(bicyclo[1.1.1]pentan-1-yl)-$N^6$-(4-((2-(dimethylamino)ethyl)(methyl)amino)-2-methoxy-5-nitrophenyl)pyrimidine-4,6-diamine The mixture of $N^4$-(bicyclo[1.1.1]pentan-1-yl)-N6-(4-((2-(dimethylamino)ethyl)-(methyl)amino)-2-methoxy-5-nitrophenyl)pyrimidine-4,6-diamine (219 mg, 1.12 mmol), N-(2-(dimethyl-amino)ethyl)-5-methoxy-N-methyl-2-nitrobenzene-1,4-diamine (360 mg, 1.34 mmol), Xantphos (65 mg, 0.112 mmol), $Pd(OAc)_2$ (12.6 mg, 0.056 mmol) and $Cs_2CO_3$ (547 mg, 1.68 mmol) in dry 1,4-dioxane (20 mL) was stirred at 90° C. under $N_2$ for 6 h. The mixture was cooled down to rt, diluted with DCM (50 mL) and filtered. The filtrate was concentrated and purified by flash column chromatograph (silica gel, DCM/$CH_3OH$=30/1) to give desired product (240 mg, yield 50%) as a red solid. LCMS: (m/z) 452.2 $[M+H]^+$ $N^4$-(6-(bicyclo[1.1.1]pentan-1-ylamino)pyrimidin-4-yl)-$N^1$-(2-(dimethylamino)ethyl)-5-methoxy-$N^1$-methylbenzene-1,2,4-triamine To a mixture of 4-(bicyclo[1.1.1]pentan-1-ylamino)-6-(4-((2-(dimethylamino)ethyl)-(methyl)amino)-2-methoxy-5-nitrophenylamino) nicotinonitrile (240 mg, 0.561 mmol) in MeOH (20 mL) was added Pd—C (10%, 120 mg). The mixture was stirred at rt under $H_2$ (1 atm) for 2 h and filtered through celite, the cake was washed with MeOH (20 mL×2), the combined filtrate and washing was concentrated to leave crude product (200 mg, yield 90%) as a brown solid. LCMS: (m/z) 398.3 $[M+H]^+$ Compound 034: N-(5-(6-(bicyclo[1.1.1]pentan-1-ylamino)pyrimidin-4-ylamino)-2-((2-(dimethylamino)ethyl)(methyl)amino)-4-methoxyphenyl)acrylamide To a mixture of $N^4$-(6-(bicyclo[1.1.1]pentan-1-ylamino)pyrimidin-4-yl)-$N^1$-(2-(dimethylamino)ethyl)-5-methoxy-$N^1$-methylbenzene-1,2,4-triamine (200 mg, 0.503 mmol) in THF/$H_2O$ (5 mL/2 mL) were added $NaHCO_3$ (85 mg, 1.006 mmol), and then the solution of acryloyl chloride (0.1 M, 7.5 mL, 0.75 mmol) in THF was added dropwise at 0° C. The mixture was stirred at rt for 2 h, diluted with EtOAc (100 mL), washed with brine (50 mL×2), dried over anhydrous $Na_2SO_4$, concentrated and purified by preparative HPLC (C18 column, $CH_3CN/H_2O$, containing 0.05% $NH_4HCO_3$) to afford 034 (66 mg, Yield 13.4%) as a white solid. LCMS: (m/z) 452.3 $[M+H]^+$; $^1H$ NMR (500 MHz, DMSO-$d_6$) δ (ppm) 10.07 (s, 1H), 8.48 (s, 1H), 8.04 (s, 1H), 7.98 (s, 1H), 7.35 (s, 1H), 6.97 (s, 1H), 6.39-6.33 (m, 1H), 6.23-6.18 (m, 1H), 5.80 (s, 1H), 5.27 (dd, J=10 Hz, 1.5 Hz, 1H), 3.79 (s, 3H), 2.85 (t, J=5.5 Hz, 2H), 2.69 (s, 3H), 2.39 (s, 1H), 2.27 (t, J=6.0 Hz, 2H), 2.18 (s, 6H), 2.00 (s, 6H).

Scheme 12.

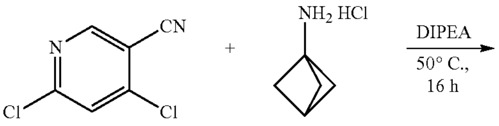

-continued

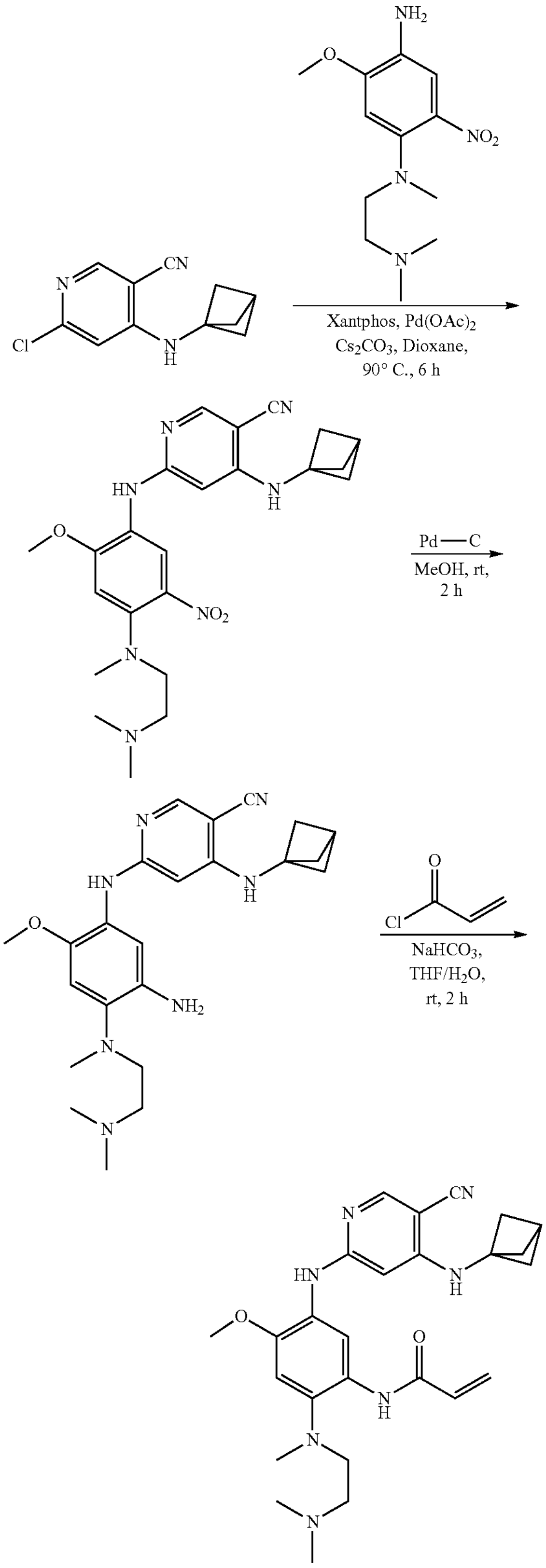

035

4-(bicyclo[1.1.1]pentan-1-ylamino)-6-chloronicotinonitrile

To a mixture of bicyclo[1.1.1]pentan-1-amine hydrochloride (239 mg, 2.0 mmol) and DIPEA (582 mg, 4.5 mmol) in THF (10 mL) was added a solution of 4,6-dichloronicotinonitrile (346 mg, 2.0 mmol) in THF (5 mL) at rt. The mixture was stirred at 50° C. for 16 h and concentrated in vacuum, the residue was purified by flash column chromatography (silica gel, EtOAc/PE=5%-10%) to give desired product (219 mg, yield 50%) as a white solid. LCMS: (m/z) 220.1 $[M+H]^+$ 4-(bicyclo[1.1.1]pentan-1-ylamino)-6-(4-((2-(dimethylamino)ethyl)(methyl)amino)-2-methoxy-5-nitrophenylamino)nicotinonitrile The mixture of 4-(bicyclo[1.1.1]pentan-1-ylamino)-6-chloronicotinonitrile (219 mg, 1.0 mmol), N-(2-(dimethylamino)ethyl)-5-methoxy-N-methyl-2-nitrobenzene-1,4-diamine (322 mg, 1.2 mmol), Xantphos (58 mg, 0.19 mmol), $Pd(OAc)_2$ (11.2 mg, 0.05 mmol) and $Cs_2CO_3$ (489 mg, 1.5 mmol) in dry 1,4-dioxane (15 mL) was stirred at 90° C. under $N_2$ for 6 h. The mixture was cooled down to rt, diluted with DCM (50 mL) and filtered. The filtrate was concentrated and purified by flash column chromatography (silica gel, DCM/$CH_3OH$=30/1) to give desired product (197 mg, yield 44%) as red solid. LCMS: (m/z) 452.2 $[M+H]^+$ 6-(5-amino-4-((2-(dimethylamino)ethyl)(methyl)amino)-2-methoxyphenylamino)-4-(bicyclo[1.1.1]pentan-1-ylamino)nicotinonitrile To a mixture of 4-(bicyclo[1.1.1]pentan-1-ylamino)-6-(4-((2-(dimethylamino)ethyl)-(methyl)amino)-2-methoxy-5-nitrophenylamino)nicotinonitrile (197 mg, 0.436 mmol) in MeOH (20 mL) was added Pd—C (10%, 99 mg). The mixture was stirred at rt under $H_2$ (1 atm) for 2 h and filtered through celite, the cake was washed with MeOH (20 mL×2), the combined filtrate and washing was concentrated to leave crude product (132 mg, yield 72%) as a brown solid. LCMS: (m/z) 422.3 $[M+H]^+$ Compound 035: N-(5-(4-(bicyclo[1.1.1]pentan-1-ylamino)-5-cyanopyridin-2-ylamino)-2-((2-(dimethylamino)ethyl)(methyl)amino)-4-methoxyphenyl)acrylamide To a mixture of 6-(5-amino-4-((2-(dimethylamino)ethyl)(methyl)amino)-2-methoxyphenyl-amino)-4-(bicyclo[1.1.1]pentan-1-ylamino) nicotinonitrile (132 mg, 0.313 mmol) in THF/$H_2O$ (5 mL/2 mL) was added $NaHCO_3$ (53 mg, 0.626 mmol), and then the solution of acryloyl chloride in THF (0.1 M, 4.7 mL, 0.47 mmol) was added dropwise at 0° C. The mixture was stirred at rt for 2 h, diluted with EtOAc (100 mL), washed with brine (50 mL×2), dried over anhydrous $Na_2SO_4$, concentrated and purified by preparative HPLC (C18 column, $CH_3CN/H_2O$, containing 0.05% $NH_4HCO_3$) to afford 035 (20 mg, Yield 13.4%) as a white solid. LCMS: (m/z) 476.3 $[M+H]^+$; $^1H$ NMR (500 MHz, DMSO-$d_6$) δ (ppm) 10.09 (s, 1H), 8.45 (s, 1H), 8.44 (s, 1H), 8.05 (s, 1H), 7.09 (s, 1H), 6.99 (s, 1H), 6.36-6.33 (m, 1H), 6.23-6.17 (m, 2H), 5.72 (d, J=11 Hz, 1H), 3.79 (s, 3H), 2.86 (t, J=5.0 Hz, 2H), 2.69 (s, 3H), 2.41 (s, 1H), 2.27 (t, J=5.0 Hz, 2H), 2.18 (s, 6H), 2.03 (s, 6H).

Scheme 13.

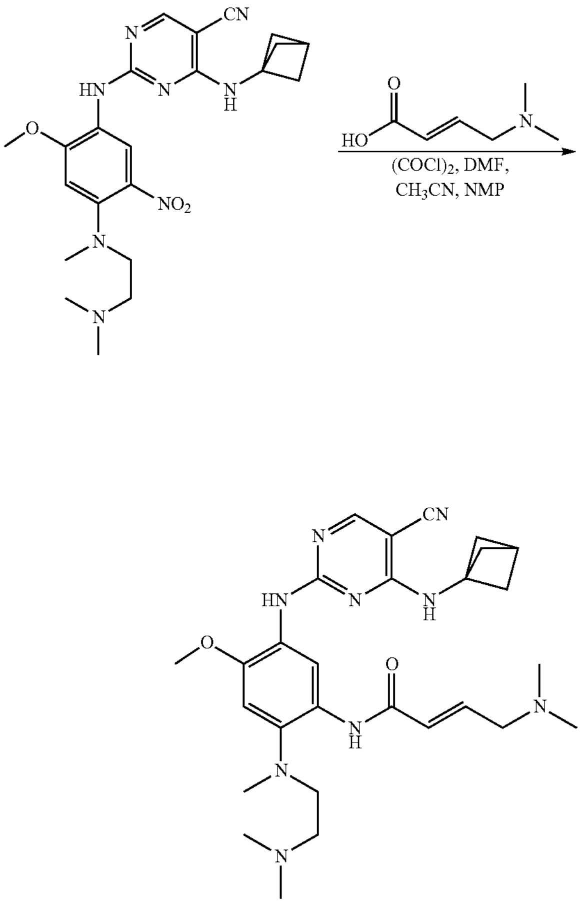

036

Compound 036: (E)-N-(5-((4-(bicyclo[1.1.1]pentan-1-ylamino)-5-cyanopyrimidin-2-yl)amino)-2-((2-(dimethylamino)ethyl)(methyl)amino)-4-methoxyphenyl)-4-(dimethylamino)but-2-enamide To the mixture of (E)-4-(dimethylamino)but-2-enoic acid (103 mg, 0.8 mmol) and DMF (0.2 mL) in dry $CH_3CN$ (4.0 mL) was added $(COCl)_2$ (101 mg, 0.8 mmol) at 0° C., the mixture was stirred at rt for 2 h, and then added dropwise to the solution of 2-(5-amino-4-((2-(dimethyl-amino)ethyl)(methyl)amino)-2-methoxyphenylamino)-4-(bicyclo[1.1.1]pentan-1-ylamino) pyrimidine-5-carbonitrile (193 mg, 0.4 mmol) in NMP (6.0 mL) at 0° C., the resulting mixture was stirred at rt for 16 h. The mixture was diluted with water (100 mL), adjusted to pH 8 with $Na_2CO_3$ and extracted with ethyl acetate (50 mL×2), the combined organic phase was washed with brine (50 mL×2), dried over anhydrous $Na_2SO_4$, concentrated and purified by preparative HPLC (C18 column, $CH_3CN/H_2O$, containing 0.05% $NH_4HCO_3$) to afford 036 as white solid (22.3 mg, yield: 10.5%). LCMS (m/z): 534.3 $[M+H]^+$; $^1H$ NMR (400 MHz, DMSO-$d_6$) δ (ppm) 10.16 (s, 1H), 8.79 (s, 1H), 8.24-8.18 (m, 3H), 7.01 (s, 1H), 6.70-6.64 (m, 1H), 6.15 (d, J=15.2 Hz, 1H), 3.74 (s, 3H), 3.05 (d, J=5.6 Hz, 2H), 2.84 (t, J=5.2 Hz, 2H), 2.69 (s, 3H), 2.26-2.19 (m, 2H), 2.19-2.16 (m, 12H), 2.09 (m, 1H), 2.00 (m, 1H), 1.65 (s, 5H).

Scheme 14.

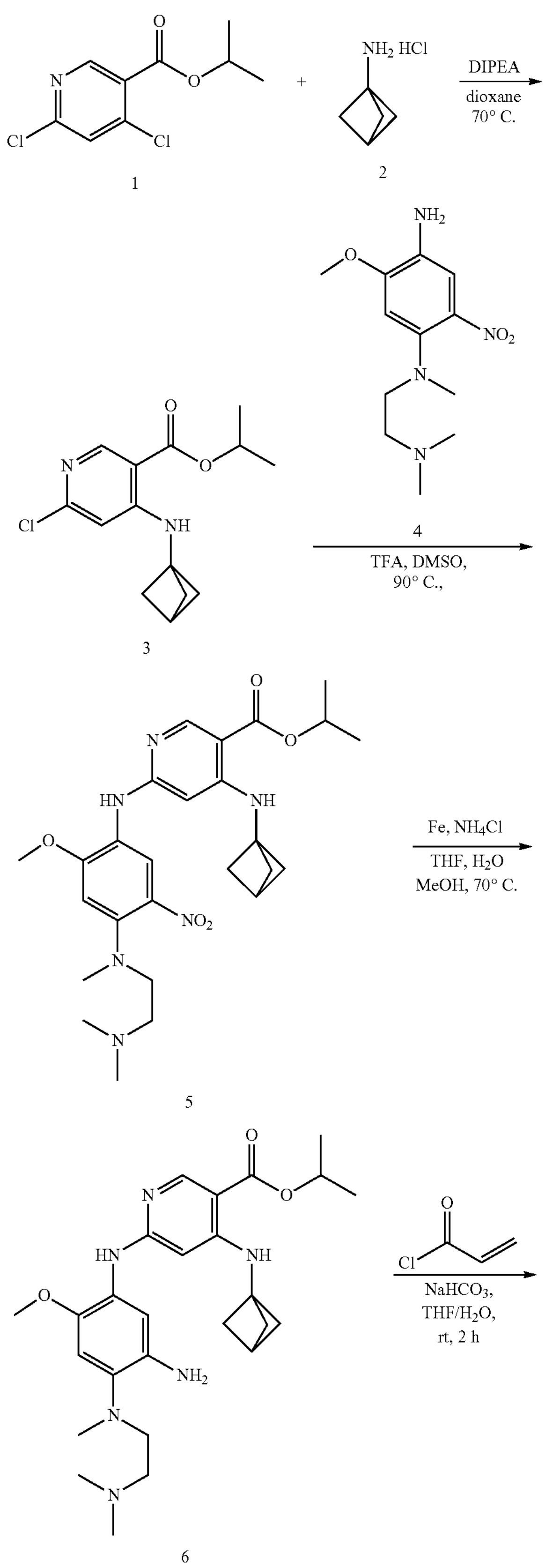

-continued

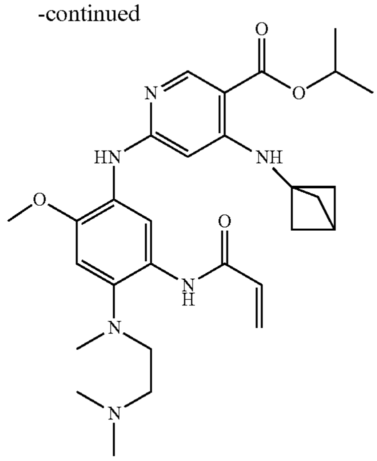

037

Isopropyl 4-(bicyclo[1.1.1]pentan-1-ylamino)-2-chloropyrimidine-5-carboxylate (3)

Isopropyl 2,4-dichloropyrimidine-5-carboxylate 1 (162 mg, 0.69 mmol) and bicyclo[1.1.1]-pentan-1-amine hydrochloride 2 (90 mg, 0.76 mmol) were dissolved in dioxane (10 mL). N,N-diisopropylethylamine (DIPEA, 360 μL, 2.1 mmol) was added, and the reaction mixture was stirred at 70° C. for 3 h. Upon cooling to rt, the reaction mixture was concentrated in vacuo. Purification by silica flash chromatography (0-50% EtOAc/hexanes) gave the title compound 3 as a light yellow oil (165 mg, 85% yield). LC-MS m/z: (pos) 282.11 ($[M+H]^+$).

Isopropyl 4-(bicyclo[1.1.1]pentan-1-ylamino)-2-((4-((2-(dimethylamino)ethyl)(methyl)-amino)-2-methoxy-5-nitrophenyl)amino)pyrimidine-5-carboxylate (5)

Isopropyl 4-(bicyclo[1.1.1]pentan-1-ylamino)-2-chloropyrimidine-5-carboxylate 3 (150 mg, 0.53 mmol) and $N^1$-(2-(dimethylamino)ethyl)-5-methoxy-$N^1$-methyl-2-nitrobenzene-1,4-diamine 4 (171 mg, 0.64 mmol) were dissolved in dimethyl sulfoxide (DMSO, 600 μL). Trifluoroacetic acid (TFA, 600 μL) was added, and the reaction mixture was stirred at 90° C. for 16 h. Upon cooling to rt, the reaction mixture was carefully quenched by dropwise addition of satd. aq. $Na_2CO_3$ until bubbling ceased. The crude mixture was extracted with EtOAc and washed with water and brine. The organic layer was collected and dried over $Na_2SO_3$, filtered, and concentrated in vacuo. Purification by silica flash chromatography (0-80% EtOAc/$CH_2Cl_2$) gave the title compound 5 (102 mg, 37% yield). LC-MS m/z: (pos) 514.25 ($[M+H]^+$).

Isopropyl 2-((5-amino-4-((2-(dimethylamino)ethyl)(methyl)amino)-2-methoxyphenyl)-amino)-4-(bicyclo[1.1.1]pentan-1-ylamino)pyrimidine-5-carboxylate (6)

Isopropyl 4-(bicyclo[1.1.1]pentan-1-ylamino)-2-((4-((2-(dimethylamino)ethyl)(methyl)-amino)-2-methoxy-5-nitrophenyl)amino)pyrimidine-5-carboxylate 5 (66.3 mg, 0.13 mmol) was dissolved in THF (3 mL) and MeOH (1 mL). Iron powder (22 mg, 0.39 mmol) was added, followed by satd. aq. $NH_4Cl$ (1.5 mL). The reaction mixture was stirred at 70° C. for 3 h. Upon cooling to rt, the reaction mixture was extracted with $CH_2Cl_2$ and washed with water. The organic layer was collected and dried over $Na_2SO_4$, filtered, and concentrated in vacuo to give the title compound 6 (63 mg, 99% yield), which was taken forward without purification. LC-MS m/z: (pos) 484.28 ([M+H]+).

Isopropyl 2-((5-acrylamido-4-((2-(dimethylamino)ethyl)(methyl)amino)-2-methoxyphenyl)-amino)-4-(bicyclo[1.1.1]pentan-1-ylamino)pyrimidine-5-carboxylate Isopropyl 2-((5-amino-4-((2-(dimethylamino)ethyl)(methyl)amino)-2-methoxyphenyl)-amino)-4-(bicyclo[1.1.1]pentan-1-ylamino)pyrimidine-5-carboxylate 6 (63 mg, 0.13 mmol) was dissolved in THF (3 mL) and satd. aq. $NaHCO_3$ (1 mL) and cooled to 0° C. Acryloyl chloride (16 μL, 0.19 mmol) was added dropwise, and the reaction mixture was stirred at 0° C. for 15 min, then warmed to rt. The reaction mixture was extracted with EtOAc, washed with water and brine. The organic layer was collected and dried over $Na_2SO_4$, filtered, and concentrated in vacuo. Purification by HPLC provided the title compound 037 as a white solid (8.7 mg). LC-MS m/z: (pos) 538.25 ($[M+H]^+$).

Scheme 15.

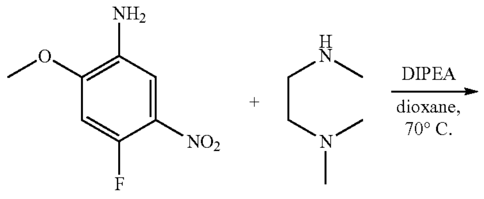

8

9

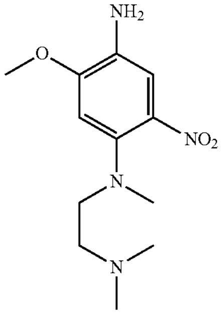

4

$N^1$-(2-(Dimethylamino)ethyl)-5-methoxy-$N^1$-methyl-2-nitrobenzene-1,4-diamine (4). To a solution of 4-fluoro-2-methoxy-5-nitroaniline 8 (1.02 g, 5.5 mmol) and $N^1$,$N^1$,$N^2$-trimethylethane-1,2-diamine 9 (1.44 mL, 11 mmol) in dioxane (10 mL) was added DIPEA (2.9 mL, 16.6 mmol). The reaction mixture was stirred at 70° C. for 4 h. Upon cooling to rt, the reaction mixture was concentrated in vacuo. Purification by silica flash chromatography (0-20% MeOH/$CH_2Cl_2$) yielded the title compound 4 as a dark red oil (1.2 g, 81% yield). LC-MS m/z: (pos) 269.14 ($[M+H]^+$).

Scheme 16.
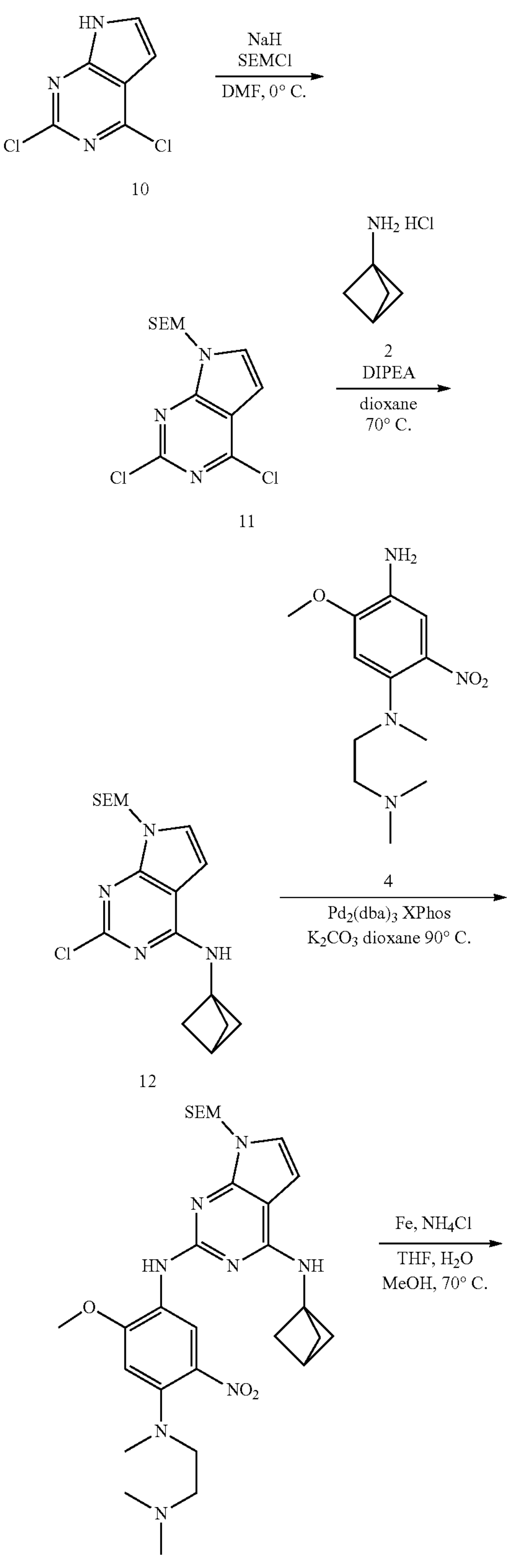
10
11
12
13
-continued
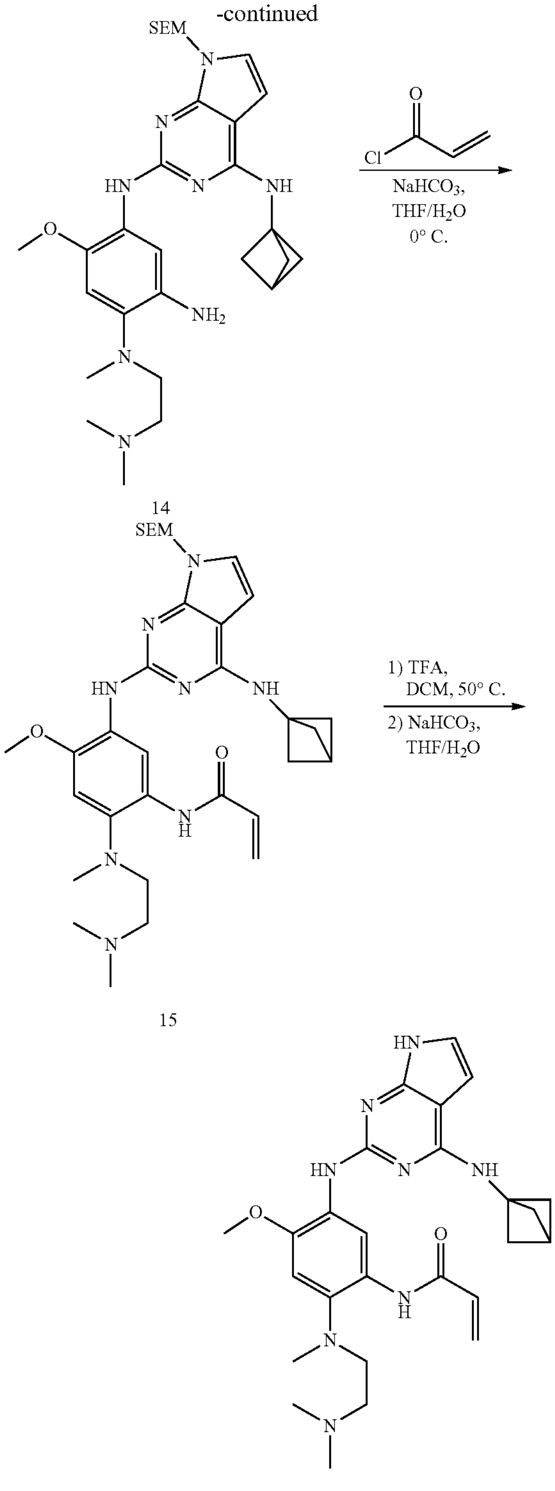
14
15
038
2,4-Dichloro-7-((2-(trimethylsilyl)ethoxy)methyl)-7H-pyrrolo[2,3-d]pyrimidine (11)
To a solution of 2,4-dichloro-7H-pyrrolo[2,3-d]pyrimidine 10 (505 mg, 2.68 mmol) in DMF (10 mL) at 0° C. was added sodium hydride (NaH, 71 mg, 2.95 mmol). The reaction mixture was stirred at 0° C. for 30 min, after which time 2-(trimethylsilyl)ethoxymethyl chloride (SEMCl, 570 μL, 3.21 mmol) was added and stirred at rt for 3 h. The reaction mixture was extracted with EtOAc, washed with $H_2O$ 2× and brine. The organic layer was collected and dried over $Na_2SO_4$, filtered, and concentrated in vacuo. Purification by silica flash chromatography gave compound 11 as a light-yellow oil (785 mg, 92% yield). LC-MS m/z: (pos) 317.97 ($[M+H]^+$).

N-(bicyclo[1.1.1]pentan-1-yl)-2-chloro-7-((2-(trimethylsilyl)ethoxy)methyl)-7H-pyrrolo[2,3-d]pyrimidin-4-amine (12)

To a solution of 2,4-dichloro-7-((2-(trimethylsilyl)ethoxy)methyl)-7H-pyrrolo[2,3-d]pyrimidine 11 (252 mg, 0.79 mmol) and bicyclo[1.1.1]pentan-1-amine hydrochloride 2 (104 mg, 0.87 mmol) in dioxane (10 mL) was added DIPEA (207 μL, 1.2 mmol). The reaction mixture was stirred at 70° C. for 5 h. Upon cooling to rt, the reaction mixture was concentrated in vacuo. Purification by silica flash chromatography gave the title compound 12 (250 mg, 86% yield). LC-MS m/z: (pos) 365.15 ($[M+H]^+$).

$N^1$-(bicyclo[1.1.1]pentan-1-yl)-$N^2$-(4-((2-(dimethylamino)ethyl)(methyl)amino)-2-methoxy-5-nitrophenyl)-7-((2-(trimethylsilyl)ethoxy)methyl)-7H-pyrrolo[2,3-d]pyrimidine-2,4-diamine (13)

To a solution of N-(bicyclo[1.1.1]pentan-1-yl)-2-chloro-7-((2-(trimethylsilyl)ethoxy)methyl)-7H-pyrrolo[2,3-d]pyrimidin-4-amine 12 (125 mg, 0.342 mmol) in dioxane (8 mL) was added aniline 4 (115 mg, 0.428 mmol) and potassium carbonate ($K_2CO_3$, 95 mg, 0.69 mmol). The reaction mixture was degassed for 5 min, then $Pd_2(dba)_3$ (15.6 mg, 0.017 mmol) and 2-dicyclohexylphosphino-2',4',6'-triisopropylbiphenyl (XPhos, 29.3 mg, 0.062 mmol) were added. The reaction mixture was stirred at 90° C. for 5 h. Upon cooling to rt, the crude mixture was filtered over a plug of celite, and concentrated in vacuo. Purification by silica flash chromatography gave the title compound 13 as a brown oil (139 mg, 68% yield). LC-MS m/z: (pos) 597.29 ($[M+H]^+$).

$N^4$-(4-(bicyclo[1.1.1]pentan-1-ylamino)-7-((2-(trimethylsilyl)ethoxy)methyl)-7H-pyrrolo[2,3-d]pyrimidin-2-yl)-$N^1$-(2-(dimethylamino)ethyl)-5-methoxy-$N^1$-methylbenzene-1,2,4-triamine (14)

To a solution of M-(bicyclo[1.1.1]pentan-1-yl)-$N^2$-(4-((2-(dimethylamino)ethyl)(methyl)amino)-2-methoxy-5-nitrophenyl)-7-((2-(trimethylsilyl)ethoxy)-methyl)-7H-pyrrolo[2,3-d]pyrimidine-2,4-diamine 13 (139 mg, 0.234 mmol) in 4:1 THF/MeOH (4 mL) was added iron powder (40 mg, 0.702 mmol), followed by satd. aq. $NH_4Cl$ (2 mL). The reaction mixture was stirred at 70° C. for 5 h. Upon cooling to rt, the reaction mixture was extracted with $CH_2Cl_2$ and washed with water. The organic layer was collected and dried over $Na_2SO_4$, filtered, and concentrated in vacuo to give the title compound 14 (126.8 mg, 95% yield), which was taken forward without purification. LC-MS m/z: (pos) 567.33 ($[M+H]^+$).

N-(5-((4-(bicyclo[1.1.1]pentan-1-ylamino)-7H-pyrrolo[2,3-d]pyrimidin-2-yl)amino)-2-((2-(dimethylamino)ethyl)(methyl)amino)-4-methoxyphenyl)acrylamide $N^4$-(4-(bicyclo[1.1.1]pentan-1-ylamino)-7-((2-(trimethylsilyl)ethoxy)methyl)-7H-pyrrolo[2,3-d]pyrimidin-2-yl)-$N^1$-(2-(dimethylamino)ethyl)-5-methoxy-N-methylbenzene-1,2,4-triamine 14 (87.4 mg, 0.154 mmol) was dissolved in THF (3 mL) and satd. aq. $NaHCO_3$ (1 mL) and cooled to 0° C. Acryloyl chloride (19 μL, 0.23 mmol) was added dropwise, and the reaction mixture was stirred at 0° C. for 15 min, then warmed to rt. The reaction mixture was extracted with EtOAc, washed with water and brine. The organic layer was collected and dried over $Na_2SO_4$, filtered, and concentrated in vacuo to give the crude acrylamide intermediate 15. LC-MS m/z: (pos) 621.36 ($[M+H]^+$).

The crude acrylamide intermediate 15 was dissolved in 1:3 TFA/$CH_2Cl_2$ (4 ml) and stirred at 50° C. for 3 h. Upon cooling to rt, the reaction mixture was concentrated in vacuo. The crude material was dissolved in THF (4 mL), and satd. aq. NaHCO3 (4 ml) was added and stirred for 6 h. The reaction mixture was extracted with EtOAc, washed with water, and brine. The organic layer was collected and dried over $Na_2SO_4$, filtered, and concentrated in vacuo. Purification by HPLC gave the title compound 038 as a white solid (12.1 mg). LC-MS m/z: (pos) 491.24 ($[M+H]^+$).

Scheme 17.

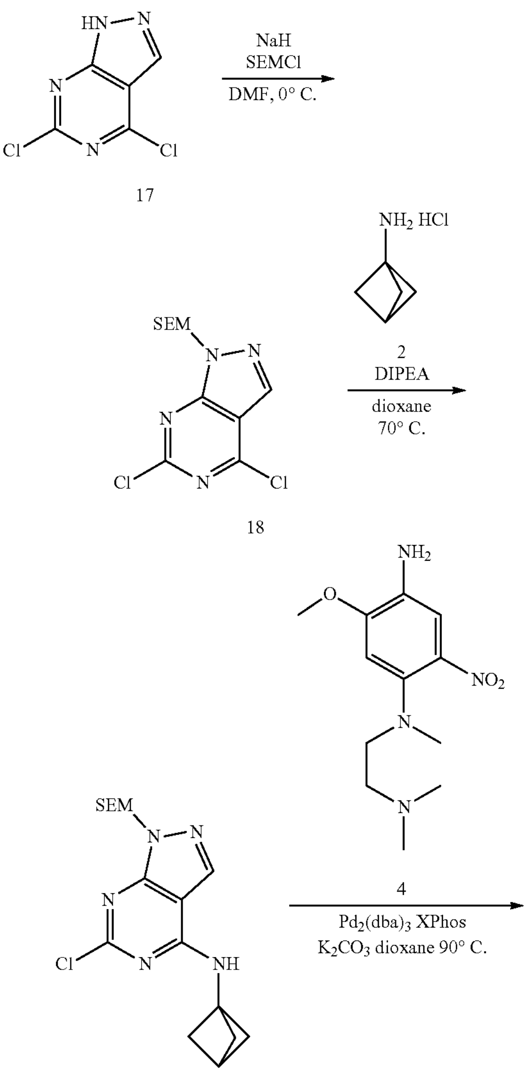

17

18

19

-continued

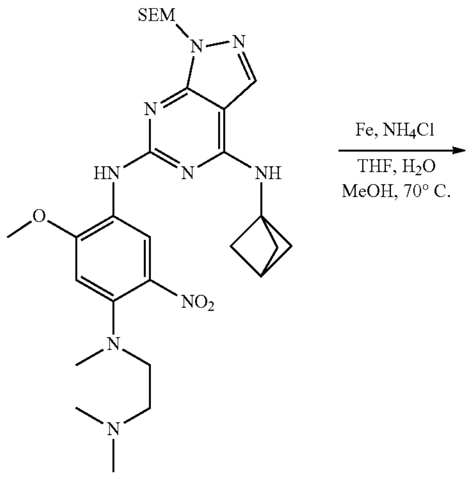

20

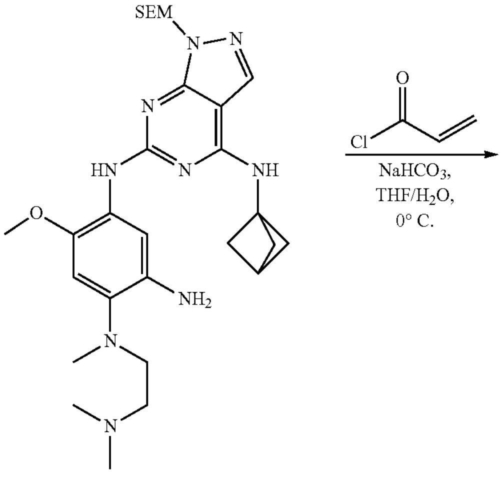

21

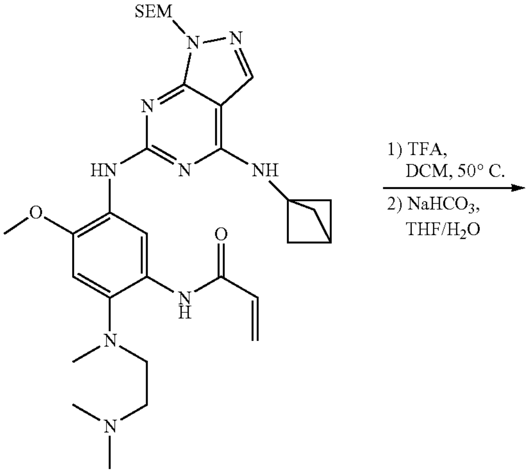

22

-continued

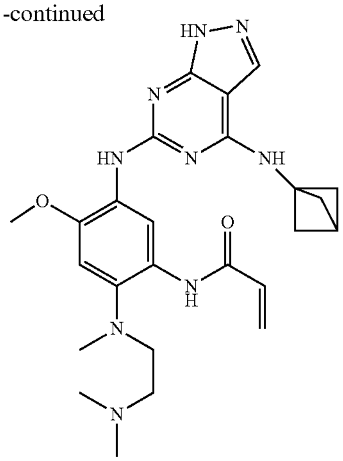

039

4,6-Dichloro-1-((2-(trimethylsilyl)ethoxy)methyl)-1H-pyrazolo[3,4-d]pyrimidine (18)

To a solution of 4,6-dichloro-1H-pyrazolo[3,4-d]pyrimidine 17 (442.5 mg, 2.34 mmol) in DMF (10 mL) at 0° C. was added sodium hydride (NaH, 73 mg, 3.04 mmol). The reaction mixture was stirred at 0° C. for 30 min, after which time 2-(trimethylsilyl)ethoxymethyl chloride (SEMCl, 540 NL, 3.05 mmol) was added and stirred at rt for 3 h. The reaction mixture was extracted with EtOAc, washed with $H_2O$ 2× and brine. The organic layer was collected and dried over $Na_2SO_4$, filtered, and concentrated in vacuo. Purification by silica flash chromatography gave the title compound 18 as a yellow solid (239.6 mg, 32% yield). LC-MS m/z: (pos) 318.97 ($[M+H]^+$).

N-(bicyclo[1.1.1]pentan-1-yl)-6-chloro-1-((2-(trimethylsilyl)ethoxy)methyl)-1H-pyrazolo[3,4-d]pyrimidin-4-amine (19)

To a solution of 4,6-dichloro-1-((2-(trimethylsilyl)ethoxy)methyl)-1H-pyrazolo[3,4-d]pyrimidine 18 (147.7 mg, 0.463 mmol) and bicyclo[1.1.1]pentan-1-amine hydrochloride 2 (61 mg, 0.509 mmol) in dioxane (8 mL) was added DIPEA (242 μL, 1.39 mmol). The reaction mixture was stirred at 70° C. for 4 h. Upon cooling to rt, the reaction mixture was concentrated in vacuo. Purification by silica flash chromatography gave the title compound 19 (97.1 mg, 57% yield). LC-MS m/z: (pos) 366.03 ($[M+H]^+$).

$N^4$-(bicyclo[1.1.1]pentan-1-yl)-N-(4-((2-(dimethylamino)ethyl)(methyl)amino)-2-methoxy-5-nitrophenyl)-1-((2-(trimethylsilyl)ethoxy)methyl)-1H-pyrazolo[3,4-d]pyrimidine-4,6-diamine (20)

To a solution of N-(bicyclo[1.1.1]pentan-1-yl)-6-chloro-1-((2-(trimethylsilyl)ethoxy)methyl)-1H-pyrazolo[3,4-d]pyrimidin-4-amine 19 (97.1 mg, 0.304 mmol) in dioxane (8 mL) was added aniline 4 (102 mg, 0.38 mmol) and potassium carbonate ($K_2CO_3$, 84 mg, 0.608 mmol). The reaction mixture was degassed for 5 min, then $Pd_2(dba)_3$ (14 mg, 0.015 mmol) and 2-dicyclohexylphosphino-2',4',6'-triisopropylbiphenyl (XPhos, 14.5 mg, 0.030 mmol) were added. The reaction mixture was stirred at 90° C. for 5 h. Upon cooling to rt, the crude mixture was filtered over a plug of celite, and concentrated in vacuo. Purification by silica flash chromatography gave the title compound 20 (141.6 mg, 78% yield). LC-MS m/z: (pos) 598.30 ([M+H]$^+$).

$N^4$-(4-(bicyclo[1.1.1]pentan-1-ylamino)-1-((2-(trimethylsilyl)ethoxy)methyl)-1H-pyrazolo[3,4-d]pyrimidin-6-yl)-$N^1$-(2-(dimethylamino)ethyl)-5-methoxy-$N^1$-methylbenzene-1,2,4-triamine (21)

To a solution of $N^4$-(bicyclo[1.1.1]pentan-1-yl)-$N^6$-(4-((2-(dimethylamino)ethyl)(methyl)amino)-2-methoxy-5-nitrophenyl)-1-((2-(trimethylsilyl)ethoxy)-methyl)-1H-pyrazolo[3,4-d]pyrimidine-4,6-diamine 20 (141.6 mg, 0.237 mmol) in 4:1 THF/MeOH (5 mL) was added iron powder (40 mg, 0.711 mmol), followed by satd. aq. $NH_4Cl$ (2 mL). The reaction mixture was stirred at 70° C. for 5 h. Upon cooling to rt, the reaction mixture was extracted with $CH_2Cl_2$ and washed with water. The organic layer was collected and dried over $Na_2SO_4$, filtered, and concentrated in vacuo to give the title compound 21 (110 mg, 82% yield), which was taken forward without purification. LC-MS m/z: (pos) 589.33 ([M+H]$^+$).

N-(5-((4-(bicyclo[1.1.1]pentan-1-ylamino)-1H-pyrazolo[3,4-d]pyrimidin-6-yl)amino)-2-((2-(dimethylamino)ethyl)(methyl)amino)-4-methoxyphenyl)acrylamide $N^4$-(4-(bicyclo[1.1.1]pentan-1-ylamino)-1-((2-(trimethylsilyl)ethoxy)methyl)-1H-pyrazolo[3,4-d]pyrimidin-6-yl)-$N^1$-(2-(dimethylamino)ethyl)-5-methoxy-$N^1$-methylbenzene-1,2,4-triamine 21 (55 mg, 0.097 mmol) was dissolved in THF (3 mL) and satd. aq. $NaHCO_3$ (1 mL) and cooled to 0° C. Acryloyl chloride (12 μL, 0.145 mmol) was added dropwise, and the reaction mixture was stirred at 0° C. for 15 min, then warmed to rt. The reaction mixture was extracted with EtOAc, washed with water and brine. The organic layer was collected and dried over $Na_2SO_4$, filtered, and concentrated in vacuo to give the crude acrylamide intermediate 22. LC-MS m/z: (pos) 622.36 ([M+H]$^+$).

The crude acrylamide intermediate 22 was dissolved in 1:3 TFA/$CH_2Cl_2$ (4 mL) and stirred at 50° C. for 3 h. Upon cooling to rt, the reaction mixture was concentrated in vacuo. The crude material was dissolved in THF (4 mL), and satd. aq. $NaHCO_3$ (4 mL) was added and stirred for 6 h. The reaction mixture was extracted with EtOAc, washed with water, and brine. The organic layer was collected and dried over $Na_2SO_4$, filtered, and concentrated in vacuo. Purification by HPLC gave the title compound 039 as a white solid (7.2 mg). LC-MS m/z: (pos) 492.25 ([M+H]$^+$).

Example 2—Inhibitory Activity Against Kinases in Ba/F3 Cells

The $IC_{50}$ values of the compounds provided herein were measured against kinases in Ba/F3 cells. Tables 2-6 summarize the data for the compounds disclosed herein in comparison to known compounds.

Activities of representative compounds of the present application in inhibiting EGFR and HER2 were tested by MTS assay (for Ba/F3 cell, DFCI58-229 cell, and DFCI127c cells) or by CellTiter-Glo® luminescent cell viability assay (for DFCI362JC cells). For assays with Ba/F3 cells, 3000 cells were seeded for per well in 96-well plates and were exposed to indicated compounds with a concentration of 3.3 to 10 μM for 72 hours. For assays with DFCI58-229 cell, DFCI127c cell, or DFCI362JC cell, 5000 cells were seeded per well in 96-well plates and were exposed to indicated compounds with a concentration of 3.3 to 10 μM for 72 hours.

Western blot analysis was then performed on the cells. The cells were plated at 5×10$^5$ cells per well in 6-well plates and treated with the indicated concentrations of the compound. After 6 hours of treatment, cells were washed with PBS and lysed with NP40 buffer (Calbiochem) supplemented with Complete Mini protease inhibitor and PhosSTOP phosphatase inhibitors (Roche). Lysates were then separated by SDS-PAGE gel, transferred to nitrocellulose membranes, and probed with the following antibodies: phospho-EGFR (Tyr1068) (3777), total EGFR (2232), p-Akt (Ser473) (4060), total Akt (9272), p-ERK(Thr202/Tyr204) (4370), total ERK (9102) (Cell Signaling), and HSP90 (SC-7947) (Santa Cruz Biotechnology).

TABLE 2

| | Ba/F3 $IC_{50}$ (nM) | | | | | |
|---|---|---|---|---|---|---|
| Compound No. | WT EGFR | SVD | ASV | WT HER2 | YVMA | GSP |
| 001 | 146.3 | 123.1 | 72.51 | 17.61 | 78.3 | 78.21 |
| 002 | 585.9 | 535.4 | 59.92 | 62.32 | 196 | 251.8 |
| 003 | 355.1 | 391.6 | 17.24 | 62 | 159.7 | 128.4 |
| 004 | 272.7 | 229 | 55.75 | 47.11 | 104.6 | 126.9 |
| 005 | 158.4 | 189.5 | 173.3 | 21.34 | 67.46 | 60.44 |
| 006 | 407.9 | 237.3 | 224.9 | 50.07 | 122.6 | 151.2 |
| 007 | 730.2 | 168.9 | 42.1 | 117.6 | 206.1 | 193.7 |
| 008 | 316.8 | 480.2 | 339 | 47.42 | 89.18 | 96.1 |
| 009 | 184.9 | 190.6 | 10.61 | 21.96 | 51.79 | 40.92 |
| 010 | 173.3 | 225.8 | 50.76 | 15.41 | 57.66 | 51.26 |
| 011 | 3149 | 2116 | 480.3 | 1562 | 1544 | 1712 |
| 012 | 396.3 | 436.4 | 39.68 | 60.67 | 147.5 | 146.8 |
| 013 | 16.53 | 6.102 | 5.113 | 2.596 | 5.668 | 12.79 |
| 022 | 28.56 | 12.32 | 13.85 | 3.463 | 10.21 | 20.73 |
| 027 | 413.5 | 332 | 85.94 | 120.5 | 360 | 335.8 |
| 037 | 1638 | 1241.1 | 631.4 | 59.06 | 533.3 | |
| 038 | 6593 | 4910 | 2298 | 551.8 | 2974 | |

TABLE 2-continued

| Compound No. | Ba/F3 $IC_{50}$ (nM) | | | | | |
|---|---|---|---|---|---|---|
| | WT EGFR | SVD | ASV | WT HER2 | YVMA | GSP |
| 039 | 98.46 | 40.6 | 21.82 | 3.52 | 15.92 | |
| JBJ178 lead | 178.3 | 507.4 | 27.87 | 3.822 | 1.387 | 2.212 |
| poziotinib | 1.023 | 1.54 | 0.936 | 0.504 | 0.5295 | 0.5467 |
| pyrotinib | 11.6 | 286 | 79.53 | 3.404 | 2.812 | 2.274 |
| TAS6417 | 53.81 | 42.24 | 29.68 | 91.14 | 21.48 | 19.21 |
| neratinib | 6.677 | 109.2 | 10.03 | 2.646 | 1.75 | 1.374 |

TABLE 3

| Compound No. | Ba/F3 $IC_{50}$ (μM) | | | | | | |
|---|---|---|---|---|---|---|---|
| | WT EGFR | SVD | ASV | WT HER2 | YVMA | GSP | parental |
| 014 | 0.05683 | 0.08994 | 0.1254 | 0.004951 | 0.01125 | 0.0142 | 7.375 |
| 015 | 0.07524 | 0.09079 | 0.1149 | 0.01307 | 0.03026 | 0.05445 | 6.263 |
| 016 | 4.181 | 4.228 | 4.165 | 2.68 | 1.642 | 1.986 | 4.338 |
| 017 | 1.156 | 0.8256 | 0.7149 | 0.5858 | 0.757 | 0.9376 | 2.297 |
| 018 | 3.178 | 3.969 | 4.309 | 0.8097 | 1.327 | 1.208 | 9.221 |
| 019 | 1.905 | 2.183 | 2.023 | 0.4127 | 0.9614 | 0.8616 | 4.249 |
| 020 | 0.8849 | 1.236 | 1.349 | 0.155 | 0.3856 | 0.4705 | 5.931 |
| 021 | 1.517 | 2.167 | 2.69 | 0.8438 | 1.357 | 1.392 | 6.039 |
| 028 | 5.022 | 5.383 | 6.642 | 4.268 | 4.688 | 4.053 | 10.5 |
| 029 | 1.678 | 1.304 | 1.874 | 0.3392 | 0.4753 | 0.7576 | 8.715 |
| 030 | 3.305 | 2.382 | 4.045 | 1.684 | 2.821 | 3.821 | 9.94 |
| 031 | 1.508 | 1.05 | 1.59 | 0.5513 | 0.9625 | 0.9874 | 8.052 |
| 013 | 0.029 | 0.04026 | 0.05485 | 0.01134 | 0.01927 | 0.03547 | 4.585 |

TABLE 4

| Compound No. | EGFR Ba/F3 (nM) | | | HER2 Ba/F3 (nM) | | |
|---|---|---|---|---|---|---|
| | WT EGFR | SVD | ASV | WT HER2 | YVMA | GSP |
| 001 | 146.3 | 123.1 | 72.51 | 17.61 | 78.3 | 78.21 |
| 002 | 585.9 | 535.4 | 59.92 | 62.32 | 196 | 251.8 |
| 003 | 355.1 | 391.6 | 17.24 | 62 | 159.7 | 128.4 |
| 004 | 272.7 | 229 | 55.75 | 47.11 | 104.6 | 126.9 |
| 005 | 158.4 | 189.5 | 173.3 | 21.34 | 67.46 | 60.44 |
| 006 | 407.9 | 237.3 | 224.9 | 50.07 | 122.6 | 151.2 |
| 007 | 730.2 | 168.9 | 42.1 | 117.6 | 206.1 | 193.7 |
| 008 | 316.8 | 480.2 | 339 | 47.42 | 89.18 | 96.1 |
| 009 | 184.9 | 190.6 | 10.61 | 21.96 | 51.79 | 40.92 |
| 010 | 173.3 | 225.8 | 50.76 | 15.41 | 57.66 | 51.26 |
| 011 | 3149 | 2116 | 480.3 | 1562 | 1544 | 1712 |
| 012 | 396.3 | 436.4 | 39.68 | 60.67 | 147.5 | 146.8 |
| 013 | 26.66 | 44.69 | 19.34 | 4.417 | 11.09 | 20.67 |
| 022 | 60.67 | 147.5 | 146.8 | 3.463 | 10.21 | 20.73 |
| 023 | 264.8 | 277.7 | 131.1 | 40 | 137.8 | 156.6 |
| 024 | 233.8 | 387.4 | 208.7 | 30.84 | 96 | 69.39 |
| 025 | 437.4 | 523.5 | 530.6 | N.D. | 169 | 180.7 |
| 026 | 187.8 | 163.8 | 122.9 | 14.51 | 11.49 | 24.99 |
| 027 | 413.5 | 332 | 85.94 | 120.5 | 360 | 335.8 |
| poziotinib | 1.31 | 1.898 | 1.308 | <1 | <1 | <1 |
| afatinib | 1.546 | 25.37 | 14.23 | 1.119 | 1.658 | 1.532 |
| DDC085 | 3.417 | 4.1 | 3.107 | <1 | 1.054 | 1.126 |
| neratinib | 6.566 | 110.6 | 21.78 | 2.23 | 1.494 | 1.431 |
| JBJ178 | 231.2 | 736.6 | 359.3 | 6.121 | 2.821 | 2.712 |
| irbinitinib | 3485 | N.D. | 4995 | 126.3 | 66.98 | 35.4 |

TABLE 5

| | Compound 022, nM | Compound 027, nM |
|---|---|---|
| wt EGFR | 27.02 | 459 |
| SVD | 19.44 | 551.1 |
| ASV | 12.35 | 376.8 |
| H | 28.53 | 444.5 |
| wt HER2 | 8.254 | 270.1 |
| YVMA | 10.98 | 386.6 |
| GSP | 25.98 | 470.2 |
| VC | 9.561 | 316.8 |
| WLV | 61.28 | 461.1 |
| exon19 | 0.9478 | 44.73 |

TABLE 6

| | $IC_{50}$ (μM) | |
|---|---|---|
| | Compound 031 | Compound 032 |
| EGFR WT | 4.317 | 0.4525 |
| EGFR SVD | 4.626 | 0.3347 |
| EGFR ASV | 2.877 | 0.2046 |
| HER2 WT | 0.8863 | 0.05324 |
| HER2 YVMA | 3.17 | 0.3244 |
| HER2 GSP | 2.532 | 0.348 |

The disclosed subject matter is not to be limited in scope by the specific embodiments and examples described herein. Indeed, various modifications of the disclosure in addition to those described will become apparent to those skilled in the art from the foregoing description. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula I:

(I)

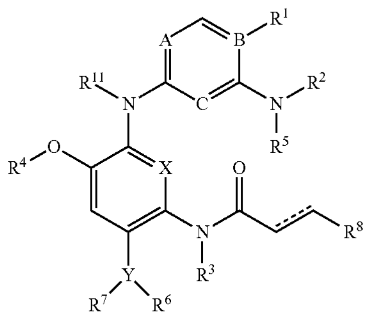

or a pharmaceutically acceptable salt thereof, wherein:

$\overset{\text{---}}{\text{---}}$ is an optional double bond;

A, B, and C are, independently at each occurrence, N, C, C—CN, or CH;

X is N or CH;

Y is N or O, provided that when Y is O, $R^6$ is absent;

$R^1$ is selected from the group consisting of hydrogen, halo, hydroxy, cyano, $C_1$-$C_3$ alkyl, $C_3$-$C_6$ cycloalkyl, $COR^{11}$, $CO_2R^{11}$, and $C_1$-$C_4$ alkoxy, wherein $R^1$ is absent if B is N, C—CN, or CH, and $C_1$-$C_3$ alkyl is optionally substituted with halo;

$R^2$ is selected from the group consisting of 5-7 membered heteroaryl and $C_3$-$C_8$ cycloalkyl; wherein 5-7 membered heteroaryl and $C_3$-$C_8$ cycloalkyl are optionally substituted with one, two, or three $R^9$; or $R^2$ is phenyl substituted one, two, or three times with a substituent selected from the group consisting of $C_1$-$C_6$ alkyl, hydroxy, 5-10 membered heteroaryl, O-(5-10 membered heteroaryl), and $C_1$-$C_6$ alkylamine, wherein $C_1$-$C_6$ alkyl is optionally substituted with $N(CH_3)_2$;

$R^3$ is hydrogen or $C_1$-$C_6$ alkyl;

$R^4$ is hydrogen or $C_1$-$C_4$ alkyl;

$R^5$ is hydrogen or methyl; or alternatively, $R^2$ and $R^5$, together with the nitrogen atom to which they are attached, form a 4-7 membered heterocyclic ring;

$R^6$ is hydrogen or $C_1$-$C_6$ alkyl;

$R^7$ is $C_1$-$C_6$ alkyl or —$C_1$-$C_4$ alkyl-N($C_1$-$C_4$ alkyl)$_2$;

or, alternatively, $R^6$ and $R^7$, together with the nitrogen to which they are attached, form a 4- or 5-membered heterocyclic ring; wherein the 4- or 5-membered heterocyclic ring is optionally substituted with one or two $R^{10}$;

$R^8$ is hydrogen or —$CH_2N(CH_3)_2$;

$R^9$ is, independently at each occurrence, selected from the group consisting of halo, $C_1$-$C_6$ alkyl, hydroxy, $C_1$-$C_6$ alkoxy, 5-10 membered heteroaryl, O-(5-10 membered heteroaryl), and $C_1$-$C_6$ alkylamine, wherein $C_1$-$C_6$ alkyl is optionally substituted with one, two, or three halo or $N(CH_3)$;

or, alternatively, two $R^9$ groups, together with the atoms to which they are attached, form a 3-, 4-, or 5-membered ring;

$R^{10}$ is selected from the group consisting of OH, $C_1$-$C_4$ alkoxy, and $N(CH_3)_2$; and $R^{11}$ is independently, at each occurrence, selected from the group consisting of hydrogen, $C_1$-$C_6$ alkyl, and $C_3$-$C_6$ cycloalkyl.

2. The compound according to claim 1, wherein $R^4$ is methyl.

3. The compound according to claim 1, wherein $R^5$ is hydrogen.

4. The compound according to claim 1, wherein $\overset{\text{---}}{\text{---}}$ is a double bond.

5. The compound according to claim 1, wherein the compound of Formula I is a compound of Formula II:

(II)

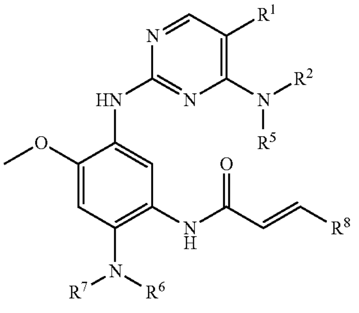

or a pharmaceutically acceptable salt thereof.

6. The compound according to claim 1, wherein the compound of Formula I is a compound of Formula III:

(III)

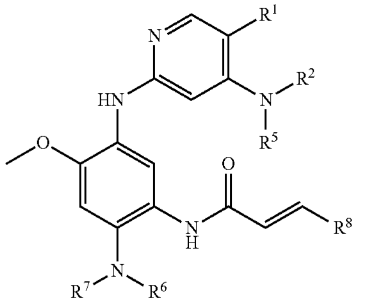

or a pharmaceutically acceptable salt thereof.

7. The compound according to claim 1, wherein the compound of Formula I is a compound of Formula IV:

(IV)

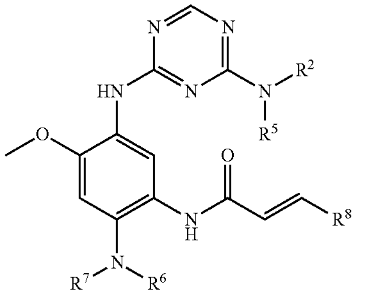

or a pharmaceutically acceptable salt thereof.

8. The compound according to claim 1, wherein the compound of Formula I is a compound of Formula V:

(V)

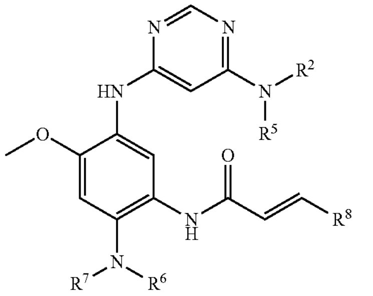

or a pharmaceutically acceptable salt thereof.

9. The compound according to claim 1, wherein B is C and $R^1$ is selected from the group consisting of cyano, hydroxy, methoxy, cyclopropyl, and $CF_3$.

10. The compound according to claim 1, wherein $R^2$ is

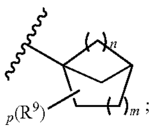

;

wherein:

m is 0, 1, or 2;

n is 1 or 2; and p is 0, 1, 2, or 3.

11. The compound according to claim 1, wherein $R^6$ is methyl and $R^7$ is $—CH_2CH_2N(CH_3)_2$.

12. The compound according to claim 1, wherein $R^6$ and $R^7$, together with the nitrogen to which they are attached, form a 4- or 5-membered heterocyclic ring selected from the group consisting of

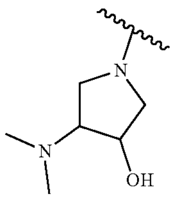
,
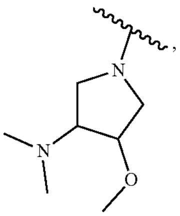
,
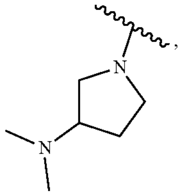
, and
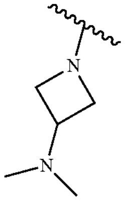
.

13. The compound according to claim 1, wherein $R^2$ is bicyclo[1.1.1]pentane or bicyclo[2.2.2]octane, both of which are optionally substituted with one, two, or three $R^9$.

14. The compound according to claim 1, wherein $R^2$ is selected from the group consisting of:

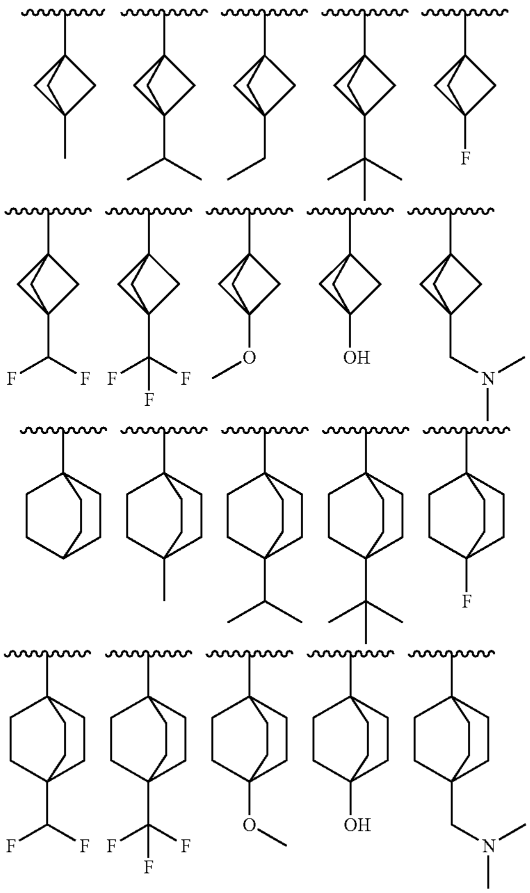

-continued
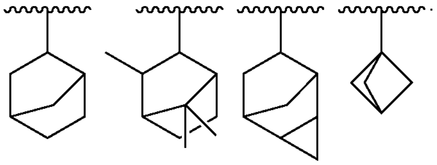
15. The compound according to claim 1, wherein the compound of Formula I is selected from the group consisting of
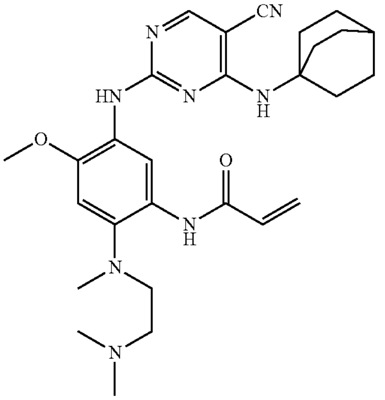
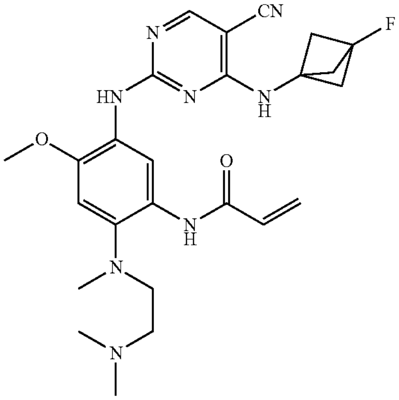
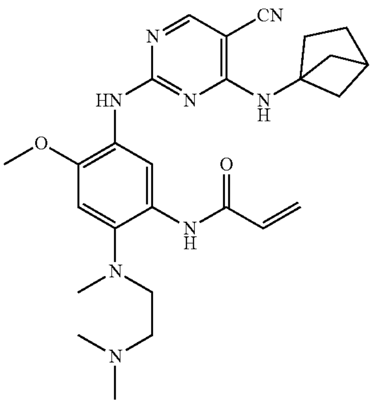
-continued
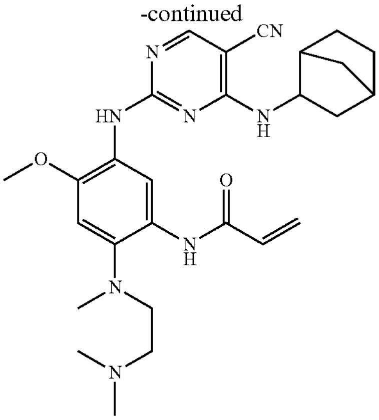
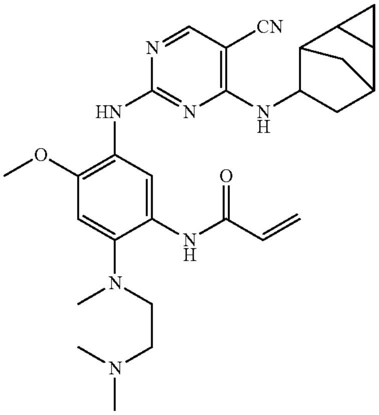
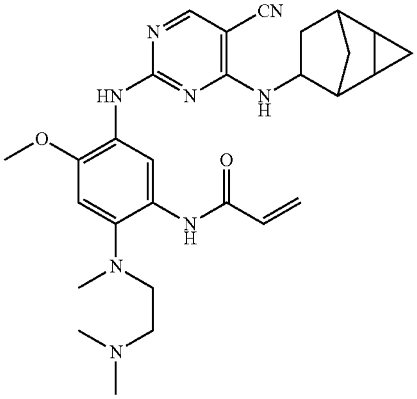
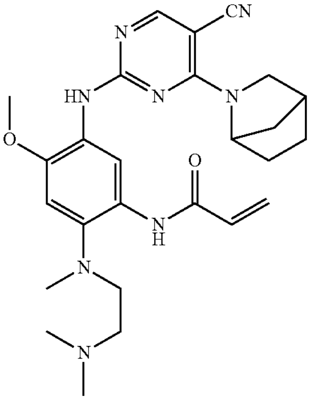

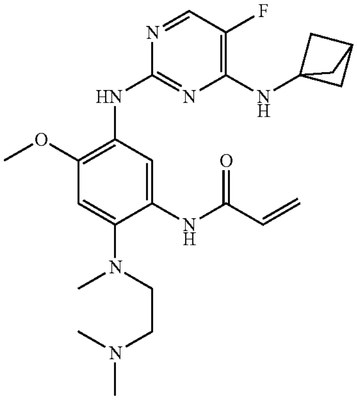
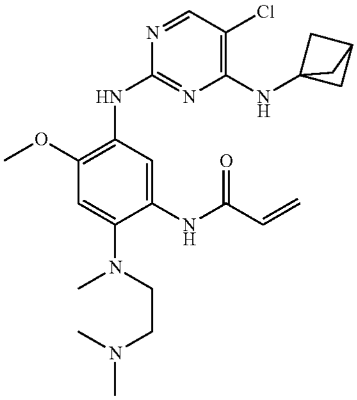
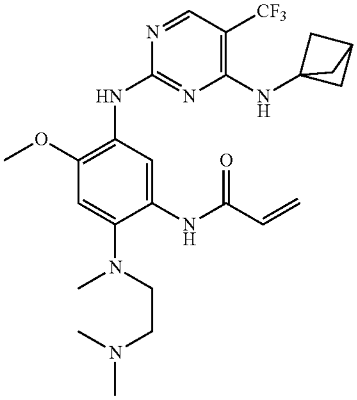
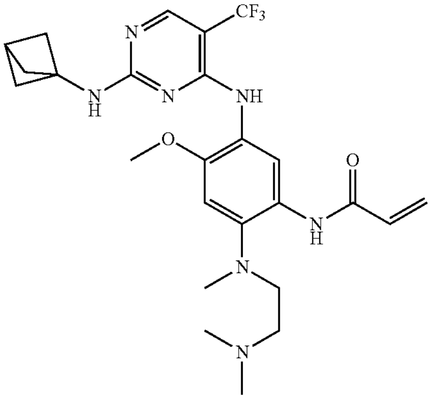
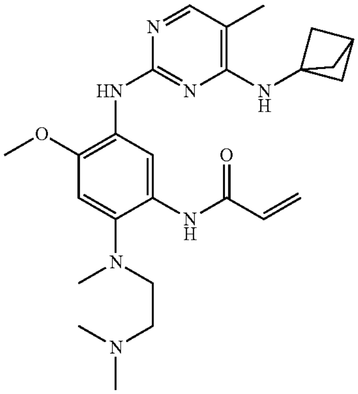
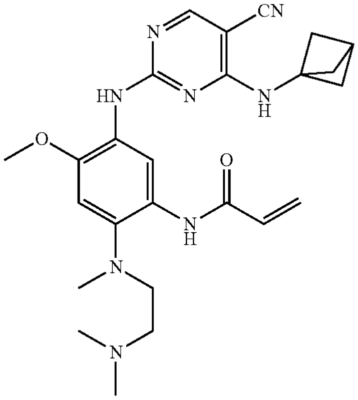
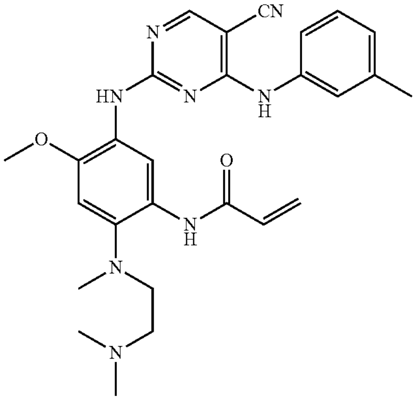
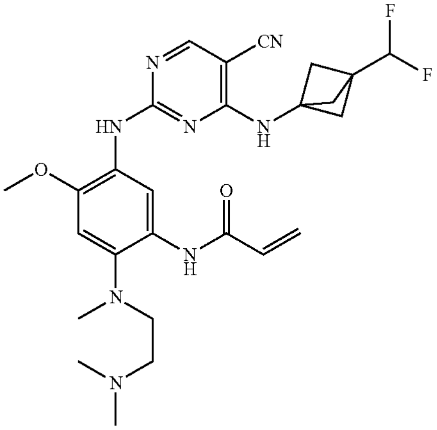

-continued
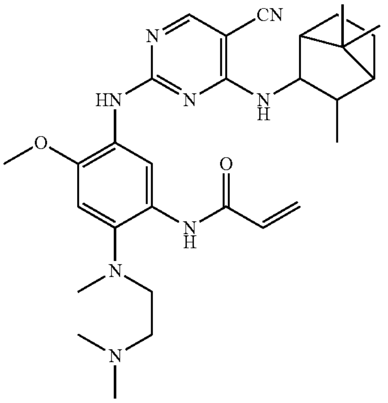
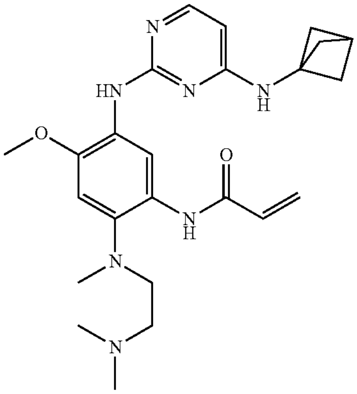
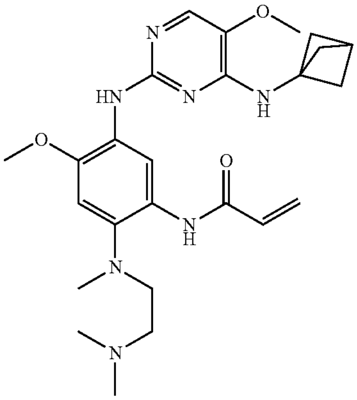
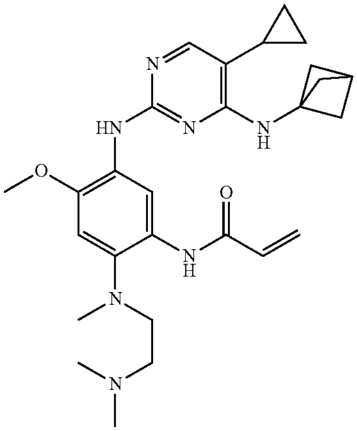
-continued
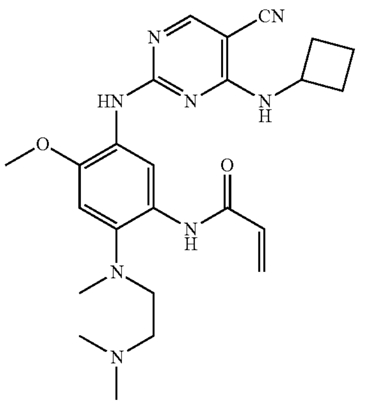
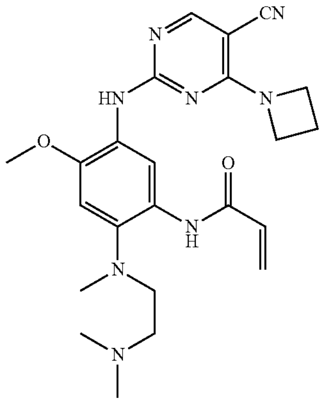
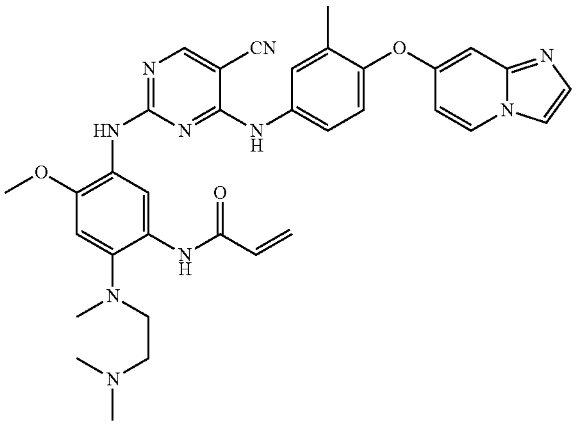
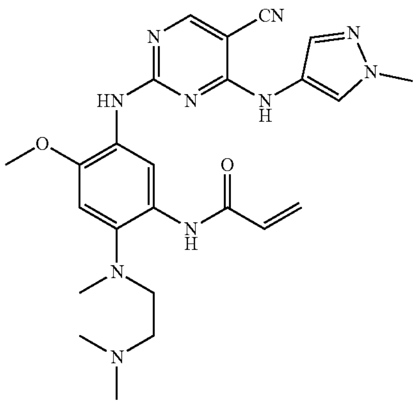

-continued
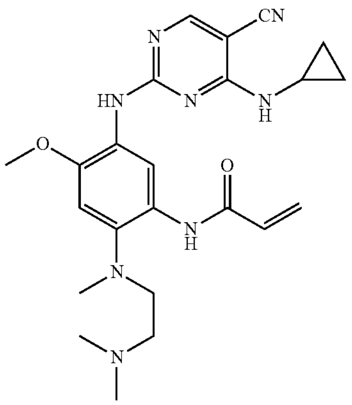
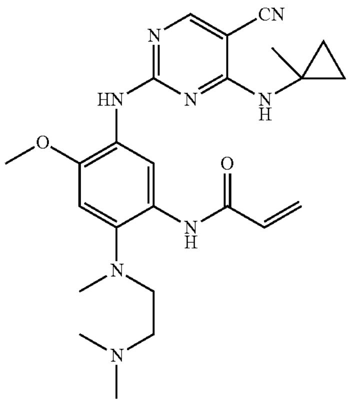
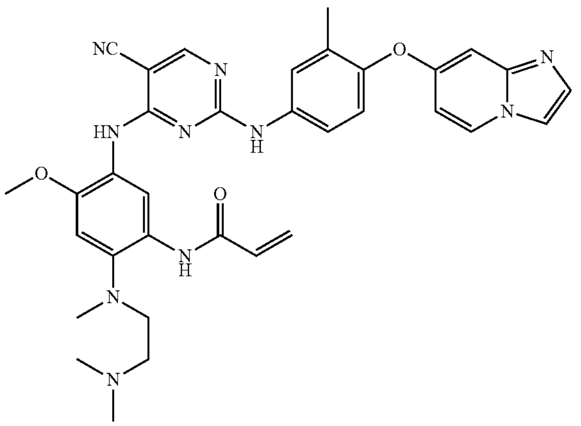
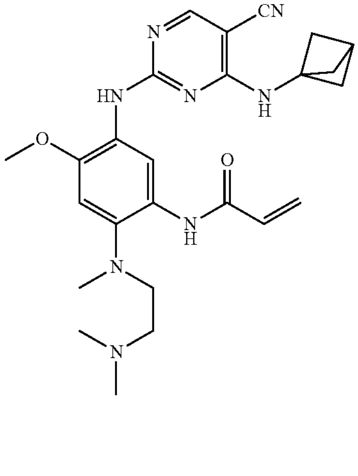
-continued
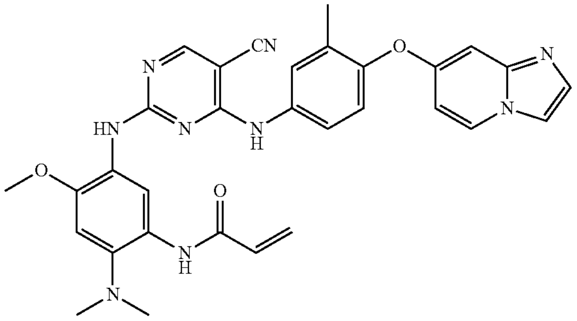
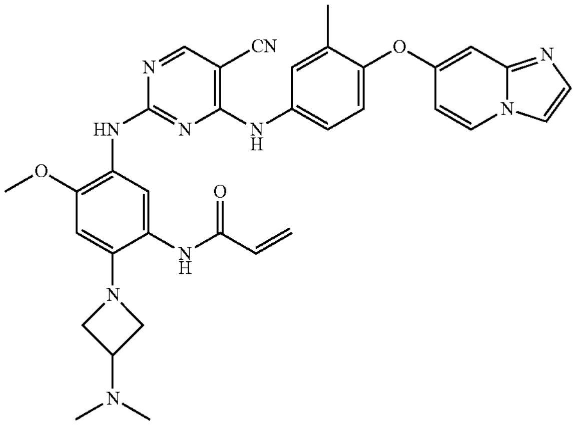
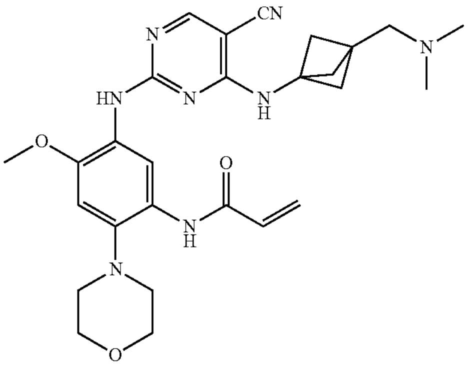
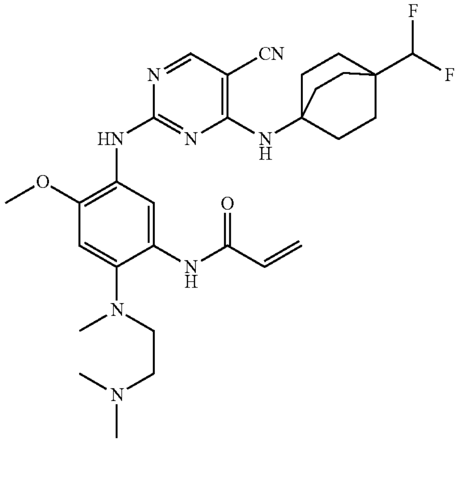

-continued

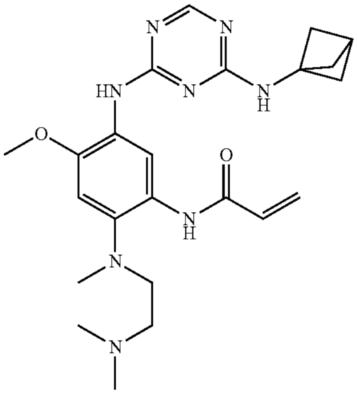

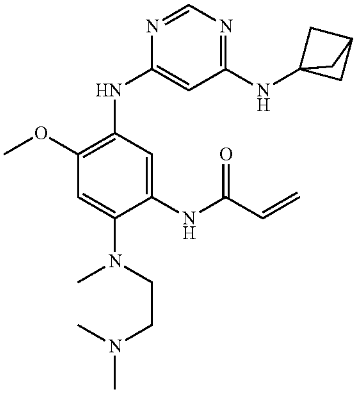

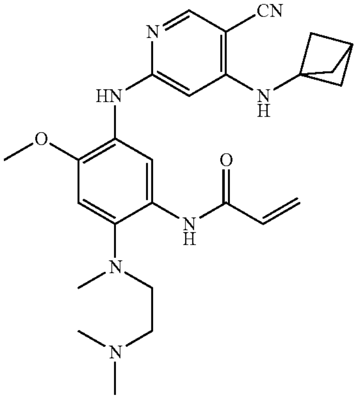

-continued

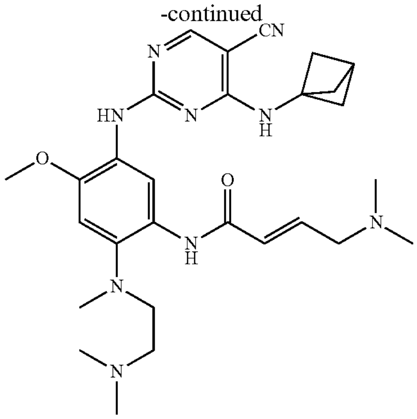

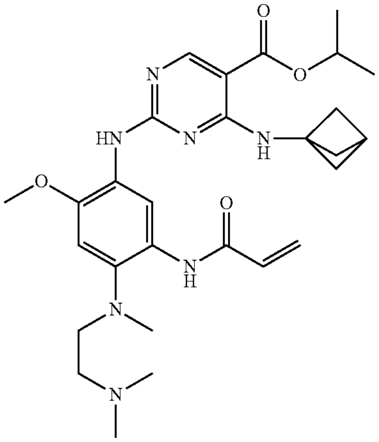 [SMILES: C=CC(=O)Nc1cc(Nc2ncc(C(=O)OC(C)C)c(NC34CC(C3)C4)n2)c(OC)cc1N(C)CCN(C)C]

or a pharmaceutically acceptable salt thereof.

16. A pharmaceutical composition comprising a compound according to claim 1, or a salt thereof, and at least one pharmaceutically acceptable carrier.

17. A method of treating non-small cell lung cancer (NSCLC) in an individual in need thereof, comprising administering to the individual a therapeutically effective amount of a compound according to claim 1.

18. A method of inhibiting EGFR and/or HER2 in an individual in need thereof, comprising administering to the individual a therapeutically effective amount of a compound according to claim 1.

19. The method according to claim 18, wherein EGFR or HER2 is characterized by in-frame insertions in exon 20.

* * * * *